US009226984B2

(12) United States Patent
Petersen et al.

(10) Patent No.: US 9,226,984 B2
(45) Date of Patent: Jan. 5, 2016

(54) ENTRAPMENT OF RADIONUCLIDES IN NANOPARTICLE COMPOSITIONS

(75) Inventors: Anncatrine Luisa Petersen, Nivå (DK); Jonas Rosager Henriksen, Allerød (DK); Palle Hedengran Rasmussen, Taastrup (DK); Andreas Kjær, Frederiksberg (DK); Thomas Lars Andresen, Vanløse (DK)

(73) Assignee: Technical University of Denmark and Rigshospitalet (DK)

( * ) Notice: Subject to any disclaimer, the term of this patent is extended or adjusted under 35 U.S.C. 154(b) by 12 days.

(21) Appl. No.: 13/992,080

(22) PCT Filed: Dec. 14, 2011

(86) PCT No.: PCT/DK2011/050479
§ 371 (c)(1),
(2), (4) Date: Jun. 6, 2013

(87) PCT Pub. No.: WO2012/079582
PCT Pub. Date: Jun. 21, 2012

(65) Prior Publication Data
US 2013/0251630 A1     Sep. 26, 2013

Related U.S. Application Data

(60) Provisional application No. 61/434,070, filed on Jan. 19, 2011.

(30) Foreign Application Priority Data

Dec. 14, 2010  (DK) ................................. 2010 70542
Jan. 19, 2011  (EP) ..................................... 11151372

(51) Int. Cl.
*A61K 51/00*    (2006.01)
*A61M 36/14*    (2006.01)
*A61K 51/12*    (2006.01)
*A61K 51/04*    (2006.01)

(52) U.S. Cl.
CPC ......... *A61K 51/1203* (2013.01); *A61K 51/1234* (2013.01); *A61K 51/0408* (2013.01); *A61K 51/12* (2013.01)

(58) Field of Classification Search
CPC ................................................. A61K 51/0408
See application file for complete search history.

(56) References Cited

U.S. PATENT DOCUMENTS

| 4,310,506 | A | 1/1982 | Baldeschwieler et al. | 424/1 |
| 5,182,398 | A | 1/1993 | Kasuga et al. | 546/171 |
| 5,213,804 | A | 5/1993 | Martin et al. | 424/450 |
| 5,258,499 | A | 11/1993 | Konigsberg et al. | 530/351 |
| 5,525,232 | A | 6/1996 | Veiro et al. | 210/638 |
| 5,688,488 | A | 11/1997 | Low et al. | 424/1.69 |
| 5,945,502 | A | 8/1999 | Hsieh et al. | 528/101 |
| 6,306,393 | B1 * | 10/2001 | Goldenberg | 424/141.1 |
| 2009/0081121 | A1 | 3/2009 | Ting et al. | 424/1.21 |
| 2012/0213698 | A1 | 8/2012 | Petersen et al. | 424/1.37 |

FOREIGN PATENT DOCUMENTS

| EP | 0 386 146 B1 | 9/1990 | A61K 43/00 |
| EP | 0565361 A1 * | 7/1993 | A61K 9/127 |
| EP | 1 486 216 A1 | 12/2004 | A61K 51/00 |
| JP | 2006-45132 | 2/2006 | A61K 49/00 |
| WO | WO 01/60417 A2 | 8/2001 | A61K 51/00 |
| WO | WO 03/041682 A2 | 5/2003 | A61K 9/00 |
| WO | WO 2004/082626 A2 | 9/2004 | |
| WO | WO 2004/082627 A2 | 9/2004 | |
| WO | WO 2006/021008 A2 | 2/2006 | A61K 31/00 |
| WO | WO 2006/043083 A2 | 4/2006 | A61K 51/12 |
| WO | WO 2006/095234 A2 | 9/2006 | |
| WO | WO 2009/140215 A2 | 11/2009 | |

OTHER PUBLICATIONS

International Searching Authority, International Search Report—International Application No. PCT/DK2011/050479, dated Mar. 15, 2012, together with the Written Opinion of the International Searching Authority, 19 pages.
International Preliminary Examining Authority, International Preliminary Report on Patentability, Application No. PCT/DK2011/050479, dated May 13, 2013, 12 pages.
U.S. Appl. No. 13/383,310, filed May 9, 2012.
Allen, et al., "Drug Delivery Systems: Entering the Mainstream," *Science*, 303, pp. 1818-1822, Dated: 2004.
Anderson, et al., "In Vitro and In Vivo Evaluation of Copper-64-Octreotide Conjugates," *The Journal of Nuclear Medicine*, vol. 36, pp. 2315-2325, Dated: 1995.
Ceh, et al., "Kinetics of Accumulation of Molecules into Liposomes," *J. Phys. Chem. B.*, 102; pp. 3036-3043, Dated 1998.
Choi & Hwang, "Mechanism of Ionophoric Transport of Indium-111 Cations Through a Lipid Bilayer Membrane," *J Nucl Med.* 28:91-96, Dated: 1987.

(Continued)

*Primary Examiner* — Michael G. Hartley
*Assistant Examiner* — Melissa Perreira
(74) *Attorney, Agent, or Firm* — Sunstein Kann Murphy & Timbers LLP

(57) ABSTRACT

The present invention is directed to the technical field of imaging compositions useful for diagnosing cancer and other diseases in a subject. In particular, the invention relates to a class of diagnostic compounds comprising a novel liposome composition with encapsulated metal entities such as radionuclides, for example $^{61}$Cu and $^{64}$Cu copper isotopes. The invention further relates to a novel method for loading delivery systems, such as liposome compositions, with metal entities such as radionuclides, and the use of liposomes for targeted diagnosis and treatment of a target site, such as cancerous tissue and, in general, pathological conditions associated with leaky blood vessels. The present invention provides a new diagnostic tool for the utilization of positron emission tomography (PET) imaging technique.

16 Claims, 7 Drawing Sheets

(56) References Cited

OTHER PUBLICATIONS

Crescitelli, "Effects of Oxine, Carbostyril and Quinoline on Frog Nerve," *Am J Physiol*, 163: pp. 197-200; Dated: 1950.

Dehdashti et al., "Initial Results With Pet Imaging Using Cu-64-Labeled Teta-Octreotide in Patients With Carcinoid Tumor," *Proceedings of the 44th Annual Meeting Abstract 381*, vol. 38, p. 103P, Dated: 1997.

Emfietzoglou, et al., "An Analytic Dosimetry Study for the Use of Radionuclide—Liposome Conjugates in Internal Radiotherapy," *The Journal of Nuclear Medicine*, vol. 42, 3, pp. 499-504, Dated: 2001.

Ferrara, Katherine W. et al., "Lipid-Shelled Vehicles: Engineering for Ultrasound Molecular Imaging and Drug Delivery," *Accounts of Chemical Research*, vol. 42, No. 7, pp. 881-892, Dated: Jul. 21, 2009.

Fischer P. W. F., et al., "Copper Transport by Intestinal Brush Border Membrane Vesicles From Rats Fed High Zinc or Copper Deficient Diets," *Nutrition Research*, vol. 5, No. 7, pp. 759-767, Dated: 1985.

Friggeri, et al., "Entrapment and Release of Quinoline Derivatives Using a Hydrogel of a Low Molecular Weight Gelator," *Journal of Controlled Release*, Elsevier, Amsterdam, NL, vol. 97, No. 2, Dated: Jun. 18, 2004.

Gabizon, et al., "An Improved Method for in Vivo Tracing and Imaging of Liposomes Using a Gallium 67-Deferoxamine Complex," *Journal of Liposome Research*, 1, pp. 123-135, Dated: 1988.

Gabizon, et al., "Effect of Liposome Composition and Other Factors on the Targeting of Liposomes to Experimental Tumors: Biodistribution and Imaging Studies," *Cancer Research*, 50, pp. 6371-6378, Dated: 1990.

Goto, et al., "Liposomes Prepared From Synthetic Amphiphiles. I. Their Technetium Labeling and Stability," *Chem. Pharm. Bull.*, 37, pp. 1351-1354, Dated: 1989.

Hauser et al, "Ion Permeability of Phospholipid Bilayers" *Nature*, vol. 239, pp. 342-344, Dated: Oct. 6, 1972.

Henriksen G. et al, "Sterically Stabilized Liposomes as a Carrier for α-Emitting Radium and Actinium Radionuclides," *Nuclear Medicine and Biology*, Elsevier, NY, US, vol. 31, No. 4, pp. 441-449, Dated: May 1, 2004.

Hwang, et al., "Encapsulation, With High Efficiency, of Radioactive Metal Ions in Liposomes," *Biochim Biophys Acta.*, 716, pp. 101-109, Dated: 1982.

Kostarelos et al, "Liposomes as Carriers of Radionuclides: From Imaging to Therapy," *Journal of Liposome Research*, 9, pp. 429-460, Dated: 1999.

Kostarelos et al, "Liposome-Mediated Delivery of Radionuclides to Tumor Models for Cancer Radiotherapy: a Quantitative Analysis" *Journal of Liposome Research*, 9(3) pp. 407-424, Dated 1999.

Lasic, Dan D., "Novel Applications of Liposomes," *Trends Biotechnol.*, 25 vol. 16, pp. 307-321, Dated: 1998.

Mills, et al, "Lysolipid Incorporation in Dipalmitoylphosphatidylcholine Bilayer Membranes Enhances the Ion Permeability and Drug Release Rates at the Membrane Phase Transition," *Biochim. Biophys. Acta*, 1716: pp. 77-96, Dated: 2005.

Mittal et al., "8-Hydroxyquinoline Based Neutral Tripodal Ionophore as a Copper (II) Selective Electrode and the Effect of Remote Substituents on Electrode Properties," *Analytica Chimica Acta* 585: pp. 161-170, Dated: 2007.

Morgan, et al., "Localisation of Experimental Staphylococcal Abscesses by 99MTC-Technetium-Labelled Liposomes," *J Med Microbiol.* vol. 14, pp. 213-217, 1981.

Papahadjopoulos, et al., "Permeability Properties of Phospholipid Membranes Effect of Cholesterol and Temperature," *Biochim. Biophys. Acta.*, 266: pp. 561-583, Dated: 1971.

Paula, et al., "Permeation of Halide Anions Through Phospholipid Bilayers Occurs by the Solubility—Diffusion Mechanism," *Biophys. J.*, 74: pp. 319-327, Dated: 1998.

Phillips, et al., "A Simple Method for Producing a Technetium-99m-Labeled Liposome Which is stable In Vivo," *Nucl. Med. Biol., Int. J. Radiat. Appl. Instrum. Part B.*, vol. 19, No. 5, pp. 539-547, Dated: 1992.

Phillips, William T, "Delivery of Gamma-Imaging Agents by Liposomes," *Advanced Drug Delivery Reviews* 37: pp. 13-32, Dated: 1999.

Puskin, J., "Divalent Cation Binding to Phospholipids: An EPR Study," J. Membrane Biol., 35 pp. 39-55, Dated: 1977.

Seo, et al., "A Novel Method to Label Preformed Liposomes with $^{64}$Cu for Positron Emission Tomography (PET) Imaging," *Bioconjucate Chem.*, 19, pp. 2577-2584, Dated: 2008.

Seo, Youngho, "Quantification of SPECT and PET for Drug Development," *Curr. Radiopharm.*, 1, pp. 17-21, Dated: 2008.

Wang, et al., "Internal Radiotherapy and Dosimetric Study for $^{111}$In/$^{177}$Lu-pegylated Liposomes Conjugates in Tumor-Bearing Mice." *Nuclear Instruments and Methods in Physics Research*, pp. 533-537, Dated: 2006.

Zhai et al., "Tumor Cellular Proteasome Inhibition and Growth Suppression by 8-hydroxyquinoline and Clioquinol Requires their Capabilities to Bind Copper and Transport Copper into Cells," *J Biol Inorg Chem.*, 15: pp. 259-269, Dated: 2010.

Japan Patent Office Office Action for Application No. JP 2013-543530, dated Oct. 2, 2015, 5 pages.

Japan Patent Office Office Action for Application No. JP 2013-543530, dated Oct. 2, 2015, 3 pages [English translation].

* cited by examiner

US 9,226,984 B2

ENTRAPMENT OF RADIONUCLIDES IN NANOPARTICLE COMPOSITIONS

FIELD OF INVENTION

The present invention is directed to the technical field of imaging compositions useful for diagnosing cancer and other diseases in a subject. In particular, the invention relates to a class of diagnostic compounds comprising a novel liposome composition with encapsulated radionuclides or metal entities, such as for example $^{61}$Cu and $^{64}$Cu copper isotopes. The invention further relates to a novel method for loading delivery systems, such as liposome compositions, with metal entities such as radionuclides and the use of liposomes comprising metal entities such as radionuclides for targeted diagnosis and therapy of a target site, such as cancerous tissue and, in general, pathological conditions associated with leaky blood vessels. The present invention provides a new diagnostic tool for the utilization of positron emission tomography (PET) imaging technique.

BACKGROUND OF INVENTION

Liposomes can serve as vesicles to deliver a wide range of encapsulated and/or membrane-incorporated therapeutic or diagnostic entities. Liposomes are usually characterized as nano-scale vesicles consisting of an interior core separated from the outer environment by a membrane of one or more bilayers. The bilayer membranescan be formed by amphiphilic molecules e.g. synthetic or natural lipids that comprise a hydrophobic and a hydrophilic domain [Lasic, Trends Biotechnol., 16: 307-321, 1998]. Bilayer membranes can also be formed by amphiphilic polymers constituting particles (e.g. polymersomes and polymerparticles).

Liposomes can serve as carriers of an entity such as, without limitation, a chemical compound, or a radionuclide, that is capable of having a useful property or provide a useful activity. For this purpose, the liposomes are prepared to contain the desired entity in a liposome-incorporated form. The liposome incorporated entity can be associated with the exterior surface of the liposome membrane, located in the interior core of the liposome or within the bilayer of the liposome. Methods for the incorporation of radionuclides into liposomes are e.g. surface labeling after liposome preparation [Phillips, Adv Drug Deliv Rev., 37: 13-32, 1999], label incorporation into the lipid bilayer of preformed liposomes [Morgan et al., J Med. Microbiol., 14: 213-217, 1981], surface labeling of preformed liposomes by incorporating lipid chelator conjugate during preparation [Goto et al., Chem harm Bull. (Tokyo), 37: 1351-1354, 1989; Seo et al., Bioconjucate Chem., 19: 2577-2584, 2008], and aqueous phase loading of preformed liposome [Hwang et al., Biochim Biophys Acta., 716: 101-109, 1982; Phillips et al., Int J Rad Appl Instrum B, 19: 539-547, 1992; Gabizon et al., J Liposome Res., 1: 123-125, 1988; Henriksen et al., Nucl Med. Bio., 31: 441-449, 2004]. The incorporation of entities into liposomes by the aqueous phase loading of preformed liposome is also referred to as "loading" and thereby "encapsulating" or "entrapping" the entities.

Encapsulating entities into the interior of liposomes through aqueous phase loading seems to provide the greatest in vivo stability, because of the protected location of the entity inside the liposome. The purpose of encapsulating an entity into a liposome is often to protect the entity from the destructive environment and rapid excretion in vivo. The entrapment of the entity provides the opportunity for the encapsulated entity to apply the activity of the entity mostly at the site or in the environment where such activity is advantageous but less so at other sites where the activity may be useless or undesirable. It is known that liposomes having PEG chains attached to the outer surface have prolonged circulation time in the blood stream. These liposome compositions can effectively evade the immune system, which would otherwise attack the liposomes soon after injection causing fast clearance or rupture of the liposome and premature release of the agent entrapped inside. By increasing the blood circulation time, the agent entrapped in the liposome stays within the liposome until it reaches the target tissue. This phenomenon is referred to as passive targeting delivery, where an accumulation of long-circulating nanoparticles in tumor areas or inflammatory sites is due to leaky vasculature and lack of an effective lymphatic drainage system in these areas. For example, a radio-diagnostic entity entrapped within a long-circulating liposome can be delivered by passive targeting to a diseased site within a subject to facilitate a diagnosis thereof. Active- or ligand targeting delivery systems is referred to liposome compositions with ligands attached on the surface targeted against cell surface antigens or receptors [Allen, Science, 303: 1818-1822, 2004]. Combining the properties of targeted and long-circulating liposomes in one preparation comprising a radionuclide encapsulated liposome composition would significantly enhance the specificity and intensity of radioactivity localization in the target site e.g. a tumor. Ideally, such liposome compositions can be prepared to include the desired entity, e.g. a chemical compound or radionuclide, (i) with a high loading efficiency, i.e., high percentage of encapsulated entity relative to the total amount of the entity used in the encapsulation process, and (ii) in a stable form, i.e., with minimal release (i.e. leakage) of the encapsulated entity upon storage or generally before the liposome reaches the site or the environment where the liposome entrapped entity is expected to apply its intended activity.

Entrapment of radionuclides into nanoparticles such as liposomes can be obtained through use of chemical compounds called ionophores capable of transporting metal ions across lipid membranes. Upon crossing the membrane barrier the radionuclide then binds preferably to a chelator, encapsulated in the interior of the liposome composition, due to its stronger affinity thereto, allowing the release of free ionophore, and the entrapment of the radionuclide in the liposome composition.

Copper isotopes are of great interest for use in diagnostic and/or therapeutic application. For diagnostic applications this relates to the positron-emitters $^{61}$Cu and $^{64}$Cu, which can be used in positron emission tomography (PET) diagnostic imaging. $^{64}$Cu is an interesting copper isotope possessing all decay modalities, and with a half-life of 12.7 h it is favorable for biological studies. A half-life of about 6-12 h appears to be ideal to allow for sufficient accumulation of liposome in inflammatory tissues or cancerous targets, yet providing enough background clearance to permit early identification of the target [Gabizon et al., Cancer Res., 50: 6371-6378, 1990]. Furthermore, $^{64}$Cu can be used as a model nuclide representing the chemical properties of all copper isotopes.

Ideal radioisotopes for therapeutic applications are those with low penetrating radiation, such as β-, α- and auger electron-emitters. Examples of such radioisotopes are $^{67}$Cu, $^{67}$Ga, $^{225}$Ac, $^{90}$Y, $^{177}$Lu and $^{119}$Sb. When the low energy emitting radioisotope in the form of a radiopharmaceutical reach the target site, the energy emitted is only deposited at the target site and nearby normal tissues are not irradiated. The energy of the emitted particles from the different radioisotopes and their ranges in tissues will vary, as well as their half-life, and the most appropriate radioisotope will be different depending on the application, the disease and the accessibility of the disease tissue.

Ideal radioisotopes for diagnostic applications are those with relatively short half-life, and those with high penetrating radiation to be detected by imaging techniques such as positron emission tomography (PET) and/or single photon emission computed tomography (SPECT). The half-life of the radionuclide must also be long enough to carry out the desired chemistry to synthesize the radiopharmaceutical and long enough to allow accumulation in the target tissue in the patient while allowing clearance through the non-target organs. The radionuclide, $^{64}$Cu, has proven to be a versatile isotope with respect to is applications in both imaging [Dehdashti et al., J Nucl Med. 38: 103P, 1997] and therapy [Anderson et al., J Nucl Med., 36: 2315-2325, 1998]. Radiopharmaceuticals and for example radiolabeled liposome compositions consisting of radionuclides, such as $^{61}$Cu (T½=3.33 h) and $^{64}$Cu (T½=12.7 h) can be utilized for imaging by the positron emission tomography (PET) technique, with the main advantages over single photon emission computed tomography (SPECT) being: a) employing annihilation coincidence detection (ACD) technique whereby only photons detected simultaneously ($<10^{-9}$ sec) by a pair of scintillators opposite each other are registered, instead of collimator, the sensitivity is markedly improved (×30-40) and the spatial resolution is enhanced by about a factor of two (<5 mm), since the detection field is (non-diverging) defined cylindrical volume and both the sensitivity and the resolution do not vary within the detection field [Kostarelos et al., J Liposome Res., 9: 429-460, 1999]; b) PET scanners provide all images in the unit of radioactivity concentrations (e.g. Bq/ml) after corrections for photon attenuation, scatters and randoms, thereby considering PET to be a more quantitative technique than SPECT [Seo, Curr. Radiopharm., 1: 17-21, 2008].

The patent applications WO/2001/060417, WO/2004/082627, WO/2004/082626 and US 20090081121, describe methods based on ionophoric loading of radionuclides into liposomes. Further, the disclosed radionuclides which are loaded into liposomes are heavy radionuclides and $^{11}$C, $^{18}$F, $^{76}$Br, $^{77}$Br, $^{89}$Zr, $^{67}$Ga, $^{111}$In, $^{177}$Lu, $^{90}$Y and $^{225}$Ac. From a diagnostic standpoint, these approaches are not useable for PET imaging applications, but only SPECT, because of the limited use of radionuclides.

Patent EP386 146 B1 describes a composition and method of use for liposome encapsulated compounds for neutron capture tumor therapy. However, these liposomes were loaded with stable elements (e.g. boron), that become radioactive only after activation.

In a theoretical study, Kostarelos et al., analyzed the therapeutic potential of liposomes labeled with one of the radionuclides $^{131}$I, $^{67}$Cu, $^{188}$Re or $^{211}$At, but chemical procedures for the preparation of the labeled liposomes were not suggested [Kostarelos et al., J Liposome Res, 9:407-424, 1999].

Only a few radiopharmaceuticals based on radioactive copper isotopes are discovered and available today. Examples are $^{60}$Cu-ATSM as hypoxia marker, and $^{64}$Cu-ATSM and $^{64}$Cu-PTSM, which are suggested as potential agents for tumor therapy. Further classes of substances are copper-labeled peptides and antibodies in which the radioactive copper is linked to the biomolecule via a bifunctional chelator. There are no liposome compositions loaded with copper available for use as radiopharmaceuticals.

Several research groups have measured the permeability of anions and cations through lipid bilayers without the use of ionophores.

It is known in the field that the low ion permeability of phospholipid bilayers such as liposome compositions [Paula et al., Biophys. J., 74:319-327, 1998; Hauser et al., Nature, 239:342-344, 1972; Ceh et al., J. Phys. Chem. B, 102:3036-3043, 1998; Mills et al., Biochim. Biophys. Acta, 1716:77-96, 2005; Papahadjopoulos et al., Biochim. Biophys. Acta, 266: 561-583, 1971; Puskin, J. Membrane Biol, 35:39-55, 1977] leads to highly unfavorable loading kinetics for charged ion species. Therefore it is common practice to use an ionophore to increase trans-bilayer diffusion rates, and thereby improve or increase the loading of monovalent, divalent and trivalent cations into nanoparticles such as liposomes.

The patent application WO2006/043083 describes a method for loading of radionuclides, which involves ionophores and chelators. It is mentioned in the application that a chelator may be an ionophore.

The patent application WO03/041682 discloses liposomes enclosing biological agents. It is disclosed in the application that ion-gradients, ionophores, pH gradients and metal complexation procedures can be used for active loading of liposomes with biological agents. The application does not disclose a method for loading of nanoparticles with metal entities wherein an osmotic gradient is used to increase the loading efficiency or loading rate.

There is a need in the technical field of diagnostic applications to provide various liposome compositions that are useful for delivery of a variety of compounds, for example radiodiagnostic and imaging entities useful for PET.

SUMMARY OF INVENTION

The present invention relates to a novel and improved method for preparation of metal entities and/or radionuclides encapsulated within liposome compositions or nanoparticles. Contrary to what is common general knowledge in the field, the inventors have found that loading of metal entities and/or radionuclides is efficient without the use of ionophores. Thus, in the new and inventive methods according to the present invention, the metal entities or radionuclides are loaded into the nanoparticles without the use of an ionophore as a transporting molecule.

Further, the presence of an osmotic stress on the membrane of the nanoparticles of the present invention has been found by the inventors to improve the loading step of metal entities/radionuclides into the interior of the nanoparticles. The positron-emitter $^{64}$Cu is used as a model nuclide representing the chemical properties of all copper isotopes.

The methods for preparation of a nanoparticle composition loaded with metal entities wherein said methods do not involve the use of ionophore according to the present invention comprise steps of:

a. Providing a nanoparticle composition comprising a vesicle forming component and an agent-entrapping component enclosed by said vesicle forming component;

b. Entrapping (loading) the metal entities within the interior of the nanoparticle composition by enabling transfer of cation metal entities across a membrane formed by the vesicle forming component by incubation of the nanoparticle composition in a solution comprising the metal entities.

Wherein said entrapping step involving incubation is understood as the loading of metal entities into the nanoparticle, such as the liposome.

According to the present invention, the loading efficiency or entrapment of radionuclide is greater than 10%. Such a loading efficiency can be in the range of 10% to 100%, preferably 80% to 100%, more preferably in the range of 95% to 100%.

According to one embodiment of the present invention, the incubation temperature is lower than 100° C., such as for example in the range of 10° C. to 80° C., such as 22° C. to 80° C., or such as 30° C. to 80° C.

The incubation time according to the present invention is a time period shorter than 48 hours, such as between 1 min to 240 min, preferably between 1 min to 120 min and more preferably between 1 min to 60 min.

Metal entities according to the present invention may comprise or consist of one or more radionuclides selected from the group consisting of Copper ($^{61}$Cu, $^{64}$Cu, and $^{67}$Cu), Indium ($^{111}$In), Technetium ($^{99m}$Tc), Rhenium ($^{188}$Re), Gallium ($^{67}$Ga, $^{68}$Ga), Lutetium ($^{177}$Lu), Actinium ($^{225}$Ac), Yttrium ($^{90}$Y), Antimony ($^{119}$Sb), Tin ($^{117}$Sn, $^{113}$Sn), Dysprosium ($^{159}$Dy), Cobalt ($^{56}$Co), Iron ($^{59}$Fe), Ruthenium ($^{97}$Ru, $^{103}$Ru), Palladium ($^{103}$Pd), Cadmium ($^{115}$Cd), Tellurium ($^{118}$Te, $^{123}$Te), Barium ($^{131}$Ba, $^{140}$Ba), Gadolinium ($^{149}$Gd, $^{151}$Gd), Terbium ($^{160}$Tb), Gold ($^{198}$Au, $^{199}$Au), Lanthanum ($^{140}$La), and Radium ($^{223}$Ra, $^{224}$Ra).

Metal entities according to the present invention may also comprise one or more metal entities selected from the group of Gd, Dy, Ti, Cr, Mn, Fe, Co, Ni including divalent or trivalent ions thereof.

In one embodiment of the present invention, the method for preparation of nanoparticles involves a step wherein there is a difference in osmotic pressure between the exterior of the nanoparticles and the interior of the nanoparticles during incubation, for example a difference of 5-800 mOsm/L, or preferably a difference of 5-100 mOsm/L.

The vesicle-forming component according to the present invention comprises one or more of the compounds selected from the group consisting of phospholipids, pegylated phospholipids and cholesterol, for example one or more amphiphatic compounds selected from the group of HSPC, DSPC, DPPC, POPC, CHOL, DSPE-PEG-2000, DSPE-PEG-2000-RGD and DSPE-PEG-2000-TATE.

Agent-entrapping components according to the present invention are selected from the group consisting of chelators, reducing agents and agents that form low solubility salts with said radionuclides, for example chelators selected from the group consisting of 1,4,7,10-tetraazacyclododecane-1,4,7,10-tetraacetic acid (DOTA), 1,4,8,11-15 tetraazacyclotetradecane-1,4,8,11-tetraacetic acid (TETA), 1,4,7,10-tetraazacyclododecane-1,4,7,10-tetra(methanephosphonic acid) (DOTP), cyclam and cyclen.

The interior pH of the nanoparticles according to the present invention is within the range of 4 to 8.5, such as 4.0 to 4.5, for example 4.5 to 5.0, such as 5.0 to 5.5 for example 5.5 to 6.0, such as 6.0 to 6.5, for example 6.5 to 7.0, such as 7.0 to 7.5, for example 7.5 to 8.0, such as 8.0 to 8.5.

The stability of the radiolabeled nanoparticles provided by the present invention is such that less than 20% leakage of radioactivity is observed for example less than 15% leakage, such as less than 12% leakage, for example less than 10% leakage, such as less than 8% leakage, for example less than 6% leakage, such as less than 4% leakage, for example less than 3% leakage, such as less than 2% leakage, for example less than 1% leakage.

The present invention further provides kits of parts comprising:
a. A nanoparticle composition comprising i) a vesicle forming component, and ii) an agent-entrapping component enclosed by the vesicle forming component; and
b. A composition containing a metal entity for loading into the nanoparticle, Further, the present invention provides a nanoparticle composition loaded with metal entities comprising:

i. a vesicle forming component,
ii. an agent-entrapping component enclosed by said vesicle-forming component;
iii. a metal entity entrapped on the interior side of the nanoparticle composition.

In a particular embodiment of the present invention, the interior pH of the nanoparticle is within the range of 6 to 8.5, such as 6.0 to 6.5, for example 6.5 to 7.0, such as 7.0 to 7.5, for example 7.5 to 8.0, such as 8.0 to 8.5.

The present invention further provides nanoparticle compositions for use in a method for treating, monitoring or diagnosis in a subject in need, such as for example in an imaging method which may be selected from positron emission tomography (PET) scanning or single photon emission computed tomography (SPECT) scanning and magnetic resonance imaging (MRI).

The present invention further provides nanoparticle compositions prepared by the methods as disclosed by the invention.

Open squares denote Cu(II) standard curve in HEPES buffer, the cross denotes HEPES 10 mM, 150 mM NaNO$_3$, pH 6.8, the open circle denotes unloaded liposomes and the closed circle denotes loaded liposomes.

Figure 5:

FIG. 5: Structure of 1,2-Di-O-Hexadecyl-sn-Glycero-3-phosphocholine (1,2-Di-O-DPPC).

Figure 6:
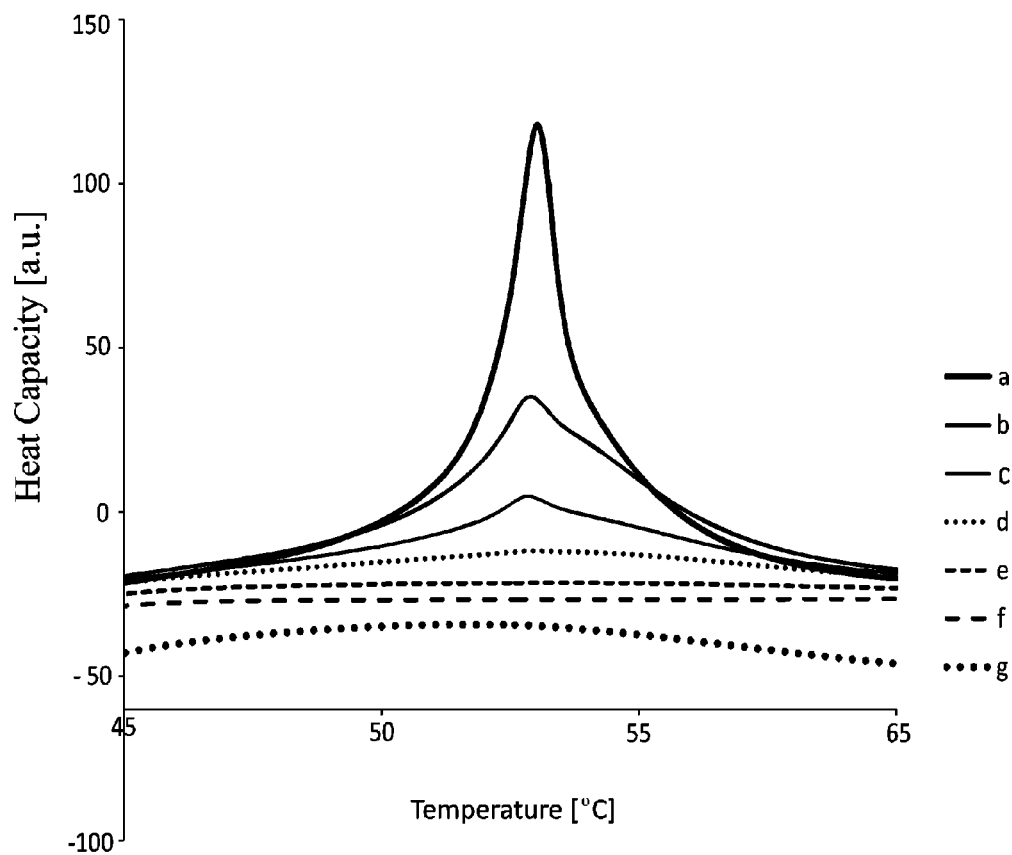

FIG. 6: Differential scanning calorimetry (DSC) scan of DSPC/CHOL/DSPE-PEG$_{2000}$ dispersion in HEPES buffer when mixtures containing 10 mol % DSPE-PEG$_{2000}$ and a) 20 mol % cholesterol and 70 mol % DSPC, b) 25 mol % cholesterol and 65 mol % DSPC c) 30 mol % cholesterol and 60 mol %, d) 35 mol % cholesterol and 55 mol % DSPC, e) 40 mol % cholesterol and 50 mol % DSPC, f) 50 mol % cholesterol and 40 mol % DSPC and g) Purified chelator-containing (10 mM DOTA) liposomes consisting of DSPC/CHOL/DSPE-PEG$_{2000}$ in the molar ratio 50:40:10.

Figure 7:
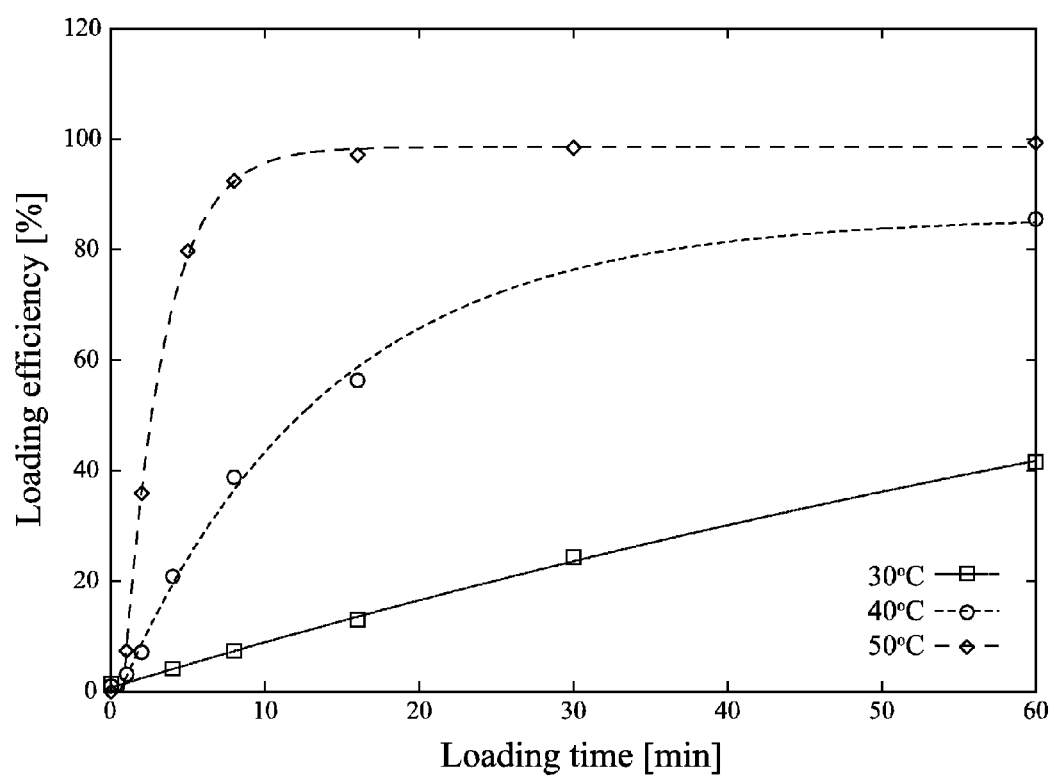

FIG. 7: $^{64}CU^{2+}$ loading efficiency into chelator containing liposomes without using ionophore as function of time at three different temperatures (50° C., 40° C. and 30° C.). The liposomes consist of DSPC/CHOL/DSPE-PEG$_{2000}$ in the molar ratio 50:40:10. The difference between the internal and external osmolarity of the liposomes was, $\Delta$(mOsm/L)=+75 (higher internal osmolarity). The ratio between the interior $^{64}$Cu-DOTA complex and the un-encapsulated or non-complexed free $^{64}CU^{2+}$ is measured as $^{64}$Cu-loading efficiency (%) using radio-thin layer chromatography (radio-TLC).

Figure 8:
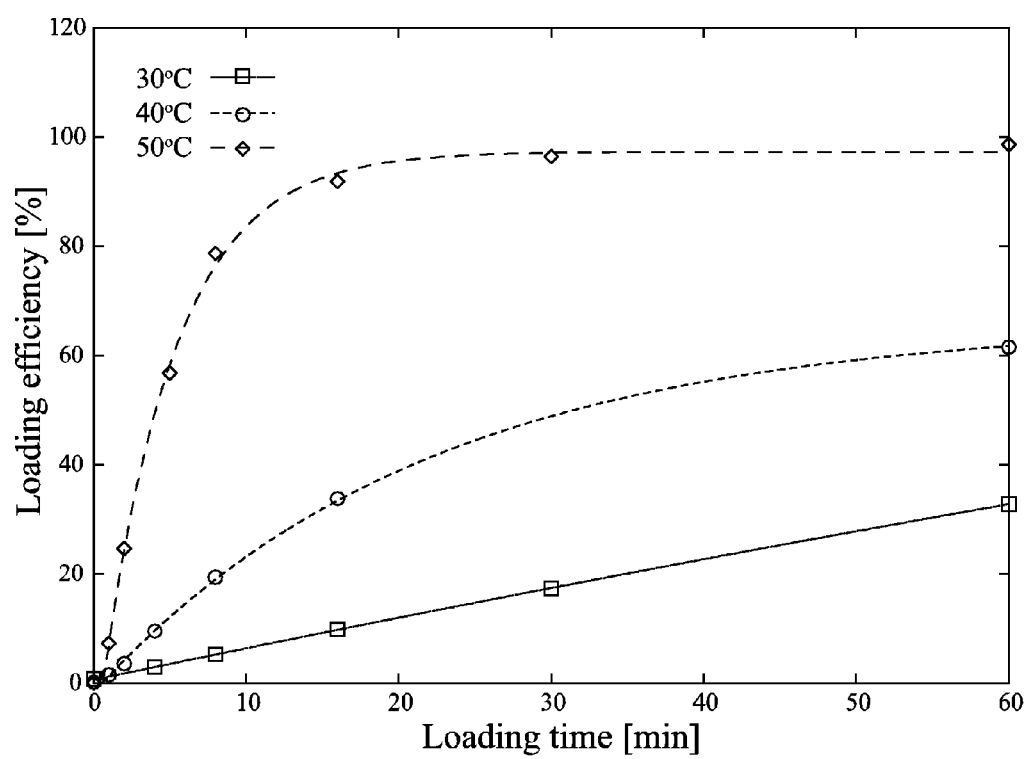

FIG. 8: $^{64}CU^{2+}$ loading efficiency into chelator-containing liposomes without using ionophore as function of time at three different temperatures (50° C., 40° C. and 30° C.). The liposomes consist of DSPC/CHOL/DSPE-PEG$_{2000}$ in the molar ratio 50:40:10 and with equal intra- and extra-liposomal osmolarties. The ratio between the interior $^{64}$Cu-DOTA complex and the un-encapsulated or non-complexed free $^{64}CU^{2+}$ is measured as $^{64}$Cu-loading efficiency (%) using radio-TLC.

DEFINITIONS

With the term "vesicle", as used herein, we refer to an entity which is characterized by the presence of an internal void. Preferred vesicles are formulated from lipids, including various amphiphatic components described herein.

In various aspects the term "nanoparticles", as used herein, are liposomes, polymersomes or other lipid or polymer shell structures that constitute a membrane in its broadest term surrounding a hydrous core.

With the term "chelator" and "chelating-agent" as used herein interchangeably, we intend chemical moieties, agents, compounds, or molecules characterized by the presence of polar groups able to form a complex containing more than one coordinate bond with a transition metal or another entity. A chelator according to the present invention is a water soluble and/or non-lipophilic agent, and is thus not the same as a "lipophilic chelator" used for transportation of metal entities across lipophilic membranes such as vesicles formed by lipids.

With the term "metal entity" as used herein we intend a metal ion or a radionuclide, the latter used herein interchangeably with the term radioisotope.

With the term "phosphatide" we intend a phospholipid comprising a glycerol component.

With the term "amphiphatic" we intend a molecule which contains both polar and nonpolar regions.

With the term "binding affinity" and "affinity" as used herein interchangeably, we refer to the level of attraction between molecular entities. Affinity can be expressed quantitatively as the dissociation constant or its inverse, the association constant. In the context of this invention the affinity of a chelator or another agent-entrapping component can relate to the binding affinity of the chelator DOTA for a transition metal ion or another metal entity, for example, Cu(II) or Cu(I).

With the term "entrapped agent" we intend a metal isotope, which may be a radionuclide or a non-radioactive isotope, entrapped within a liposome composition or a nanoparticle composition as herein described.

With the term "agent-entrapping" as used herein, we refer to any compound, without limitation, capable of trapping a metal ion or a radionuclide inside a liposome composition. Preferred agent-entrapping components are chelating-agents, substances that have the ability to reduce other substances, referred to a reducing agent, or substances that form low solubility salts with radionuclides or metal entities.

With the terms "loading", "encapsulation", or "entrapment" as used herein, are referred to an incorporation of radionuclides or metal entities into the interior of nanoparticle compositions. In the methods of the present invention, this incorporation is done by incubation of nanoparticle compositions with a solution comprising radionuclides or metal entities.

With the terms "loading efficiency", "entrapment efficiency" or "encapsulation efficiency" as used herein interchangeably, is referred to the fraction of incorporation of radionuclides or metal entities into the interior of nanoparticle compositions expressed as a percentage of the total amount of radionuclide or metal entity used in the preparation.

With the term "encapsulation stability", "storage stability" or "serum stability" is referred to a stability test of the nanoparticle composition to measure the degree of leakage and/or release of the entrapped agent inside the nanoparticle composition.

With the term "radiolabeled complex" and the like, we refer to a chelating agent and a radionuclide that form a complex.

With the term "targeting moiety" as used herein we intend saccharides, oligosaccharides, vitamins, peptides, proteins, antibodies and affibodies and other receptor binding ligands characterized by being attached to the nanoparticle surface through a lipid or polymer component for delivering the nanoparticles to a higher degree to the target site or into target cells.

The terms "drug", "medicament", "agent", or "pharmaceutical compound" as used herein include, biologically, physiologically, or pharmacologically active substances that act locally or systemically in the human or animal body.

The terms "treating", "treatment" and "therapy" as used herein refer equally to curative therapy, prophylactic or preventative therapy and ameliorating therapy. The term includes an approach for obtaining beneficial or desired physiological results, which may be established clinically. For purposes of this invention, beneficial or desired clinical results include, but are not limited to, alleviation of symptoms, diminishment of extent of disease, stabilized (i.e., not worsening) condition, delay or slowing of progression or worsening of condition/symptoms, amelioration or palliation of the condition or symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering compositions of the present invention.

The term "osmolarity" as used herein refers to the measure of solute concentration, defined as the number of osmoles (Osm) of solute per liter (L) of solution (Osm/L).

DETAILED DESCRIPTION OF THE INVENTION

The present invention relates to a novel and improved method for preparation of metal entities and/or radionuclides encapsulated within liposome compositions or nanoparticles which is based on an efficient loading temperature and favorable liposomal compositions. Further, the presence of an osmotic stress of the membrane of the nanoparticles of the present invention has been found by the inventors to improve the loading step of metal entities/radionuclides into the interior of the nanoparticles.

The inventors have surprisingly found a method for loading charged species (ions) into nanoparticles without adding ionophores to enhance trans-membrane diffusion rates. Thus, the present invention discloses a novel method for fast entrapment of radionuclides (e.g. monovalent, divalent and trivalent cations) into liposome compositions without adding any lipophilic ionophores or any other carrier.

During the last 40 years lipophilic ionophores or complexes have been used for enhancing the efficiency of encapsulating radionuclides (e.g. $^{111}In^{3+}$, $^{177}Lu^{3+}$, $^{67/68}Ga^{2+}$, $^{99m}TcO_4^-$) in nanoparticles for in vivo scintigraphic imaging and internal radiotherapeutic applications. The encapsulation (or loading) efficiencies using lipophilic ionophores have reached high levels as 90-95%. The present invention relates to a new method that does not use any lipophilic ionophores or other metal carriers and can obtain similar or even higher loading efficiencies of radionuclides into liposome compositions. A preparation method for loading metal entities and/or radionuclides into nanoparticles which does not involve the use of ionophore has several advantages. Ionophores may be toxic to mammals, in particular to human beings. Therefore, nanoparticles prepared with the use of an ionophore will need to undergo extensive toxicity testing prior to regulatory approval. Furthermore, such nanoparticles will need to be purified prior to use to remove as much ionophore as possible and the extent of such purification will need to be monitored to ensure that the level of ionophore is below a certain threshold.

Manufacture of nanoparticles of the present invention is done easily with few components and without the need for extensive purification. When the nanoparticles of the present invention are administered to patients, the risks of side-effects such as toxicity or other side-effects are reduced. Further, the novel preparation method allow for an interior pH range of the nanoparticles which improve the stability of the nanoparticles. In this way, the use of the nanoparticles, methods or kits of part of the present invention is facilitated since shelf-life, storage requirements and other aspects related to the use of the present invention is improved compared to the prior art.

Also, while lipophilic ionophores are finding their usefulness for enhancing the efficiency of encapsulation of radionuclides e.g. cations into liposomes, the very lipophilic ionophores can also facilitate the release of entrapped radionuclides from the liposomes. A release of entrapped materials prematurely can result in not only an erroneous estimation of distribution of liposomes in vivo, but also a loss of quality in the diagnostic images.

Further, the present invention solves a need in the technical field of diagnostic applications by providing nanoparticles for delivery of metal entities to tissues with pathological conditions associated with leaky blood vessels such as inflammatory sites or cancerous tissues.

Loading Efficiency and Loading Rate

The loading efficiency of loading methods for liposomes can be measured by use of conventional methods in the art including ion-exchange chromatography, radio thin layer chromatography (radio-TLC), dialysis, or size exclusion chromatography (SEC) which can separate free radioactive metal ions or free radiolabeled complexes from liposome encapsulated radionuclides. When using SEC, the amount of radioactivity retained in liposomes compared to the amount of free radioactive metal ions or free radiolabeled complexes can be determined by monitoring the elution profile during SEC and measuring the radioactivity with a radioactivity detector, or measuring the concentration of the metal entity using inductively coupled plasma mass spectrometry (ICP-MS), inductively coupled plasma atomic emission spectroscopy (ICP-AES) or inductively coupled plasma optical emission spectrometry (ICP-OES). The radioactivity measured in the eluted fractions containing liposomes compared to eluted fractions not containing liposomes can be used to determine the loading efficiency by calculating the percentage of radioactivity retained in liposomes. Likewise, the amount of radioactivity bound in liposomes can be compared to the amount of radioactivity not entrapped in liposomes to obtain a measure of the loading efficiency when using other conventional methods known in the art.

The methods of the present invention ensure that a high amount of the radionuclides used in preparation will be entrapped within the nanoparticle. In one embodiment of the present method the efficiency of loading is higher than 10%, such as in the range of 10%-100%, such as higher than 15%, such as higher than 20%, such as higher than 25%, such as higher than 30%, such as higher than 35%, for example higher than 40%, such as higher than 50%, for example higher than 60%, such as higher than 65%, for example higher than 70%, such as higher than 75%, for example higher than 80%, such as higher than 85%, for example higher than 90%, such as higher than 95%, or such as higher than 96%, or such as higher than 97%, or such as higher than 98%, or such as higher than 99% or such as higher than 99.5% or such as higher than 99.9%. In another embodiment of the present invention the efficiency of loading when using the methods of the present invention is higher than 30% when assayed using size exclusion chromatography (SEC, described in examples), ion-exchange chromatography or dialysis, such as 30% to 100%, including 55% to 100% loading efficiency, 80% to 100% loading efficiency, and 95% to 100% loading efficiency.

Preferably, the efficiency of loading of the methods according to the present invention is in the range of 55% to 100% such as in the range of 80% to 100%, more preferably in the range of 95% to 100%, such as between 95% to 97%, or such as between 97% to 99.9% loading efficiency.

The Loading Rate:

The loading of metals ions into liposomes can be divided into several steps including: (i) binding/coordination/adsorption of the ion to the lipid membrane, (ii) trans-membrane ion diffusion and (iii) binding of ions to the chelator. In the methods of the present invention, the lipid and chelator may be in large excess compared to the metal entities which may be for example, but not limited to, $^{64}Cu^{2+}$. In the example of $^{64}Cu^{2+}$ the kinetics thus only depends on the $^{64}Cu^{2+}$ concentration. The rate of coordination/binding of $Cu^{2+}$ to the membrane is rapid (likely to be diffusion limited) and binding of $Cu^{2+}$ to the chelator (for example DOTA) occurs on timescale of seconds and can be verified by radio-TLC, or other conventional methods of the art. Since binding of metal entities to the membrane is fast, trans-membrane ion diffusion is the most probable rate limiting step.

In general, the rate of trans-membrane diffusion will depend on the concentration gradient of the transported entity (according to Ficks $1^{st}$ law), the membrane phase state (gel, fluid or liquid-ordered) and physicochemical (hydrophilicity vs. hydrophobicity) properties of the transported entity. These arguments substantiate the first order equation (equation 1) presented below, which is here shown for $^{64}Cu^{2+}$, but is usable for other metal entities as well. The loading kinetics (example shown in FIG. 7-8) can be characterized by the equation $$\% \text{ load} = \frac{A_{Cu-chelator}}{A_{Cu} + A_{Cu-chelator} + A_{Cu(ionophore)}} = a(1 - be^{-ct}) \quad \text{(equation 1)}$$

where $A_{cu}$, $A_{Cu-chelator}$ and $A_{Cu(ionophore)}$ denote the TLC activity of the $^{64}CU^{2+}$, $^{64}$Cu-Chelator and $^{64}$Cu-ionophore specie. The fitting parameter a, describes the plateau level (a ~100% if loading proceeds according to $1^{st}$ order kinetics), b describes offset and uncertainty in t (b=1 when offset and uncertainties in t are small) and c describes the loading rate. By fitting of equation 1, each loading profile can be characterized by:
(i) the initial velocity:

$$v_{ini} = a \cdot b \cdot c \quad \text{(equation 2),}$$

(ii) the time required to reach 95% loading:

$$t_{(95\%)} = -\ln((1-(95\%)/a)/b)/c \quad \text{(equation 3),}$$

and (iii) the degree of loading reached at 60 min (% $\text{load}_{1h}$). The latter is directly comparable to the loading degree achieved using the method based on SEC (see for example results in the examples and presented in FIG. 3 and Tables 1, 2, 6 and 7).

The first order rate constant (c) depends on different parameters such as temperature and osmolarity (see FIG. 7-8) (see next section) at which the loading is conducted. The initial velocity ($v_{ini}$), $t_{(95\%)}$ and % $\text{load}_{1h}$ are given in Table 8 for a set of loading conditions.

The loading rate of methods of the present invention can also be described by the parameters initial velocity, the time required to reach 95% loading and the degree of loading reached at 60 min.

Thus in one embodiment of the present invention, the initial velocity is in the range of 0.5%/min to 100%/min, preferably in the range of 3%/min to 100%/min and more preferably in the range of 23%/min to 100%/min.

In one embodiment of the present invention, the time required to reach 95% loading is in the range of 0 minutes to 360 minutes, such as 1 minutes to 240 minutes, preferably in the range of 5 minutes to 240 minutes, such as in 5 minutes to 20 minutes, or such as in the range of 9 minutes to 18 minutes.

In one embodiment of the present invention, the degree of loading reached after 60 minutes is in the range of 10% to 100%, more preferably in the range of 55% to 100%, such as the range of 80% to 100%, and even more preferably in the range of 95% to 100%, such as 95% to 99.9%.

Methods for loading of nanoparticles (such as liposomes) can be compared by measuring parameters such as loading efficiency and loading rates described by the parameters initial velocity, the time required to reach 95% loading and the degree of loading reached at 60 min. Thus, the significance of the contribution of ionophores to the above mentioned loading efficiency or loading rate can be determined by the methods disclosed herein.

The present invention provides a method for preparation of nanoparticles (such as liposomes) loaded with metal entities, wherein ionophores are not used for loading of the nanoparticles, or wherein one or more ionophores are present in such small amounts that they do not contribute significantly to the loading rate or the loading efficiency of the loading, since such methods essentially use the same mechanisms for loading as provided by the present invention. Thus, such methods can include methods wherein one or more ionophores are present in such amounts that there is no significant increase in loading efficiency and/or loading rate as determined by the parameters selected from the group of initial velocity, time required to reach 95% loading, degree of loading reached at 60 min. Significance of differences in loading rate or loading efficiency can be calculated by using conventional statistical methods, such as for example Student t-test.

Nano-Particles

According to the embodiments of the invention, the liposome composition is a micro-sized or a nano-sized particle that comprises a vesicle forming component and an agent-entrapping component. The vesicle forming components form an enclosed barrier of the particle. The agent-entrapping component may have at least one chemical moiety that contains one or more negatively charged groups or is capable of trapping ions. The agent-entrapping component can furthermore be a reducing agent.

The agent-entrapping component interacts with an encapsulated agent, such as a metal entity comprising radio-diagnostic or radio-therapeutic agent, by electrostatic interaction, to form a stable complex or low soluble salt, or by reduction to form a precipitate. The stabilization of the encapsulated agent, such as the radio-diagnostic or radio-therapeutic agent, prevents or minimizes the release of the agent from the vesicles in the blood circulation.

Agent entrapping components may further have at least one chemical moiety that contains one or more charged groups which may be negatively or positively charged or is capable of trapping ions.

Metal Entities

Nanoparticles according to the present invention comprise metal entities. Metal entities according to the present invention may be selected from the metals known for a person skilled in the art and including any of the existing oxidation states for the metal, such as monovalent cations, divalent cations, trivalent cations, tetravalent cations, pentavalent cations, hexavalent cations and heptavalent cations.

In one embodiment of the present invention, the metal entities are cations selected from the group of monovalent cations, divalent cations, trivalent cations, tetravalent cations, pentavalent cations, hexavalent cations and heptavalent cations, wherein divalent and trivalent cations are preferred.

In one embodiment of the present invention, the metal entity is copper such as Cu(I) or Cu(II).

The nanoparticles of the present invention comprise entrapped metal entities, which may comprise or consist of metal radionuclides selected from the group of isotopes consisting of Copper ($^{61}$Cu, $^{64}$Cu, and $^{67}$Cu), Indium ($^{111}$In) Technetium ($^{99m}$Tc), Rhenium ($^{188}$Re), Gallium ($^{67}$Ga, $^{68}$Ga), Lutetium ($^{177}$Lu), Actinium ($^{225}$Ac), Yttrium ($^{90}$Y), Antimony ($^{119}$Sb) Tin ($^{117}$Sn, $^{113}$Sn) Dysprosium ($^{159}$Dy), Cobalt ($^{56}$Co), Iron ($^{59}$Fe), Ruthenium ($^{97}$Ru, $^{103}$Ru), Palladium ($^{103}$Pd), Cadmium ($^{115}$Cd), Tellurium ($^{118}$Te, $^{123}$Te), Barium ($^{131}$Ba, $^{140}$Ba), Gadolinium ($^{149}$Gd, $^{151}$Gd), Terbium ($^{160}$Tb), Gold ($^{198}$Au, $^{199}$Au) Lanthanum ($^{140}$La), and Radium ($^{223}$Ra, $^{224}$Ra), wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations.

In another embodiment, the entrapped metal entities comprise isotopes selected from the group of Rhenium ($^{86}$Re), Strontium ($^{89}$Sr), Samarium ($^{153}$Sm), Ytterbium ($^{169}$Yb), Thallium ($^{201}$Tl), Astatine ($^{211}$At), wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations.

In yet another embodiment, the entrapped metal entities comprise isotopes selected from the group of Copper ($^{61}$Cu, $^{64}$Cu, and $^{67}$Cu), Indium ($^{111}$In), Technetium ($^{99m}$Tc), Rhenium ($^{188}$Re), Gallium ($^{67}$Ga, $^{68}$Ga), Actinium ($^{225}$Ac), Yttrium ($^{90}$Y), Antimony ($^{119}$Sb), and Lutetium ($^{177}$Lu), wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations.

In yet another embodiment of the present invention, one or more of the entrapped metal entities are selected from the group of metals which may be used for magnetic resonance imaging (MRI) selected from the group of consisting of Gd, Dy, Ti, Cr, Mn, Fe, Fe, Co, Ni. Said metal entity may appear in any of the existing oxidation states for the metal. These oxidation states include monovalent cations, divalent cations, trivalent cations, tetravalent cations, pentavalent cations, hexavalent cations and heptavalent cations.

In a preferred embodiment of the present invention, one or more of the entrapped metal entities are selected from the group of consisting of Gd(III), Dy(III), Ti(II), Cr(III), Mn(II), Fe(II), Fe(III), Co(II), Ni(II).

Combinations of radionuclides are useful for simultaneous monitoring/imaging and treatment of various diseases such as cancer, and/or for monitoring by use of several different imaging methods. Radionuclides and combinations of radionuclides may emit one or more types of radiation such as alpha particles, beta+ particles, beta– particles, auger electrons or gamma-rays. Combinations of radionuclides may further allow for one or more types of imaging and/or radiation therapy. Thus, in another embodiment, this invention relates to vesicles and methods for their preparation, wherein the vesicles comprise metal entities comprising two or more radionuclides, selected from the group of Copper ($^{61}$Cu, $^{64}$Cu, and $^{67}$Cu), Indium ($^{111}$In), Technetium ($^{99m}$Tc), Rhenium ($^{186}$Re, $^{188}$Re), Gallium ($^{67}$Ga, $^{68}$Ga), Strontium ($^{89}$Sr), Samarium ($^{153}$Sm), Ytterbium ($^{169}$Yb), Thallium ($^{201}$Tl), Astatine ($^{211}$At), Lutetium ($^{177}$Lu), Actinium ($^{225}$Ac), Yttrium ($^{90}$Y), Antimony ($^{119}$Sb), Tin ($^{117}$Sn, $^{113}$Sn), Dysprosium ($^{159}$Dy), Cobalt ($^{56}$Co), Iron ($^{59}$Fe), Ruthenium ($^{97}$Ru, $^{103}$Ru), Palladium ($^{103}$Pd), Cadmium ($^{115}$Cd), Tellurium ($^{118}$Te, $^{123}$Te), Barium ($^{131}$Ba, $^{140}$Ba), Gadolinium ($^{149}$Gd, $^{151}$Gd), Terbium ($^{160}$Tb), Gold ($^{198}$Au, $^{199}$Au), Lanthanum ($^{140}$La), and Radium ($^{223}$Ra, $^{224}$Ra) wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations.

In a further embodiment, combinations of metal entities may include one or more metals and one or more radionuclides which further allow for one or more types of imaging and/or radiation therapy. Thus, in another embodiment, this invention relates to vesicles and methods for their preparation, wherein the vesicles comprise metal entities selected from the group of Gd, Dy, Ti, Cr, Mn, Fe, Fe, Co, Ni in any of the existing oxidation states for the metal, with radionuclides selected from the group of the group of Copper ($^{61}$Cu, $^{64}$Cu, and $^{67}$Cu), Indium ($^{111}$In), Technetium ($^{99m}$Tc), Rhenium $^{186}$Re, $^{188}$Re), Gallium ($^{67}$Ga, $^{68}$Ga), Strontium ($^{89}$Sr), Samarium ($^{153}$Sm), Ytterbium ($^{169}$Yb), Thallium ($^{201}$Tl), Astatine ($^{211}$At), Lutetium ($^{177}$Lu), Actinium ($^{225}$Ac), Yttrium ($^{90}$Y), Antimony ($^{119}$Sb), Tin ($^{117}$Sn, $^{113}$Sn), Dysprosium ($^{159}$Dy), Cobalt ($^{56}$Co), Iron ($^{59}$Fe), Ruthenium ($^{97}$Ru, $^{103}$Ru), Palladium ($^{103}$Pd), Cadmium ($^{115}$Cd), Tellurium ($^{118}$Te, $^{123}$Te), Barium ($^{131}$Ba, $^{140}$Ba), Gadolinium ($^{149}$Gd, $^{151}$Gd), Terbium ($^{160}$Tb), Gold ($^{198}$Au, $^{199}$Au), Lanthanum ($^{140}$La), and Radium ($^{223}$Ra, $^{224}$Ra) wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations.

Thus according to the present invention, nanoparticle compositions such as vesicles may comprise one or more combinations selected from the group of $^{64}$Cu and Gd(III), $^{64}$Cu and Dy(III), $^{64}$Cu and Ti(II), $^{64}$Cu and Cr(III), $^{64}$Cu and Mn(II), $^{64}$Cu and Fe(II), $^{64}$Cu and Fe(III), $^{64}$Cu and Co(II), $^{64}$Cu and Ni(II), $^{68}$Ga and Gd(III), $^{68}$Ga and Dy(III), $^{68}$Ga and Ti(II), $^{68}$Ga and Cr(III), $^{68}$Ga and Mn(II), $^{68}$Ga and Fe(II), $^{68}$Ga and Fe(III), $^{68}$Ga and Co(II), $^{68}$Ga and Ni(II), $^{111}$In and Gd(III), $^{111}$In and Dy(III), $^{111}$In and Ti(II), $^{111}$In and Cr(III), $^{111}$In and Mn(II), $^{111}$In and Fe(II), $^{111}$In and Fe(III), $^{111}$In and Co(II), $^{111}$In and Ni(II), $^{99m}$Tc and Gd(III), $^{99m}$Tc and Dy(III), $^{99m}$Tc and Ti(II), $^{99m}$Tc and Cr(III), $^{99m}$Tc and Mn(II), $^{99m}$Tc and Fe(II), $^{99m}$Tc and Fe(III), $^{99m}$Tc and Co(II), $^{99m}$Tc and Ni(II), $^{177}$Lu and Gd(III), $^{177}$Lu and Dy(III), $^{177}$Lu and Ti(II), $^{177}$Lu and Cr(III), $^{177}$Lu and Mn(II), $^{177}$Lu and Fe(II), $^{177}$Lu and Fe(III), $^{177}$Lu and Co(II), $^{177}$Lu and Ni(II), $^{67}$Ga and Gd(III), $^{67}$Ga and Dy(III), $^{67}$Ga and Ti(II), $^{67}$Ga and Cr(III), $^{67}$Ga and Mn(II), $^{67}$Ga and Fe(II), $^{67}$Ga and Fe(III), $^{67}$Ga and Co(II), $^{67}$Ga and Ni(II), $^{201}$Tl and Gd(III), $^{201}$Tl and Dy(III), $^{201}$Tl and Ti(II), $^{201}$Tl and Cr(III), $^{201}$Tl and Mn(II), $^{201}$Tl and Fe(II), $^{201}$Tl and Fe(III), $^{201}$Tl and Co(II), $^{201}$Tl and Ni(II), $^{90}$Y and Gd(III), $^{90}$Y and Dy(III), $^{90}$Y and Ti(II), $^{90}$Y and Cr(III), $^{90}$Y and Mn(II), $^{90}$Y and Fe(II), $^{90}$Y and Fe(III), $^{90}$Y and Co(II) and $^{90}$Y and Ni(II), wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations.

In a preferred embodiment, nanoparticle compositions such as vesicles may comprise one or more combinations of metal entities selected from the group consisting of $^{64}$Cu and Gd(III), $^{64}$Cu and Dy(III), $^{64}$Cu and Ti(II), $^{64}$Cu and Cr(III), $^{64}$Cu and Mn(II), $^{64}$Cu and Fe(II), $^{64}$Cu and Fe(III), $^{64}$Cu and Co(II), $^{64}$Cu and Ni(II), $^{68}$Ga and Gd(III), $^{68}$Ga and Dy(III), $^{68}$Ga and Ti(II), $^{68}$Ga and Cr(III), $^{68}$Ga and Mn(II), $^{68}$Ga and Fe(II), $^{68}$Ga and Fe(III), $^{68}$Ga and Co(II), $^{68}$Ga and Ni(II), $^{177}$Lu and Gd(III), $^{177}$Lu and Dy(III), $^{177}$Lu and Ti(II), $^{177}$Lu and Cr(III), $^{177}$Lu and Mn(II), $^{177}$Lu and Fe(II), $^{177}$Lu and Fe(III), $^{177}$Lu and Co(II), $^{177}$Lu and Ni(II) wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations, In an even more preferred embodiment, the nanoparticle compositions such as vesicles may comprise one or more combinations of metal entities selected from the group consisting of $^{64}$Cu and Gd(III), $^{68}$Ga and Gd(III), $^{177}$Lu and Gd(III), $^{111}$In and Gd(III), $^{67}$Ga and Gd(III), $^{90}$Y and Gd(III), wherein the combinations of $^{64}$Cu and Gd(III) and $^{68}$Ga and Gd(III) are most preferred.

Vesicles according to the present invention may comprise a combination of one or more radionuclides for imaging and one or more radionuclides for therapy. Radionuclides for imaging comprise radionuclides such as $^{64}$Cu, $^{61}$Cu, $^{99m}$Tc, $^{68}$Ga, $^{89}$Zr and $^{111}$In.

Radionuclides for therapy comprise radionuclides such as $^{64}$Cu, $^{67}$Cu, $^{111}$In, $^{67}$Ga, $^{186}$Re, $^{188}$Re, $^{89}$Sr, $^{153}$Sm, $^{169}$Yb, $^{201}$Tl, $^{211}$At, $^{177}$Lu, $^{225}$Ac, $^{90}$Y, $^{119}$Sb, $^{117}$Sn, $^{113}$Sn, $^{159}$Dy, $^{56}$Co, $^{59}$Fe, $^{97}$Ru, $^{103}$Ru, $^{103}$Pd, $^{115}$Cd, $^{118}$Te, $^{123}$Te, $^{131}$Ba, $^{140}$Ba, $^{149}$Gd, $^{151}$Gd, $^{160}$Tb, $^{198}$Au, $^{119}$Au, $^{140}$La, $^{223}$Ra and $^{224}$Ra.

In a preferred embodiment of the present invention, the vesicles or nanoparticles comprise two or more radionuclides selected from the group of $^{61}$Cu, $^{64}$Cu, $^{67}$Cu, $^{67}$Ga, $^{68}$Ga, $^{225}$Ac, $^{90}$Y, $^{177}$Lu, $^{186}$Re, $^{188}$Re and $^{119}$Sb.

An even more preferred embodiment of the present invention relates to vesicles or nanoparticles comprising $^{64}$Cu and $^{177}$Lu, or $^{64}$Cu and $^{67}$Cu, or $^{61}$Cu and $^{67}$Cu, or $^{64}$Cu and $^{90}$Y, or $^{64}$Cu and $^{119}$Sb, or $^{64}$Cu and $^{225}$Ac, or $^{64}$Cu and $^{188}$Re, or $^{64}$Cu and $^{186}$Re, or $^{64}$Cu and $^{211}$At, or $^{64}$Cu and $^{67}$Ga, or $^{61}$Cu and $^{90}$Y, or $^{61}$Cu and $^{119}$Sb, or $^{61}$Cu and $^{225}$Ac, or $^{61}$Cu, and $^{188}$Re, or $^{61}$Cu and $^{186}$Re, or $^{61}$Cu and $^{211}$At, or $^{61}$Cu and $^{67}$Ga, or $^{67}$Cu, and $^{177}$Lu, or $^{67}$Cu and $^{90}$Y, or $^{67}$Cu, and $^{119}$Sb, or $^{67}$Cu and $^{225}$Ac, or $^{67}$Cu and $^{188}$Re, or $^{67}$Cu and $^{186}$Re, or $^{67}$Cu and $^{211}$At, or $^{68}$Ga and $^{186}$Re, or $^{68}$Ga and $^{211}$At, or $^{68}$Ga and $^{67}$Cu.

Nanoparticles or vesicles comprising one or more radionuclides according to the present invention may be used for clinical imaging and/or radiotherapy. Clinical imaging includes imaging for diagnosis, monitoring the effects of treatment, or monitoring the location of vesicles used for radiotherapy.

In a preferred embodiment, vesicles or nanoparticles of the present invention comprise a combination of radionuclides useful for combined positron emission tomography (PET) imaging and radiation therapy, such as $^{64}$Cu and $^{177}$Lu, or such as $^{64}$Cu and $^{67}$Cu, or such as $^{61}$Cu and $^{67}$Cu, or such as $^{64}$Cu and $^{90}$Y, or such as $^{64}$Cu and $^{119}$Sb, or such as $^{64}$Cu and $^{225}$AC, or such as $^{64}$Cu and $^{188}$Re, or such as $^{64}$Cu and $^{186}$Re, or such as $^{64}$Cu and $^{211}$At.

In an even more preferred embodiment, vesicles or nanoparticles of the present invention comprise a combination of radionuclides useful for combined positron emission tomography (PET) imaging and radiation therapy, such as $^{64}$Cu and $^{177}$Lu.

According to the present invention, the nanoparticles may comprise one or more isotopes different from copper which may be associated to the inner or outer surface of the nanoparticle composition via a linker molecule such as a chelator. Such isotopes may be selected from the group of Indium ($^{111}$In) Technetium ($^{99m}$Tc), Rhenium ($^{186}$Re, $^{188}$Re), Gallium ($^{67}$Ga, $^{68}$Ga), Strontium ($^{89}$Sr), Samarium ($^{153}$Sm), Ytterbium ($^{169}$Yb), Thallium ($^{201}$Ti), Astatine ($^{211}$At), Lutetium ($^{177}$Lu), Actinium ($^{255}$Ac), Yttrium ($^{90}$Y), Antimony ($^{119}$Sb), Tin ($^{117}$Sn, $^{113}$Sn), Dysprosium ($^{159}$Dy), Cobalt ($^{56}$Co), Iron ($^{59}$Fe), Ruthenium ($^{97}$Ru, $^{103}$Ru), Palladium ($^{103}$Pd), Cadmium ($^{115}$Cd), Tellurium ($^{118}$Te, $^{123}$Te), Barium ($^{131}$Ba, $^{140}$Ba), Gadolinium ($^{149}$Gd, $^{151}$Gd), Terbium ($^{169}$Tb), Gold ($^{198}$Au, $^{199}$Au), Lanthanum ($^{140}$La), Radium ($^{223}$Ra, $^{224}$Ra), Rhenium ($^{186}$Re), Strontium ($^{89}$Sr), Samarium ($^{153}$Sm), Ytterbium ($^{69}$Yb), Thallium ($^{201}$Tl) and Astatine ($^{211}$At), wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations.

According to one embodiment of the present invention, the metal entities can be radionuclides selected from the group consisting of $^{61}$Cu, $^{64}$Cu, $^{67}$Cu, $^{177}$Lu, $^{67}$Ga, $^{68}$Ga, $^{225}$Ac, $^{90}$Y, $^{186}$Re, $^{188}$Re, $^{119}$Sb, and $^{111}$In wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations.

In a preferred embodiment of the present invention, the metal entities are radionuclides selected from the group consisting of $^{61}$Cu, $^{64}$Cu, $^{67}$Cu, $^{111}$In and $^{177}$Lu wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations.

In one embodiment of the present invention, the metal entities are two or more radionuclides selected from the group consisting of $^{64}$Cu and $^{67}$Cu, $^{61}$Cu and $^{67}$Cu, $^{64}$Cu and $^{90}$Y, $^{64}$Cu and $^{119}$Sb, $^{64}$Cu and $^{225}$Ac, $^{64}$Cu and $^{188}$Re, $^{64}$Cu and $^{186}$Re, $^{64}$Cu and $^{211}$At, $^{64}$Cu and $^{67}$Ga, $^{61}$Cu and $^{177}$Lu, $^{61}$Cu and $^{90}$Y, $^{61}$Cu and $^{119}$Sb, $^{61}$Cu and $^{225}$Ac, $^{61}$Cu and $^{90}$Y, $^{188}$Re, $^{61}$Cu and $^{186}$Re, $^{61}$Cu and $^{211}$At, $^{61}$Cu and $^{67}$Ga, $^{67}$Cu and $^{177}$Lu, $^{67}$Cu and $^{90}$Y, $^{67}$Cu and $^{119}$Sb, $^{67}$Cu and $^{225}$Ac, $^{67}$Cu and $^{188}$Re, $^{67}$Cu and $^{186}$Re, $^{67}$Cu and $^{211}$At, $^{68}$Ga and $^{177}$Lu, $^{68}$Ga and $^{90}$Y, $^{68}$Ga and $^{119}$Sb, $^{68}$Ga and $^{225}$Ac, $^{68}$Ga and $^{188}$Re, $^{68}$Ga and $^{186}$Re, $^{68}$Ga and $^{211}$At, and $^{68}$Ga and $^{67}$Cu.

In another embodiment of the present invention, the metal entities are two or more radionuclides selected from the group consisting of Copper ($^{61}$Cu, $^{64}$Cu, and $^{67}$Cu), such as $^{61}$Cu and $^{64}$Cu, or $^{61}$Cu and $^{67}$Cu, or $^{64}$Cu and $^{67}$Cu, or $^{61}$Cu, $^{64}$Cu and $^{67}$Cu.

In one embodiment of the present invention, the metal entities are selected from the groups of metal entities as mentioned herein, wherein the cations $Hg^{2+}$ and $Cu^+$, are excluded.

In a further embodiment of the invention, the radionuclide may also be entrapped within another carrier such as a nanoparticle that is useful in diagnosing and/or treating a cancerous disease and, in general a pathological condition associated with leaky blood vessels or another disease in a subject.

A detailed description of exemplary vesicle forming components and agent-entrapping components for preparing the liposome compositions of the present invention are set forth below.

Vesicle Forming Component

A vesicle forming component is a synthetic or naturally-occurring amphipathic compound which comprises a hydrophilic part and a hydrophobic part. Vesicle forming components include, for example, fatty acids, neutral fats, phosphatides, glycolipids, aliphatic alcohols, and steroids. Additionally, vesicle forming components may further include lipids, diblock and triblock copolymers bolalipids, ceramides, sphingolipids, phospholipids, pegylated phospholipids and cholesterol.

In one embodiment of the present invention, the vesicle forming components allow for a prolonged circulation time of the nanoparticles.

The vesicle forming component of the present invention or the method of the present invention may contain a hydrophilic polymer such as for example a polyethylene glycol (PEG) component or a derivate thereof, or a polysaccharide. In such a case the vesicle forming component is said to be derivatized with the hydrophilic polymer (e.g. PEG) or the polysaccharide. In one embodiment, the polymer enables conjugation of proteins or other receptor affinity molecules to the vesicle forming component derivatized with the polymer. In another embodiment, the attachment of the polymer (e.g. PEG) to the liposome composition, allows for prolonged circulation time within the blood stream. Vesicles comprising PEG chains on their surface are capable of extravasating leaky blood vessels.

Examples of suitable vesicle forming lipids used in the present invention or the method of the present invention include, but are not limited to: phosphatidylcholines such as 1,2-dioleoyl-phosphatidylcholine, 1,2-dipalmitoyl-phosphatidylcholine, 1,2-dimyristoyl-phosphatidylcholine, 1,2-distearoyl-phosphatidylcholine, 1-oleoyl-2-palmitoyl-phosphatidylcholine, 1-oleoyl-2-stearoyl-phosphatidylcholine, 1-palmitoyl-2-oleoyl-phosphatidylcholine and 1-stearoyl-2-oleoyl-phosphatidylcholine; phosphatidylethanolamines such as 1,2-dioleoyl-phosphatidylethanolamine, 1,2-dipalmitoyl-phosphatidylethanolamine, 1,2-dimyristoyl-phosphatidylethanolamine, 1,2-distearoyl-phosphatidylethanolamine, 1-oleoyl-2-palmitoyl-phosphatidylethanolamine, 1-oleoyl-2-stearoyl-phosphatidylethanolamine, 1-palmitoyl-2-oleoyl-phosphatidylethanolamine, 1-stearoyl-2-oleoyl-phosphatidylethanolamine and N-succinyl-dioleoyl-phosphatidylethanolamine; phosphatidylserines such as 1,2-dioleoyl-phosphatidylserine, 1,2-dipalmitoyl-phosphatidylserine, 1,2-dimyristoyl-phosphatidylserine, 1,2-distearoyl-phosphatidylserine, 1-oleoyl-2-palmitoyl-phosphatidylserine, 1-oleoyl-2-stearoyl-phosphatidylserine, 1-palmitoyl-2-oleoyl-phosphatidylserine and 1-stearoyl-2-oleoyl-phosphatidylserine; phosphatidylglycerols such as 1,2-dioleoyl-phosphatidylglycerol, 1,2-dipalmitoyl-phosphatidylglycerol, 1,2-dimyristoyl-phosphatidylglycerol, 1,2-distearoyl-phosphatidylglycerol, 1-oleoyl-2-palmitoyl-phosphatidylglycerol, 1-oleoyl-2-stearoyl-phosphatidylglycerol, 1-palmitoyl-2-oleoyl-phosphatidylglycerol and 1-stearoyl-2-oleoyl-phosphatidylglycerol; pegylated lipids; pegylated phosphoholipids such as phophatidylethanolamine-N-[methoxy(polyethyleneglycol)-1000], phophatidylethanolamine-N-[methoxy(polyethyleneglycol)-2000], phophatidylethanolamine-N-[methoxy(polyethylene glycol)-3000], phophatidylethanolamine-N-[methoxy(polyethyleneglycol)-5000]; pegylated ceramides such as N-octanoyl-sphingosine-1-{succinyl[methoxy(polyethyleneglycol)1000]}, N-octanoyl-sphingosine-1-{succinyl[methoxy(polyethyleneglycol)2000]}, N-octanoyl-sphingosine-1-{succinyl[methoxy(polyethyleneglycol)3000]}, N-octanoyl-sphingosine-1-{succinyl[methoxy(polyethyleneglycol)5000]}; lyso-phosphatidylcholines, lyso-phosphatidylethanolamines, lyso-phosphatidylglycerols, lyso-phosphatidylserines, ceramides; sphingolipids; glycolipids such as ganglioside GMI; glucolipids; sulphatides; phosphatidic acid, such as di-palmitoyl-glycerophosphatidic acid; palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isostearic fatty acids; sterol and sterol derivatives such as cholesterol, cholesterol hemisuccinate, cholesterol sulphate, and cholesteryl-(4-trimethylammonio)-butanoate, ergosterol, lanosterol; polyoxyethylene fatty acids esters and polyoxyethylene fatty acids alcohols; polyoxyethylene fatty acids alcohol ethers; polyoxyethylated sorbitan fatty acid esters, glycerol polyethylene glycol oxy-stearate; glycerol polyethylene glycol ricinoleate; ethoxylated soybean sterols; ethoxylated castor oil; polyoxyethylene polyoxypropylene fatty acid polymers; polyoxyethylene fatty acid stearates; di-oleoyl-sn-glycerol; dipalmitoyl-succinylglycerol; 1,3-dipalmitoyl-2-succinylglycerol; 1-alkyl-2-acyl-phosphatidylcholines such as 1-hexadecyl-2-palmitoyl-phosphatidylcholine; 1-alkyl-2-acyl-phosphatidylethanolamines such as 1-hexadecyl-2-palmitoyl-phosphatidylethanolamine; 1-alkyl-2-acyl-phosphatidylserines such as 1-hexadecyl-2-palmitoyl-phosphatidylserine; 1-alkyl-2-acyl-phosphatidylglycerols such as 1-hexadecyl-2-palmitoyl-phosphatidylglycerol; 1-alkyl-2-alkyl-phosphatidylcholines such as 1-hexadecyl-2-hexadecyl-phosphatidylcholine; 1-alkyl-2-alkyl-phosphatidylethanolamines such as 1-hexadecyl-2-hexadecyl-phosphatidylethanolamine; 1-alkyl-2-alkyl-phosphatidylserines such as 1-hexadecyl-2-hexadecyl-phosphatidylserine; 1-alkyl-2-alkyl-phosphatidylglycerols such as 1-hexadecyl-2-hexadecyl-phosphatidylglycerol; N-Succinyl-dioctadecylamine; palmitoylhomocysteine; lauryltrimethylammonium bromide; cetyltrimethyl-ammonium bromide; myristyltrimethylammonium bromide; N-[1,2,3-dioleoyloxy)-propyl]-N,N,Ntrimethylammoniumchloride (DOTMA); 1,2-dioleoyloxy-3 (trimethyl-ammonium)propane (DOTAP); and 1,2-dioleoyl-c-(4'-trimethylammonium)-butanoyl-sn-glycerol (DOTB).

Such examples of suitable vesicle forming lipids used in the present invention or the methods of the present invention further include hydrogenated soy phosphatidylcholine (HSPC).

In one embodiment the vesicle forming component include compounds selected from the group of DSPC (1,2-distearoyl-sn-glycero-3-phosphocholine), CHOL (Cholesterol), DSPE-PEG-2000 (1,2-distearoyl-sn-glycero-3-phosphoethanolamine-N-[methoxy (polyethylene glycol)-2000]), POPC (1-palmitoyl-2-oleoyl-sn-glycero-3-phosphocholine), DPPC (1,2-dipalmitoyl-sn-glycero-3-phosphocholine), DSPE-PEG$_{2000}$-TATE, (1,2-distearoyl-sn-glycero-3-phosphoethanolamine-N-[methoxy (polyethylene glycol)-2000]-TATE).

In one preferred embodiment the vesicle forming component include compounds selected from the group of DSPC (1,2-distearoyl-sn-glycero-3-phosphocholine), CHOL (Cholesterol), DSPE-PEG-2000 (1,2-distearoyl-sn-glycero-3-phosphoethanolamine-N-[methoxy (polyethylene glycol)-2000]), POPC (1-palmitoyl-2-oleoyl-sn-glycero-3-phosphocholine), DPPC (1,2-dipalmitoyl-sn-glycero-3-phosphocholine), DSPE-PEG$_{2000}$-TATE, (1,2-distearoyl-sn-glycero-3-phosphoethanolamine-N-[methoxy (polyethylene glycol)-2000]-TATE) and hydrogenated soy phosphatidylcholine (HSPC).

In one embodiment of the nanoparticle composition, the vesicle forming component consists of amphiphatic compounds selected from the group consisting of 1,2-distearoyl-sn-glycero-3-phosphocholine (DSPC) "A", cholesterol "B", and 1,2-distearoyl-sn-glycero-3-phosphoethanolamine-N-[methoxy (polyethylene glycol)-2000] (DSPE-PEG-2000) "C" in the molar ratio of A:B:C, wherein A is selected from the interval 45 to 65, B is selected from the interval 35 to 45, and C is selected from the interval 2 to 20 and wherein A+B+C=100.

In one preferred embodiment of the nanoparticle composition, the vesicle forming component consists of amphiphatic compounds selected from the group consisting of 1,2-distearoyl-sn-glycero-3-phosphocholine (DSPC) "A", cholesterol "B", and 1,2-distearoyl-sn-glycero-3-phosphoethanolamine-N-[methoxy (polyethylene glycol)-2000] (DSPE-PEG-2000) "C" in the molar ratio of A:B:C, wherein A is selected from the interval 45 to 65, B is selected from the interval 35 to 45, and C is selected from the interval 1 to 20 and wherein A+B+C=100.

In another preferred embodiment the vesicle forming component include DSPC (1,2-distearoyl-sn-glycero-3-phosphocholine), CHOL (Cholesterol), DSPE-PEG-2000 (1,2-distearoyl-sn-glycero-3-phosphoethanolamine-N-[methoxy (polyethylene glycol)-2000]) in a molar ratio of 50:40:10.

In another embodiment of the disclosed method, the vesicle forming component consists of amphiphatic compounds selected from the group consisting of 1,2-distearoyl-sn-glycero-3-phosphocholine (DSPC) "A", cholesterol "B", and 1,2-distearoyl-sn-glycero-3-phosphoethanolamine-N-[methoxy (polyethylene glycol)-2000] (DSPE-PEG-2000) "C", and 1,2-distearoyl-sn-glycero-3-phosphoethanolamine- N-[methoxy (polyethylene glycol)-2000]-TATE (DSPE-PEG-2000-TATE) "D" with the molar ratio A:B:C:D, wherein A is selected from the interval 45 to 65, B is selected from the interval 35 to 45, C is selected from the interval 5 to 13, D is selected from the interval 0 to 3, and wherein A+B+C+D=100.

The radiolabeled nanoparticle composition mentioned above may further comprise a targeting moiety enabling the nanoparticle to specifically bind to target cells bearing the target molecule, or a moiety specifically binding to diseased target. The targeting moiety may be attached to the surface of the nanoparticle composition via a lipid-anchoring molecule or a PEG-conjugated lipid component.

The vesicle forming component may further comprise a lipid-conjugate of an antibody or an affibody or a peptide that acts as a targeting moiety to enable the nanoparticle to specifically bind to target cell bearing a target molecule.

The vesicle forming component may also consist of a lipid-conjugate of an antibody or an affibody or a peptide that acts as a targeting moiety to enable the nanoparticle to specifically bind to diseased target.

The antibodies useful in the present invention may be monospecific, bispecific, trispecific, or of greater multi-specificity. For example, multi-specific antibodies may be specific for different epitopes of a cytokine, cell, or enzyme which may be present in an increased amount at the target site compared to the normal tissues.

An "antibody" in accordance with the present specification is defined as a protein that binds specifically to an epitope. The antibody may be polyclonal or monoclonal. Examples of monoclonal antibodies useful in the present invention is selected from the group consisting of, but not limited to, Rituximab, Trastuzumab, Cetuximab, LymphoCide, Vitaxin, Lym-1 and Bevacizumab. In a preferred embodiment, the monoclonal antibodies are selected from the group consisting of Rituximab, Trastuzumab, Cetuximab, LymphoCide, Vitaxin, Lym-1, and Bevacizumab.

An "affibody" is defined as a small and stable antigen-binding molecule that can be engineered to bind specifically to a large number of target proteins. The affibody molecules mimic monoclonal antibodies in many ways, and in addition offer several unique properties making them a superior choice for a number of applications. These applications include incorporating the affibodies as lipid-conjugates in liposome compositions targeted for a tissue or a cell in a neovascular or inflammatory site, wherein the radionuclide, such as a copper isotope, but not limited to, $^{61}$Cu, $^{64}$Cu and $^{67}$Cu, is included for diagnostic and/or therapeutic applications. Examples of affibody molecules useful in the present invention is collected for the group consisting of, but not limited to, anti-ErbB2 affibody molecule and anti-Fibrinogen affibody molecule.

The peptides useful in the present invention act as a targeting moiety to enable the nanoparticle to specifically bind to a diseased target, wherein the peptides are selected from the group consisting of, but not limited to, RGD, somatostatin and analogs thereof, and cell-penetrating peptides. In one embodiment, the peptides are selected from the group consisting of RGD, somatostatin and analogs thereof, and cell-penetrating peptides. In one embodiment, the somatostatin analog is octreotate (TATE).

The vesicle forming components are selected to achieve a specified degree of fluidity or rigidity, to control the stability of the liposome compositions in vivo and to control the rate of release of the entrapped agent inside the liposome composition. The rigidity of the liposome composition, as determined by the vesicle forming components, may also play a role in the fusion or endocytosis of the liposome to a targeted cell.

The surface charge of the vesicles may also be an important factor in the loading of the vesicle, for controlling the stability of the liposome compositions in vivo and to control the rate of release of the entrapped agent inside the liposome composition. Thus according to the present invention, the vesicle forming components may further be selected in order to control the surface charge of the formed vesicles.

Agent-Entrapping Component

The agent-entrapping component of the present invention or the method of the present invention may be a chelating agent that forms a chelating complex with the transition metal or the radiolabeled agent, such as the radionuclide.

When a chelator (such as for example DOTA) is present in the aqueous phase of the liposome interior, the equilibrium between the exterior and the interior of the liposome is shifted since metal ions that pass the membrane barrier are effectively removed from the inner membrane leaflet due to tight binding to the chelator. The very effective complex formation of the metal ion with the chelator renders the free metal ion concentration in the liposome interior negligible and loading proceeds until all metal ions have been loaded into the liposome or equilibrium has been reached. If excess of chelator is used, the metal ion concentration in the liposomes will be low at all stages during loading and the trans-membrane gradient will be defined by the free metal ion concentration on the exterior of the liposomes.

According to the present invention, chelators may be selected from the group comprising 1,4,7,10-tetraazacyclododecane-1,4,7,10-tetraacetic acid (DOTA) and derivatives thereof; 1,4,8,11-tetraazacyclotetradecane (cyclam) and derivatives thereof; 1,4,7,10-tetraazacyclododecane (cyclen) and derivatives thereof; 1,4-ethano-1,4,8,11-tetraazacyclotetradecane (et-cyclam) and derivatives thereof; 1,4,7,11-tetra-azacyclotetradecane (isocyclam) and derivatives thereof; 1,4,7,10-tetraazacyclotridecane ([13]aneN$_4$) and derivatives thereof; 1,4,7,10-tetraazacyclododecane-1,7-diacetic acid (DO2A) and derivatives thereof; 1,4,7,10-tetraazacyclododecane-1,4,7-triacetic acid (DO3A) and derivatives thereof; 1,4,7,10-tetraazacyclododecane-1,7-di (methanephosphonic acid) (DO2P) and derivatives thereof; 1,4,7,10-tetraazacyclododecane-1,4,7-tri(methanephosphonic acid) (DO3P) and derivatives thereof; 1,4,7,10-tetraazacyclododecane-1,4,7,10-tetra(methanephosphonic acid) (DOTP) and derivatives thereof; ethylenediaminetetraacetic acid (EDTA) and derivatives thereof; diethylenetriaminepentaacetic acid (DTPA) and derivatives thereof; 1,4,8,11-tetraazacyclotetradecane-1,4,8,11-tetraacetic acid (TETA) and derivatives thereof, or other adamanzanes and derivates thereof.

In another embodiment, the agent-entrapping component according to the present invention may be a substance that has the ability to reduce other substances, thus referred to as a reducing agent. Examples of reducing agents comprise ascorbic acid, glucose, fructose, glyceraldehyde, lactose, arabinose, maltose and acetol.

In one embodiment of the present invention the loaded copper isotope, which may be Cu(II) or Cu(I) cations, is reduced to a lower oxidation state upon diffusion through the vesicle membrane, thus trapping the copper isotope within the vesicle. In another embodiment, the radionuclide different from copper, is reduced to a lower oxidation state upon diffusion through the vesicle membrane, thus trapping the radionuclide different from copper within the vesicle.

In a further embodiment, an agent-entrapping component within the scope of the present invention or the method of present invention may be a substance with which the radionuclide or metal entity, such as copper isotope, forms a low solubility salt. Examples of such are copper phosphates, copper oxalate and copper chlorides. In one embodiment, the low solubility salt formed with copper (Cu(II) or Cu(I)) is selected from the group consisting of copper phosphates, copper oxalate and copper chlorides.

In one embodiment of the present invention or the method of the present invention the agent-entrapping component is a chelator selected from the group consisting of macrocyclic compounds comprising adamanzanes; 1,4,7,10-tetraazacyclododecane ([12]aneN$_4$) or a derivative thereof; 1,4,7,10-tetraazacyclotridecane ([13]aneN$_4$) or a derivative thereof; 1,4,8,11-tetraazacyclotetradecane ([14]aneN$_4$) or a derivative thereof; 1,4,8,12-tetraazacyclopentadecane ([15]aneN$_4$) or a derivative thereof; 1,5,9,13-tetraazacyclohexadecane ([16]aneN$_4$) or a derivative thereof; and other chelators capable of binding metal ions such as ethylene-diamine-tetraacetic-acid (EDTA) or a derivative thereof, diethylene-triamine-penta-acetic acid (DTPA) or a derivative thereof.

In one embodiment of the present invention or the method of the present invention the agent-entrapping component is a chelator selected from the group consisting of 1,4-ethano-1,4,8,11-tetraazacyclotetradecane (et-cyclam) or a derivative thereof; 1,4,7,11-tetraazacyclotetradecane (iso-cyclam) or a derivatives thereof; 1,4,7,10-tetraazacyclododecane-1,4,7,10-tetraacetic acid (DOTA) or a derivative thereof; 2 (1,4,7,10-tetraazacyclododecan-1-yl)acetate (DO1A) or a derivative thereof; 2,2'-(1,4,7,10-tetraazacyclododecane-1,7-diyl) diacetic acid (DO2A) or a derivative thereof; 2,2',2"-(1,4,7,10-tetraazacyclododecane-1,4,7-triyl) triacetic acid (DO3A) or a derivative thereof; 1,4,7,10-tetraazacyclododecane-1,4,7,10-tetra(methanephosphonic acid) (DOTP) or a derivative thereof; 1,4,7,10-tetraazacyclododecane-1,7-di(methanephosphonic acid) (DO2P) or a derivative thereof; 1,4,7,10-tetraazacyclododecane-1,4,7-tri(methanephosphonic acid) (DO3P) or a derivative thereof; 1,4,8,11-15 tetraazacyclotetradecane-1,4,8,11-tetraacetic acid (TETA) or a derivative thereof; 2-(1,4,8,11-tetraazacyclotetradecane-1-yl) acetic acid (TE1A) or a derivative thereof; 2,2'-(1,4,8,11-tetraazacyclotetradecane-1,8-diyl) diacetic acid (TE2A) or a derivative thereof; and other adamanzanes or derivates thereof.

In one embodiment of the present invention or the method of the present invention the agent-entrapping component is selected from the group consisting of 1,4,7,10-tetraazacyclododecane-1,4,7,10-tetraacetic acid (DOTA) or a derivative thereof, 1,4,8,11-15 tetraazacyclotetradecane-1,4,8,11-tetraacetic acid (TETA) or a derivative thereof, 1,4,7,10-tetraazacyclododecane-1,4,7,10-tetra(methanephosphonic acid) (DOTP), cyclam and cyclen.

In a particularly important embodiment of the present invention or method of the present invention, the agent-entrapping component is 1,4,7,10-tetraazacyclododecane-1,4,7,10-tetraacetic acid (DOTA).

Ionophores

Ionophores can be characterized as ion-transporters, lipophilic chelators, channel formers, lipophilic complexes etc. In general an ionophore can be defined as a lipid-soluble molecule that transports ions across the lipid bilayer of cell membranes or liposomes. Ionophores are used to increase permeability of lipid membranes to ions and facilitate transfer of molecules through, into and out of the membrane. There are general two broad classifications of ionophores, where one is; chemical compounds, mobile carriers or lipophilic chelators that bind or chelate to a particular ion or molecule, shielding its charge from the surrounding environment, and thus facilitating its crossing of the hydrophobic interior of the lipid membrane. The second classification is; channel formers that introduce a hydrophilic pore into the membrane, allowing molecules or metal ions to pass through while avoiding contact with the hydrophobic interior of the membrane.

In conventional methods using ionophores, or other components capable of transporting ions or loading of nanoparticles, the resulting nanoparticles comprise small amounts of the ion-transporter or ionophore used in the loading procedure. The nanoparticles provided by the present invention are prepared without the use of an ion-transporter such as an ionophore. Thus, the present invention relates to nanoparticle compositions, which do not comprise ion-transporters or ionophores.

In another embodiment of the present invention, the nanoparticle compositions as defined herein do not comprise any added ionophores.

Ion-transporters or ionophoric compounds which are not comprised in the nanoparticles of the present invention may be selected from the group of 8-hydroxyquinoline (oxine); 8-hydroxyquinoline β-D-galactopyranoside; 8-hydroxyquinoline β-D-glucopyranoside; 8-hydroxyquinoline glucuronide; 8-hydroxyquinoline-5-sulfonic acid; 8-hydroxyquinoline-β-D-glucuronide sodium salt; 8-quinolinol hemisulfate salt; 8-quinolinol N-oxide; 2-amino-8-quinolinol; 5,7-dibromo-8-hydroxyquinoline; 5,7-dichloro-8-hydroxyquinoline; 5,7-diiodo-8-hydroxyquinoline; 5,7-dimethyl-8-quinolinol; 5-amino-8-hydroxyquinoline dihydrochloride; 5-chloro-8-quinolinol; 5-nitro-8-hydroxyquinoline; 7-bromo-5-chloro-8-quinolinol; N-butyl-2,2'-imino-di(8-quinolinol); 8-hydroxyquinoline benzoate; 2-benzyl-8-hydroxyquinoline; 5-chloro-8-hydroxyquinoline hydrochloride; 2-methyl-8-quinolinol; 5-chloro-7-iodo-8-quinolinol; 8-hydroxy-5-nitroquinoline; 8-hydroxy-7-iodo-5-quinolinesulfonic acid; 5,7-dichloro-8-hydroxy-2-methylquinoline, and other quinolines (1-azanaphthalene, 1-benzazine) consisting chemical compounds and derivatives thereof. In one embodiment the ionophoric compound is selected from the group consisting of: 8-hydroxyquinoline (oxine); 8-hydroxyquinoline β-D-galactopyranoside; 8-hydroxyquinoline β-D-glucopyranoside; 8-hydroxyquinoline glucuronide; 8-hydroxyquinoline-5-sulfonic acid; 8-hydroxyquinoline-β-D-glucuronide sodium salt; 8-quinolinol hemisulfate salt; 8-quinolinol N-oxide; 2-amino-8-quinolinol; 5,7-dibromo-8-hydroxyquinoline; 5,7-dichloro-8-hydroxyquinoline; 5,7-diiodo-8-hydroxyquinoline; 5,7-dimethyl-8-quinolinol; 5-amino-8-hydroxyquinoline dihydrochloride; 5-chloro-8-quinolinol; 5-nitro-8-hydroxyquinoline; 7-bromo-5-chloro-8-quinolinol; N-butyl-2,2'-imino-di(8-quinolinol); 8-hydroxyquinoline benzoate; 2-benzyl-8-hydroxyquinoline; 5-chloro-8-hydroxyquinoline hydrochloride; 2-methyl-8-quinolinol; 5-chloro-7-iodo-8-quinolinol; 8-hydroxy-5-nitroquinoline; 8-hydroxy-7-iodo-5-quinolinesulfonic acid; 5,7-dichloro-8-hydroxy-2-methylquinoline, and other quinolines (1-azanaphthalene, 1-benzazine) consisting chemical compounds and derivatives thereof.

Ion-transporters or ionophoric compounds which are not comprised in the nanoparticles or used in the methods of the present invention may additionally be selected from the group consisting of 2-hydroxyquinoline-4-carboxylic acid; 6-chloro-2-hydroxyquinoline; 8-chloro-2-hydroxyquinoline; carbostyril 124; carbostyril 165; 4,6-dimethyl-2-hydroxyquinoline; 4,8-dimethyl-2-hydroxyquinoline; or other 2-quinolinol compounds 8-hydroxyquinoline (oxine); 8-hydroxyquinoline β-D-galactopyranoside; 8-hydroxyquinoline β-D-glucopyranoside; 8-hydroxyquinoline glucuronide; 8-hydroxyquinoline-5-sulfonic acid; 8-hydroxyquinoline-β-D-glucuronide sodium salt; 8-quinolinol hemisulfate salt; 8-quinolinol N-oxide; 2-amino-8-quinolinol; 5,7-dibromo-8- hydroxyquinoline; 5,7-dichloro-8-hydroxyquinoline; 5,7-diiodo-8-hydroxyquinoline; 5,7-dimethyl-8-quinolinol; 5-amino-8-hydroxyquinoline dihydrochloride; 5-chloro-8-quinolinol; 5-nitro-8-hydroxyquinoline; 7-bromo-5-chloro-8-quinolinol; N-butyl-2,2'-imino-di(8-quinolinol); 8-hydroxyquinoline benzoate; 2-benzyl-8-hydroxyquinoline; 5-chloro-8-hydroxyquinoline hydrochloride; 2-methyl-8-quinolinol; 5-chloro-7-iodo-8-quinolinol; 8-hydroxy-5-nitroquinoline; 8-hydroxy-7-iodo-5-quinolinesulfonic acid; 5,7-dichloro-8-hydroxy-2-methylquinoline, and other quinolines (1-azanaphthalene, 1-benzazine) consisting chemical compounds and derivatives thereof, [6S-[6.alpha.(2S*,3S*), 8.beta.(R*),9.beta., 11.alpha]]-5-(methylamino)-2-[[3,9,11-trimethyl-8-[1-methyl-2-oxo-2-(1H-pyrrol2-yl)ethyl]-1,7-dioxaspiro[5.5]undec-2-yl]methyl]-4-benzoxazolecarboxylic acid (also called A23187), HMPAO (hexamethyl propylene amine oxime, HYNIC (6-Hydrazinopyridine-3-carboxylic acid), BMEDA (N—N-bis(2-mercaptoethyl)-N', N'-diethylethylenediamine), DISIDA (diisopropyl iminodiacetic acid, phthaldialdehyde and derivatives thereof, 2,4-dinitrophenol and derivatives thereof, di-benzo-18-crown-6 and derivatives thereof, o-xylylenebis(N,N-diisobutyldithiocarbamate) and derivatives thereof, N,N,N',N'-Tetracyclohexyl-2,2'-thiodiacetamide and derivates thereof, 2-(1,4,8, 11-Tetrathiacyclotetradec-6-yloxy)hexanoic acid, 2-(3,6,10, 13-Tetrathiacyclotetradec-1-oxy)hexanoic acid and derivates thereof, N,N-bis(2-mercaptoethyl)-N',N'-diethylethylenediamine and derivatives thereof, beauvericin, enniatin, gramicidin, ionomycin, lasalocid, monesin, nigericin, nonactin, nystatin, salinomycin, valinomycin, pyridoxal isonicotinoyl hydrazone (PIH), salicylaldehyde isonicotinoyl hydrazone (SIH), 1,4,7-trismercaptoethyl-1,4,7-triazacyclononane, N,N',N'''-tris(2-mercaptoethyl)-1,4,7-triaza-cyclononane, monensis, DP-b99, DP-109, BAPTA, pyridoxal isonicotinoyl hydrazone (PIH), alamethicin, di-2-pyridylketone thiosemicarbazone (HDpT), carbonyl cyanide m-chlorophenyl hydrazone (CCCP), lasalocid A (X-537A), 5-bromo derivative of lasalocid; cyclic depsipeptides; cyclic peptides: DECYL-2; N,N,N',N'-tetrabutyl-3,6-dioxaoctanedi[thioamide]); N,N, N',N'-tetracyclohexyl-3-oxa-pentanediamide; N,N-dicyclohexyl-N',N'-dioctadecyl-diglycolic-diamide; N,N'-diheptyl-N,N'-dimethyl-1,-butanediamide; N,N'''-octamethylene-bis [N'-heptyl-N'-methyl-malonamide; N,N-dioctadecyl-N',N'-dipropyl-3,6-dioxaoctanediamide; N-[2-(1H-pyrrolyl-methyl)]-N'-(4-penten-3-on-2)-ethane-1,2-diamine (MRP20); and antifungal toxins; avenaciolide or derivatives of the above mentioned ionophores, as well as the ionophores described in WO2011/006510 and other ionophores described in the art.

pH gradient loadable agents i.e. agents with one or more ionisable moieties such that the neutral form of the ionisable moiety allows the metal entities to cross the liposome membrane and conversion of the moiety to a charged form causes the metal entity to remain encapsulated within the liposome are also regarded as ionophores according to the present invention. Ionisable moieties may comprise, but are not limited to comprising, amine, carboxylic acid and hydroxyl groups. pH gradient loadable agents that load in response to an acidic interior may comprise ionisable moieties that are charged in response to an acidic environment whereas drugs that load in response to a basic interior comprise moieties that are charged in response to a basic environment. In the case of a basic interior, ionisable moieties including but not limited to carboxylic acid or hydroxyl groups may be utilized.

Interior PH

The interior pH of the nanoparticles according to the present invention can be controlled to lie in a specific range wherein the features of the nanoparticle are optimized.

In one embodiment of the present invention or the method of the present invention, the interior pH of the liposome composition is controlled, thus achieving a desired protonation state of the agent-entrapping component and/or the ionophore, thereby securing efficient loading and entrapment of the radionuclide.

In a preferred embodiment of the present invention or the method of the present invention, the interior pH of the liposome composition is controlled, thus achieving a desired protonation state of the agent-entrapping component, thereby securing efficient loading and entrapment of the radionuclide.

In another embodiment of the disclosed method for producing a nanoparticle composition loaded with a copper isotope, the interior pH is controlled during synthesis of the nanoparticles in such a way that the interior pH of the nanoparticles is within the range of 1 to 10, such as 1-2, for example 2-3, such as 3-4, for example 4-5, such as 5-6, for example 6-7, such as 7-8, for example 8-9, such as 9-10.

In a preferred embodiment of the present invention, the interior pH of the nanoparticles is in the range of 4 to 8.5, such as 4.0 to 4.5, for example 4.5 to 5.0, such as 5.0 to 5.5 for example 5.5 to 6.0, such as 6.0 to 6.5, for example 6.5 to 7.0, such as 7.0 to 7.5, for example 7.5 to 8.0, such as 8.0 to 8.5.

In another embodiment of the present invention, the interior pH of the nanoparticles according to the present invention is optimized in order to prolong the stability of the nanoparticles. Such improved stability can for example lead to a longer shelf-life or a wider range of possible storage temperatures and thereby facilitate the use of the nanoparticles. The improved stability can be obtained, for example because the interior pH leads to an increased stability of the vesicle forming components forming a vesicle, due to increased stability of the agent-entrapping component with or without the entrapped radionuclides or due to improved stability of other features of the nano-particles. An interior pH which is optimized for improved stability may be within the range of 1 to 10, such as 1-2, for example 2-3, such as 3-4, for example 4-5, such as 5-6, for example 6-7, such as 7-8, for example 8-9, such as 9-10.

In a preferred embodiment of the present invention, the interior pH which leads to an improved stability of the nanoparticles is in the range of 4 to 8.5, such as 4.0 to 4.5, for example 4.5 to 5.0, such as 5.0 to 5.5 for example 5.5 to 6.0, such as 6.0 to 6.5, for example 6.5 to 7.0, such as 7.0 to 7.5, for example 7.5 to 8.0, such as 8.0 to 8.5.

Osmotic Pressure

The creation of a small osmotic stress on the vesicle or nanoparticle membrane is favourable in the loading of metal entity and/or radionuclide into the nanoparticles. Osmotic stress is a difference in osmotic pressure, i.e. an imbalance or difference between interior and exterior osmolarity. Presence of an osmotic stress facilitates the transfer of smaller ions over the membrane, such as metal ions or radionuclide ions, while larger charged molecules such as chelating agents remain trapped within the nanoparticles.

According to the present invention, the loading into liposomes can be modulated by controlling the osmolarity of the aqueous solution that is encapsulated in the liposomes as well as the exterior solution during manufacture of the liposomes. The osmolarity (Osm) is a measure of the activity of water (as a function of the chemical potential), which is governed by the presence of solutes in the aqueous solution, including chelators or other osmotically active agents. Trans-membrane gradients of osmolytes influences the state of the liposome and can either cause the liposome to be flaccid ($Osm_{interior} < Osm_{exterior}$) due to loss of water or to be tense due to uptake of water building up osmotic trans-membrane pressure ($Osm_{interior} > Osm_{exterior}$) and membrane tension. In general, membrane tension will lead to membrane stretching and thus thinning of the bilayer causing an increased permeability. Furthermore, membrane tension can cause formation of defects (transient pores), which also attributes to increased membrane permeability. It is thus expected that the membrane permeability increases with augmented hyper-osmotic pressure ($Osm_{interior} > Osm_{exterior}$) leading to higher loading rate and loading efficiency. A too high osmotic pressure (tension) can also induce lysis of the liposomes and cause a gradual release of contents or mechanical failure of the liposome. For example, when 100 nm vesicles are placed in a hypo-osmotic solution with respect to the trapped intra-vesicular medium, it can result in an influx of water causing the vesicles to assume a spherical shape, and osmotic differentials of sufficient magnitude will produce membrane rupture that results in partial release of the intra-vesicular solutes. However, it is recognized that the presence of cholesterol in the membrane provide mechanical stability thereby increasing the membrane lysis tension resulting overall in a larger tolerance towards osmotic imbalance.

The intra-liposomal osmolarity can be determined by measuring the osmolarity of the solution used to hydrate lipid films during liposome preparation, by using conventional methods in the art such as, but not limited to the freeze-point method, which is commonly used in apparatus for measuring osmolarity. The same method can be utilized for measuring the osmolarity of the external liposomal buffer. Importantly, the buffer osmolarity is easily influenced by pH adjustment (using e.g. NaOH or HCl) during buffer preparation.

In a preferred embodiment of the present invention, the osmolarity is measured by use of the freeze point method.

Controlling the osmolarity can be used to create osmotic stress. Such osmotic stress can be controlled by entrapping osmotic agents such as sugars, salts, chelating agents, ions, peptides, proteins, pharmaceutical compounds, buffer molecules and/or solutes in the nanoparticles.

In one embodiment of the present invention, the osmolarity of the interior of the nanoparticles is 40-800 mOsm/L, such as 40-100 mOsm/L, or such as 100-150 mOsm/L, or such as 150-200 mOsm/L, or such as 200-250 mOsm/L, or such as 250-300 mOsm/L, or such as 300-350 mOsm/L, or such as 350-400 mOsm/L, or such as 400-450 mOsm/L, or such as 450-500 mOsm/L, or such as 500-550 mOsm/L, or such as 550-600 mOsm/L, or such as 600-650 mOsm/L, or such as 650-700 mOsm/L or such as 700-750 mOsm/L, or such as 750-800 mOsm/L.

In another embodiment of the present invention, the osmolarity of the exterior of the nanoparticles is 40-800 mOsm/L, such as 40-100 mOsm/L, or such as 100-150 mOsm/L, or such as 150-200 mOsm/L, or such as 200-250 mOsm/L, or such as 250-300 mOsm/L, or such as 300-350 mOsm/L, or such as 350-400 mOsm/L, or such as 400-450 mOsm/L, or such as 450-500 mOsm/L, or such as 500-550 mOsm/L, or such as 550-600 mOsm/L, or such as 600-650 mOsm/L, or such as 650-700 mOsm/L or such as 700-750 mOsm/L, or such as 750-800 mOsm/L.

In one embodiment of the present invention, the difference in osmolarity between the interior of the nanoparticle and the exterior of the nanoparticle is 5-800 mOsm/L, such as 5-10 mOsm/L such as 10-20 mOsm/L, or such as 10-20 mOsm/L, or such as 20-20-30 mOsm/L, or such as 30-40 mOsm/L, such as 40-50 mOsm/L, or such as 50-60 mOsm/L, or such as 60-70 mOsm/L, or such as 60-70 mOsm/L, or such as 70-80 mOsm/L, or such as 80-90 mOsm/L, or such as 90-100 mOsm/L, or such as 100-150 mOsm/L, or such as 150-200 mOsm/L, or such as 200-250 mOsm/L, or such as 250-300 mOsm/L, or such as 300-350 mOsm/L, or such as 350-400 mOsm/L, or such as 400-450 mOsm/L, or such as 450-500 mOsm/L, or such as 500-550 mOsm/L, or such as 550-600 mOsm/L, or such as 600-650 mOsm/L, or such as 650-700 mOsm/L, or such as 700-750 mOsm/L, or such as 750-800 mOsm/L.

In one particular embodiment of the present invention, the difference in osmolarity between the interior of the nanoparticle and the exterior of the nanoparticle is 10-100 mOsm/L.

Stability

The nanoparticles of the present invention have improved stability, which may be measured using different tests.

In one embodiment of the present invention, the stability of the radiolabeled nanoparticles is such that less than 20% leakage of radioactivity is observed following a given time of incubation in buffer or human serum. Such leakage can be less than 20%, for example less than 15% leakage, such as less than 12% leakage, for example less than 10% leakage, such as less than 8% leakage, for example less than 6% leakage, such as less than 4% leakage, for example less than 3% leakage, such as less than 2% leakage, for example less than 1% leakage as measured by conventional methods in the art, including a purification procedure such as size exclusion chromatograpy (SEC), ion-exchange chromatography or dialysis. The amount of metal entity such as the radionuclide can be measured as radioactivity using a radioactivity detector or by measuring the concentration of the metal entity using inductively coupled plasma mass spectrometry (ICP-MS), inductively coupled plasma atomic emission spectroscopy (ICP-AES) or inductively coupled plasma optical emission spectrometry (ICP-OES).

In one embodiment of the present invention, the stability of the radiolabeled nanoparticles is such that less than 20% leakage of radioactivity is observed following 24 hours incubation in buffer or human serum at 37° C. followed by a purification procedure to separate the radiolabeled nanoparticles from leaked radionuclide, for example less than 15% leakage, such as less than 12% leakage, for example less than 10% leakage, such as less than 8% leakage, for example less than 6% leakage, such as less than 4% leakage, for example less than 3% leakage, such as less than 2% leakage, for example less than 1% leakage. Said purification procedure comprises size exclusion chromatograpy (SEC), ion-exchange chromatography or dialysis. The amount of metal entity such as the radionuclide is measured as radioactivity using a radioactivity detector or by measuring the concentration of the metal entity using inductively coupled plasma mass spectrometry (ICP-MS), inductively coupled plasma atomic emission spectroscopy (ICP-AES) or inductively coupled plasma optical emission spectrometry (ICP-OES).

Sizes of the Nanoparticles

Nanoparticles according to the present invention may vary in size. The size of the nanoparticles may be optimized for the use of the nanoparticle wherein the nanoparticle is administered to a subject, for example for improving targeting of the particles to sites in the human body, or for improved monitoring of the nanoparticles inside the human body. The size may also be optimized for improved for stability of the nanoparticle or for improved or facilitated preparation of the nanoparticles.

In one embodiment, the nanoparticle composition of the present invention has a diameter in the range of 30 nm to 1000 nm; such as 30 nm to 300 nm, such as 30 nm to 60 nm, for example 60 nm to 80 nm, such as 80 nm to 100 nm, for example 100 nm to 120 nm, such as 120 nm to 150 nm, for example 150 nm to 180 nm, such as 180 nm to 210 nm, for example, 210 nm to 240 nm, such as 240 nm to 270 nm for example 270 nm to 300 nm, or such as 300 nm to 600 nm, such as 300 nm to 400 nm, or such as 400 nm to 500 nm, or such as 500 nm to 600 nm, or such as 600 nm to 1000 nm, such as 600 nm to 700 nm, or such as 700 nm to 800 nm, or such as 800 nm to 900 nm, or such as 900 nm to 1000 nm.

In one embodiment, the disclosed method for producing a nanoparticle loaded with radionuclides results in nanoparticles which has a diameter in the range of 30 nm to 1000 nm; such as 30 nm to 300 nm, such as 30 nm to 60 nm, for example 60 nm to 80 nm, such as 80 nm to 100 nm, for example 100 nm to 120 nm, such as 120 nm to 150 nm, for example 150 nm to 180 nm, such as 180 nm to 210 nm, for example, 210 nm to 240 nm, such as 240 nm to 270 nm for example 270 nm to 300 nm, or such as 300 nm to 600 nm, such as 300 nm to 400 nm, or such as 400 nm to 500 nm, or such as 500 nm to 600 nm, or such as 600 nm to 1000 nm, such as 600 nm to 700 nm, or such as 700 nm to 800 nm, or such as 800 nm to 900 nm, or such as 900 nm to 1000 nm.

In one embodiment, the disclosed method for producing a nanoparticle loaded with copper results in nanoparticles which has a diameter in the range of 30 nm to 1000 nm; such as 30 nm to 300 nm, such as 30 nm to 60 nm, for example 60 nm to 80 nm, such as 80 nm to 100 nm, for example 100 nm to 120 nm, such as 120 nm to 150 nm, for example 150 nm to 180 nm, such as 180 nm to 210 nm, for example, 210 nm to 240 nm, such as 240 nm to 270 nm for example 270 nm to 300 nm, or such as 300 nm to 600 nm, such as 300 nm to 400 nm, or such as 400 nm to 500 nm, or such as 500 nm to 600 nm, or such as 600 nm to 1000 nm, such as 600 nm to 700 nm, or such as 700 nm to 800 nm, or such as 800 nm to 900 nm, or such as 900 nm to 1000 nm.

In a preferred embodiment, the nanoparticle composition of the present invention has a diameter in the range of 30 nm to 300 nm; such as 30 nm to 60 nm, for example 60 nm to 80 nm, such as 80 nm to 100 nm, for example 100 nm to 120 nm, such as 120 nm to 150 nm, for example 150 nm to 180 nm, such as 180 nm to 210 nm, for example, 210 nm to 240 nm, such as 240 nm to 270 nm for example 270 nm to 300 nm.

In a preferred embodiment, the disclosed method for producing a nanoparticle loaded with radionuclides results in nanoparticles which has a diameter in the range of 30 nm to 300 nm; such as 30 nm to 60 nm, for example 60 nm to 80 nm, such as 80 nm to 100 nm, for example 100 nm to 120 nm, such as 120 nm to 150 nm, for example 150 nm to 180 nm, such as 180 nm to 210 nm, for example, 210 nm to 240 nm, such as 240 nm to 270 nm for example 270 nm to 300 nm.

In a preferred embodiment, the disclosed method for producing a nanoparticle loaded with copper results in nanoparticles which has a diameter in the range of 30 nm to 300 nm; such as 30 nm to 60 nm, for example 60 nm to 80 nm, such as 80 nm to 100 nm, for example 100 nm to 120 nm, such as 120 nm to 150 nm, for example 150 nm to 180 nm, such as 180 nm to 210 nm, for example, 210 nm to 240 nm, such as 240 nm to 270 nm for example 270 nm to 300 nm.

Methods for Preparation

The present invention provides methods for preparation of nanoparticle compositions as described herein comprising a vesicle forming component, an agent-entrapping component enclosed by the vesicle forming component, and an entrapped metal entity within the nanoparticle composition.

Such methods for preparation of nanoparticles according to the present invention comprise the following steps:

a. Providing a nanoparticle composition comprising a vesicle forming component and an agent-entrapping component enclosed by said vesicle forming component;

b. Entrapping the metal entities within the interior of the nanoparticle composition by incubation of the nanoparticle composition in a solution comprising the metal entity at a temperature higher than 22° C.

Preferred methods for preparation of nanoparticles according to the present invention which do not involve the use of ionophore for loading, comprise the following steps:

a. Providing a nanoparticle composition comprising a vesicle forming component and an agent-entrapping component enclosed by said vesicle forming component;

b. Entrapping the metal entities within the interior of the nanoparticle composition by enabling transfer of cation metal entities across the membrane of the vesicle forming component by incubation of the nanoparticle composition in a solution comprising the metal entity.

In one embodiment, the methods according to the present invention, the incubation temperature for loading of the nanoparticles is higher than 22° C., such as higher than 30° C., such as higher than 35° C., such as higher than 40° C., such as higher than 45° C., such as higher than 50° C., such as higher than 55° C., such as higher than 60° C., such as higher than 65° C., such as higher than 70° C., such as higher than 75° C.

In another embodiment, the methods according to the present invention, the incubation temperature for loading of the nanoparticles is higher than 10° C., such as higher than 15° C., such as higher than 22° C., such as higher than 30° C., such as higher than 35° C., such as higher than 40° C., such as higher than 45° C., such as higher than 50° C., such as higher than 55° C., such as higher than 60° C., such as higher than 65° C., such as higher than 70° C., such as higher than 75° C.

In the methods according to the present invention, the incubation temperature for loading of the nanoparticles is lower than a critical temperature where upon the nanoparticles will degrade. Thus according to the present invention, the incubation temperature for loading of the nanoparticles is lower than 100° C., such as lower than 90° C., such as lower than 85° C., such as lower than 80° C.

In yet another embodiment of the present invention, incubation temperature for loading of the nanoparticles is between 22° C. to 80° C., such as 22° C. to 30° C., or in the range of 30° C. to 80° C., such as in the range of 30° C. to 40° C., such as 30° C. to 35° C., or such as 35° C. to 40° C., or in the range of 40° C. to 80° C., such as 40° C. to 45° C., or such as 45° C. to 50° C., including the range of 50° C. to 80° C., such as 50° C. to 55° C., or such as 55° C. to 60° C., or such as 60° C. to 65° C., or such as 65° C. to 70° C., or such as 70° C. to 75° C., or such as 75° C. to 80° C., wherein a range of 30° C. to 80° C. is preferred and a range of 40° C. to 80° C. is more preferred.

In yet another embodiment of the present invention, incubation temperature for loading of the nanoparticles is between 10° C. to 80° C., such as 15° C. to 80° C., or such as 15° C. to 22° C., or in the range of 22° C. to 80° C., such as 22° C. to 30° C., such as in the range of 30° C. to 80° C., such as in the range of 30° C. to 40° C., such as 30° C. to 35° C., or such as 35° C. to 40° C., or in the range of 40° C. to 80° C., such as 40° C. to 45° C., or such as 45° C. to 50° C., including the range of 50° C. to 80° C., such as 50° C. to 55° C., or such as 55° C. to 60° C., or such as 60° C. to 65° C., or such as 65° C. to 70° C., or such as 70° C. to 75° C., or such as 75° C. to 80° C., wherein a range of 30° C. to 80° C. is preferred and a range of 40° C. to 80° C. is more preferred.

The methods of the present invention allows for a faster loading of the nanoparticles than what is expected from mere diffusion of the metal entities/radionuclides into the nanoparticles.

Thus, in one embodiment of the present invention, the incubation for loading of the nanoparticles can be performed in a time period which is less than 48 hours, such as 36-48 hours, or such as 24-36 hours, or such as 18-24 hours, or such as 16-18 hours, or such as 14-16 hours, or such as 12-14 hours, or such as 10-12 hours, or such as 8-10 hours, or such as 6-8 hours, or such as 4-6 hours, or such as 2-4 hours, or such as 1-2 hours, or such as 30 min to 60 min, or 5 min to 30 min, or 1 min to 5 min.

The incubation time according to the present invention is a time period shorter than 48 hours, such as between 0 minutes to 360 minutes, such as between 1 minutes to 240 minutes preferably between 1 minutes to 120 minutes (including 3 minutes to 120 minutes and 5 minutes to 120 minutes) and more preferably between 1 minutes to 60 minutes, such as 5 minutes to 60 minutes.

The methods of the present invention may comprise one or more steps wherein an osmotic stress as defined herein is created in the nanoparticles. The inventors have found that a difference in the osmolarity of the interior of the nanoparticle compared to the exterior of the nanoparticle improves the loading of the nanoparticles. Said osmotic stress can be created by ensuring that there is an imbalance between the interior ion concentration of the nanoparticles compared to the exterior ion concentration, thus a difference in the osmotic pressure over the membrane of the vesicle.

Such osmotic stress or osmotic pressure can be controlled by an entrapped osmotic agent such as salts, sugars, ions, chelates, peptides, proteins, pharmaceutical compounds, buffer molecules, and/or other solutes.

In one embodiment of the present invention, the osmotic pressure of the membrane is obtained by controlling the osmolarity of the interior of the nanoparticle by preparing the nanoparticle composition in step a) using a solution which has an osmolarity for enhancing the loading, wherein said solution comprises one or more osmotic agents as defined herein.

In another embodiment of the present invention, the osmotic pressure of the membrane is obtained by controlling the osmolarity of the exterior of the nanoparticle by incubating the nanoparticle composition in step b) using a solution which has an osmolarity for enhancing the loading, wherein said solution comprises one or more osmotic agents as defined herein.

Thus in one embodiment of the present invention, the difference in osmolarity of the interior of the nanoparticle compared to the incubation solution (exterior of the nanoparticle) is 5-800 mOsm/L at the starting point of the incubation.

The methods of the present invention ensure that a high amount of the radionuclides used in preparation will be entrapped within the nanoparticle. In one embodiment of the present invention or the method of the present invention, the efficiency of loading is higher than 90% when assayed using size exclusion chromatography (SEC, described in examples), ion-exchange chromatography or dialysis. In another embodiment of the present method the efficiency of loading is higher than 35%, for example higher than 40%, such as higher than 50%, for example higher than 60%, such as higher than 65%, for example higher than 70%, such as higher than 75%, for example higher than 80%, such as higher than 85%, for example higher than 90%, such as higher than 95%, or such as higher than 96%, or such as higher than 97%, or such as higher than 98%, or such as higher than 99%.

In one embodiment of the present invention, the loading efficiency when using incubation times of 1 minutes to 240 minutes is in the range of 10% to 100%, preferably in the range of 80% to 100% and more preferably in the range of 90% to 100%, such as for example in the range of 95%-100% (including 95% to 99.9%, such as 95%-99%).

Thus in one embodiment of the present invention, the incubation temperature for loading of nanoparticles is in the range of 30° C. to 80° C. and the loading efficiency when using incubation times of 1 to 240 minutes is in the range of 10% to 100% preferably in the range of 80% to 100% and more preferably in the range of 90% to 100%, such as for example in the range of 95%-100% (including 95% to 99.9%, such as 95%-99%).

In a preferred embodiment of the present invention, the incubation temperature for loading of nanoparticles is in the range of 30° C. to 80° C. and the loading efficiency when using incubation times of 1 minutes to 60 minutes is in the range of 10% to 100%, preferably in the range of 80% to 100%, such as 90%-100%, and more preferably in the range of 95% to 100%, such as 95% to 99.9%, or such as 95%-99%).

The methods of the present invention may comprise a step wherein the loaded nanoparticles are purified from the incubation solution as mentioned in step b). Thus, in one embodiment of the invention or the disclosed method of the invention, the generated nanoparticles loaded with radionuclides are purified using SEC, ion-exchange chromatography or dialysis.

In a preferred embodiment of the invention or the disclosed method of the invention, the generated nanoparticles loaded with copper are purified using SEC, ion-exchange chromatography or dialysis.

In one embodiment of the disclosed method, the size of the nanoparticle compositions remains essentially unaltered following loading of said nanoparticles with copper. In another embodiment of the disclosed method, the size of the nanoparticle compositions is altered less than 20% following loading of the nanoparticles with copper isotopes, for example less than 17%, such as less than 14%, for example less than 11%, such as less than 8%, for example less than 5%, such as less than 2%, for example less than 1%.

In one embodiment of the disclosed method, the size of the nanoparticle compositions remains essentially unaltered following loading of said nanoparticles with a radionuclide. In another embodiment of the disclosed method, the size of the nanoparticle compositions is altered less than 20% following loading of the nanoparticles with a radionuclide, for example less than 17%, such as less than 14%, for example less than 11%, such as less than 8%, for example less than 5%, such as less than 2%, for example less than 1%.

In one embodiment of the disclosed method, the zeta potential is altered less than 20% following loading of the nanoparticles with copper isotopes. In another embodiment of the disclosed method, the zeta potential is altered less than 18% following loading of the nanoparticles with copper isotopes, for example less than 16%, such as less than 14%, for example less than 12%, such as less than 10%.

In one embodiment of the disclosed method, the zeta potential is altered less than 20% following loading of the nanoparticles with a radionuclide. In another embodiment of the disclosed method, the zeta potential is altered less than 18% following loading of the nanoparticles with a radionuclide, for example less than 16%, such as less than 14%, for example less than 12%, such as less than 10%.

In a further embodiment the method for preparing nanoparticle compositions encompass controlling the liposome interior pH in the form of protonating or deprotonating the agent-entrapping component, thereby inducing effective loading of the radionuclide.

The described method for preparing nanoparticle compositions may further comprise a step wherein a moiety is attached or associated to the external layer of the nanoparticle which is targeted for a cancerous disease, and in general, pathological conditions associated with leaky blood vessels. In another embodiment of the present invention, method for preparing nanoparticle compositions further comprises step wherein a compound with intracellular targeting properties, such as nuclear localization sequence peptide (NLS peptide), is conjugated to the agent-entrapping component, and/or entrapped within the nanoparticle composition.

A method for preparation of the disclosed nanoparticle composition may further comprise a step of measuring and/or detecting the amount of radiation emitted from the radionuclide entrapped within the nanoparticle composition.

The methods provided by the present invention do not include the use of an ion-transporter such as an ionophore. Thus nanoparticles prepared by the methods of the present invention do not comprise ion-transporters, lipophilic chelators or ionophores.

Kit of Parts

The present invention provides kit of parts for preparation of the nanoparticles.

According to the present invention, such a kit of parts may comprise:
   a. A nanoparticle composition comprising i) a vesicle forming component, and ii) an agent-entrapping component enclosed by the vesicle forming component; and
   b. A composition containing a metal entity for loading into the nanoparticle,
wherein all the components are as described herein.

In one embodiment, the composition containing a metal entity comprises a radionuclide.

The metal entity or radionuclide is either in storage or delivered from the manufacturer depending on the characteristics of the particular radionuclide. The radionuclide may be delivered in the form of a (lyophilized) salt or an aqueous solution or may be synthesized on the premises using existing production facilities and starting materials. Before administration of the radionuclide-containing nanoparticles, parts a, and b of the kit are mixed, and incubated at a temperature higher than 22° C. for a given time period, wherein the incubation temperature and time period are as defined herein.

The efficiency of encapsulation is then tested, preferably using the simple test procedure supplied with the kit. Following test of encapsulation, the drug is administered to the patient.

According to the present invention, a kit of parts may also comprise:

A mixture of a nanoparticle composition comprising a) a vesicle forming component, and b) an agent-entrapping component enclosed by the vesicle forming component; and c) composition containing a metal entity for loading into the nanoparticle, wherein all the components are as described in the present application. Before administration of the radionuclide-containing nanoparticles the mixture of parts a, b and c is incubated at a temperature higher than 22° C. for a given time period, wherein the incubation temperature and time period are as defined herein.

If the metal entity comprises a radionuclide e.g. the positron emitter $^{64}$Cu, said radionuclide is delivered directly from a cyclotron facility to the venue of treatment or diagnosis immediately prior to use, in the form of a (lyophilized) salt or an aqueous solution. Before administration of the radionuclide-containing nanoparticles, parts a and b of the kit are mixed and the efficiency of encapsulation is tested, preferably using the simple test procedure supplied with the kit. Following administration the patient may receive a PET- or a SPECT scan. Optimal visualization may be achieved 4-48 hours after administration.

In another embodiment of the present invention, the patient may be subject to magnetic resonance imaging (MRI) following administration of the nanoparticle compositions as mentioned herein. Such MRI may or may not be combined with PET or SPECT scanning according to the present invention. Thus, according to the present invention, a kit of parts may comprise:
   a. A nanoparticle composition comprising i) a vesicle forming component ii) an agent-entrapping component enclosed by the vesicle forming component and iii) a metal entity useful for MRI; and
   b. A composition containing one or more metal entities for loading into the nanoparticle,
wherein all the components are as described herein, or, a kit of parts may comprise:
   a. A nanoparticle composition comprising i) a vesicle forming component and ii) an agent-entrapping component enclosed by the vesicle forming component; and
   b. A composition comprising one or more metal entities for loading into the nanoparticle,
wherein all the components are as described herein.

In one embodiment of the present invention, the kit of parts comprise a combination of radionuclides useful for combined positron emission tomography (PET) imaging and radiation therapy, for example two radionuclides such as $^{64}$Cu and $^{177}$Lu, or such as $^{64}$Cu and $^{67}$Cu, or such as $^{61}$Cu and $^{67}$Cu, or such as $^{64}$Cu and $^{90}$Y, or such as $^{64}$Cu and $^{119}$Sb, or such as $^{64}$Cu and $^{225}$Ac, or such as $^{64}$Cu and $^{188}$Re, or such as $^{64}$Cu and $^{188}$Re, or such as $^{64}$Cu and $^{211}$At.

In a preferred embodiment of the present invention, the kit of parts comprise a combination of radionuclides useful for combined positron emission tomography (PET) imaging and radiation therapy, such as $^{64}$Cu and $^{177}$Lu.

In another embodiment of the present invention, said kit of parts is for preparation of nanoparticles comprising radionuclides such as for example isotopes of Copper ($^{61}$Cu, $^{64}$Cu, and $^{67}$Cu), wherein said isotopes may or may not be part of the kit of parts. In such an embodiment of the present invention, such a kit of parts may comprise: A nanoparticle composition comprising i) a vesicle forming component, and ii) an agent-entrapping component enclosed by the vesicle forming component. In a further embodiment of the present invention, the kit of parts further comprises an incubation buffer for loading of the metal entities into the nanoparticles.

In a preferred embodiment, any of the kit of parts further comprises a test procedure to assess the efficiency of encapsulation.

The kits of parts for preparation of nanoparticles according to the present invention, do not include an ion-transporter such as an ionophore.

Methods for Treatment or Diagnosis

The nanoparticles of the present invention can be used for diagnosis, monitoring or treatment of diseases or conditions associated with leaky blood vessels in an animal subject in need, for example a mammal in need, such as a human being in need.

Leaky blood vessels are often associated with angiogenesis or neoplastic growth of tissue. Cancer is an example of a disease characterized by leaky blood vessels. Inflammation is another example of a conditions associated with leaky blood vessels.

As mentioned herein, cancer is a disease characterized by leaky blood vessels, and the present invention relates to treatment, monitoring or diagnosis of cancerous diseases associated with malignant neoplasia such as malignant neoplasm of lip, mouth or throat, such as malignant neoplasm of the tongue, the base of tongue, gum, floor of mouth, palate, parotid gland, major salivary glands, tonsil, oropharynx, nasopharynx, piriform sinus, hypopharynx or other parts of lip, mouth or throat or malignant neoplasms of digestive organs such as malignant neoplasms of oesophagus, stomach, small intestine, colon, rectosigmoid junction, rectum, anus and anal canal, liver and intrahepatic bile ducts, gallbladder, other parts of biliary tract, pancreas and spleen, malignant neoplasms of respiratory and intrathoracic organs such as malignant neoplasms of the nasal cavity and middle ear, accessory sinuses, larynx, trachea, bronchus and lung, thymus, heart, mediastinum and pleura, malignant neoplasms of bone and articular cartilage such as malignant neoplasm of bone and articular cartilage of limbs, bone and articular cartilage, malignant melanoma of skin, sebaceous glands and sweat glands, malignant neoplasms of mesothelial and soft tissue such as malignant neoplasm of mesothelioma, Kaposi's sarcoma, malignant neoplasm of peripheral nerves and autonomic nervous system, malignant neoplasm of retroperitoneum and peritoneum, malignant neoplasm of connective and soft tissue such as blood vessels, bursa, cartilage, fascia, fat, ligament, lymphatic vessel, muscle, synovia, tendon, head, face and neck, abdomen, pelvis or overlapping lesions of connective and soft tissue, malignant neoplasm of breast or female genital organs such as malignant neoplasms of vulva, vagina, cervix uteri, corpus uteri, uterus, ovary, Fallopian tube, placenta or malignant neoplasms of male genital organs such as malignant neoplasms of penis, prostate, testis, malignant neoplasms of the urinary tract, such as malignant neoplasms of kidney, renal pelvis, ureter, bladder, urethra or other urinary organs, malignant neoplasms of eye, brain and other parts of central nervous system such as malignant neoplasm of eye and adnexa, meninges, brain, spinal cord, cranial nerves and other parts of central nervous system, malignant neoplasms of thyroid and other endocrine glands such as malignant neoplasm of the thyroid gland, adrenal gland, parathyroid gland, pituitary gland, craniopharyngeal duct, pineal gland, carotid body, aortic body and other paraganglia, malignant neoplasms of head, face and neck, thorax, abdomen and pelvis, secondary malignant neoplasm of lymph nodes, respiratory and digestive organs, kidney and renal pelvis, bladder and other and urinary organs, secondary malignant neoplasms of skin, brain, cerebral meninges, or other parts of nervous system, bone and bone marrow, ovary, adrenal gland, malignant neoplasms of lymphoid, haematopoietic and related tissue such as Hodgkin's disease, follicular non-Hodgkin's lymphoma, diffuse non-Hodgkin's lymphoma, peripheral and cutaneous T-cell lymphomas, non-Hodgkin's lymphoma, lymphosarcoma, malignant immunoproliferative diseases such as Waldenström's macroglobulinaemia, alpha heavy chain disease, gamma heavy chain disease, immunoproliferative small intestinal disease, multiple myeloma and malignant plasma cell neoplasms such as plasma cell leukaemia, plasmacytoma, solitary myeloma, lymphoid leukaemia such as acute lymphoblastic leukaemia, myeloid leukaemia, monocytic leukaemia, blast cell leukaemia, stem cell leukaemia, and other and unspecified malignant neoplasms of lymphoid, haematopoietic and related tissue such as Letterer-Siwe disease, malignant histiocytosis, malignant mast cell tumour, true histiocytic lymphoma or other types of malignant neoplasia.

According to the present invention, a disease associated with leaky blood vessels also may be carcinoma in situ of oral cavity, oesophagus, stomach, digestive organs, middle ear and respiratory system, melanoma in situ, carcinoma in situ of skin, carcinoma in situ of breast, carcinoma in situ of female or male genitals, carcinoma in situ of bladder, urinary organs or eye, thyroid and other endocrine glands, or other types of carcinoma in situ.

The nanoparticles or vesicles of the present invention are preferably for administration to a subject such as a human being.

According to the present invention, the nanoparticles may be administered to a subject in need in a manner which ensures the delivery of the nanoparticles to tissues comprising leaky blood vessels. Such administration may ensure that the nanoparticles are brought into circulation in the blood or the lymph.

In one embodiment of the present invention, the nanoparticles are used for intravenous administration.

In another embodiment of the present invention, the nanoparticles are used for oral administration.

The vesicles or nanoparticles according to the present invention may be used for one or more types of imaging. Such imaging may or be part of a method for treating, monitoring or diagnosis of a disease, monitoring efficiency of treatment by chemotherapy or radiotherapy or condition associated with leaky blood vessels. Imaging according to the present invention comprises x-ray imaging, computed tomography (CT) imaging, magnetic resonance imaging (MRI), positron emission tomography (PET) imaging, single photon emission computed tomography (SPECT) imaging or nuclear scintigraphy imaging.

In one embodiment of the present invention, a method is provided for monitoring, monitoring treatment efficiency, diagnosis or treatment in a subject in need which comprises:
  a. Providing a nanoparticle composition comprising a vesicle forming component, an agent-entrapping component, and one or more entrapped metal entities.
  b. Administering the nanoparticle composition to a subject in need.

In another embodiment of the present invention, a method is provided for monitoring, monitoring treatment efficiency, diagnosis or treatment in a subject in need which comprises:
  a. Providing a nanoparticle composition comprising a vesicle forming component, an agent-entrapping component, and one or more radionuclides entrapped within the nanoparticle.
  b. Administering the nanoparticle composition to a subject by intravenous administration
  c. Measuring the amount of radiation emitted from the radionuclides within the liposome composition after a given incubation time.

or
  a. Providing a nanoparticle composition comprising a vesicle forming component, an agent-entrapping component, and one or more metal entities entrapped within the nanoparticle.
  b. Administering the nanoparticle composition to a subject by intravenous administration
  c. Using conventional imaging methods for measuring the presence and/or location of the metal entities in said subject.

In one embodiment of the present invention, a method for monitoring, monitoring treatment efficiency, diagnosis or treatment of cancer is provided which comprises:
  a. Providing a nanoparticle composition comprising a vesicle forming component, an agent-entrapping component, and a radiolabeled agent comprising one or more radionuclides of the copper isotopes $^{61}$Cu, $^{64}$Cu and $^{67}$Cu which may be Cu(II) cations or Cu(I) cations.
b. Administering the nanoparticle composition to a subject by intravenous administration
c. Measuring the amount of radiation emitted from the radionuclide within the liposome composition after a given incubation time.

EXAMPLES

Example I

Improved Loading of $^{64}$Cu and/or $^{177}$Lu into Liposomes Comprising a Chelating Agent Preparation of Liposome Composition Containing Chelating-Agent:

Chelating-agent (DOTA) was trapped within the liposomes consisting of 1,2-disteraroyl-sn-glycero-3-phosphocholine (DSPC), cholesterol (CHOL) and 1,2-distearoyl-sn-glycero-3-phosphoethanolamine-N-[methoxy(polyethyleneglycol)-2000 (DSPE-PEG-2000) in the molar ratio 50:40:10 using standard thin-film hydration and repeated extrusions. Briefly, the lipids were mixed in chloroform and dried to a lipid-film under a gentle stream of nitrogen. Organic solvent residues were removed under reduced pressure overnight. The lipid-film was dispersed by adding an aqueous solution—a HEPES buffer (10 mM, 150 mM NaCl, pH 7.4) containing the chelating-agent, DOTA, adjusted to either pH 4.0 or pH 7.4 with a concentration of 10 mM and the osmolarity was measured to be 325 mOsm/L. The solution was then hydrated at 65° C. for 60 min. Multi-lamellar vesicles (MLVs) were sized to large unilamellar vesicles (LUVs) by multiple extrusions through 100 nm polycarbonate filters using a mini-extruder. Unentrapped chelating-agent was removed by size exclusion chromatography (SEC) on a Sephadex G-25 packed 1×25 cm column eluted with a HEPES buffer (10 mM, 150 mM NaCl, pH 7.4, 310 mOsm/L).

Figure 1:
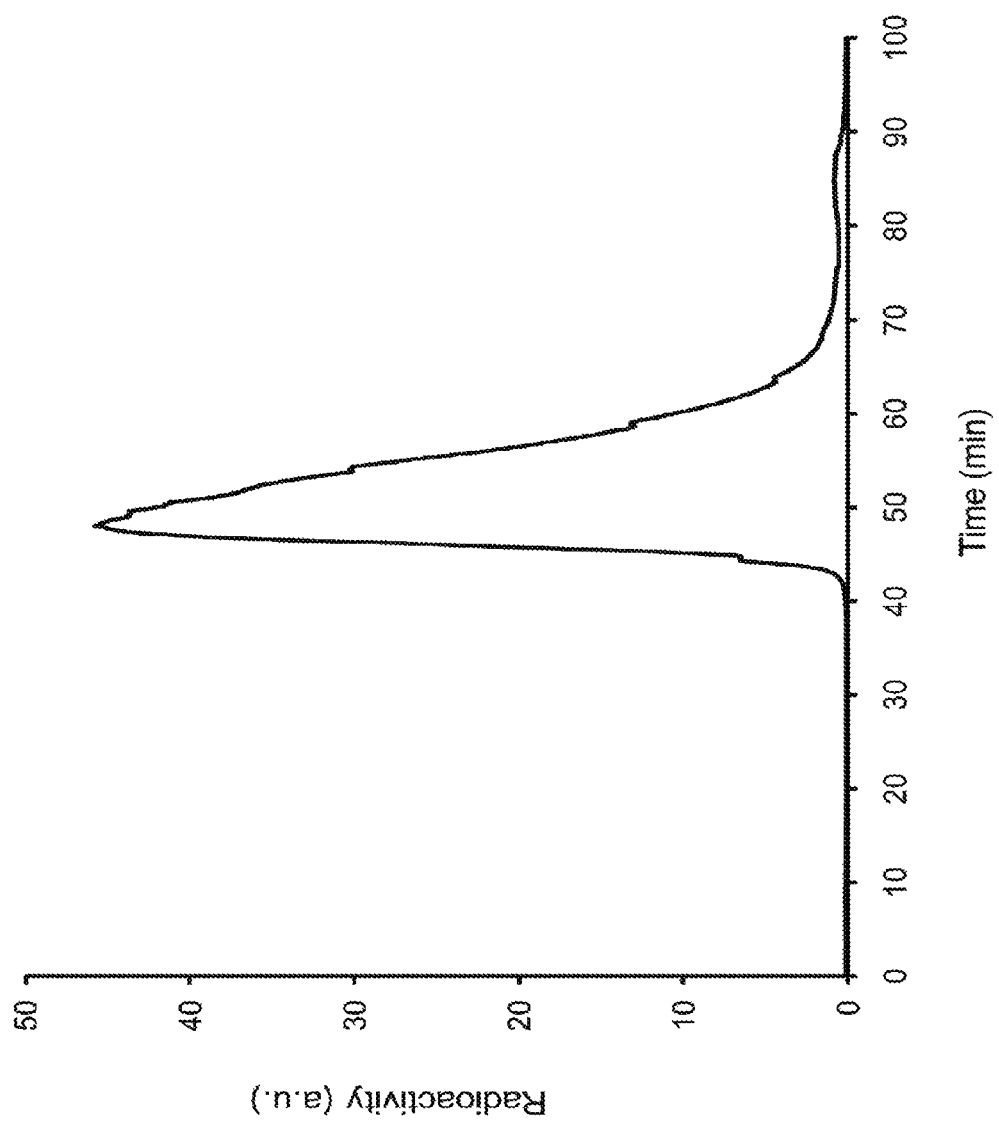
FIG. 1: Separation of $^{64}$Cu-Liposomes and free un-entrapped $^{64}$Cu with size exclusion chromatography (SEC) using a Sephadex G-25 column. Preformed liposomes consisting of DSPC/CHOL/DSPE-PEG$_{2000}$ with DOTA pre-encapsulated were loaded with $^{64}$Cu using an incubation time of 60 min and an incubation temperature of 50-55° C. achieving encapsulation efficiency as high as 96.7%.
Figure 2:
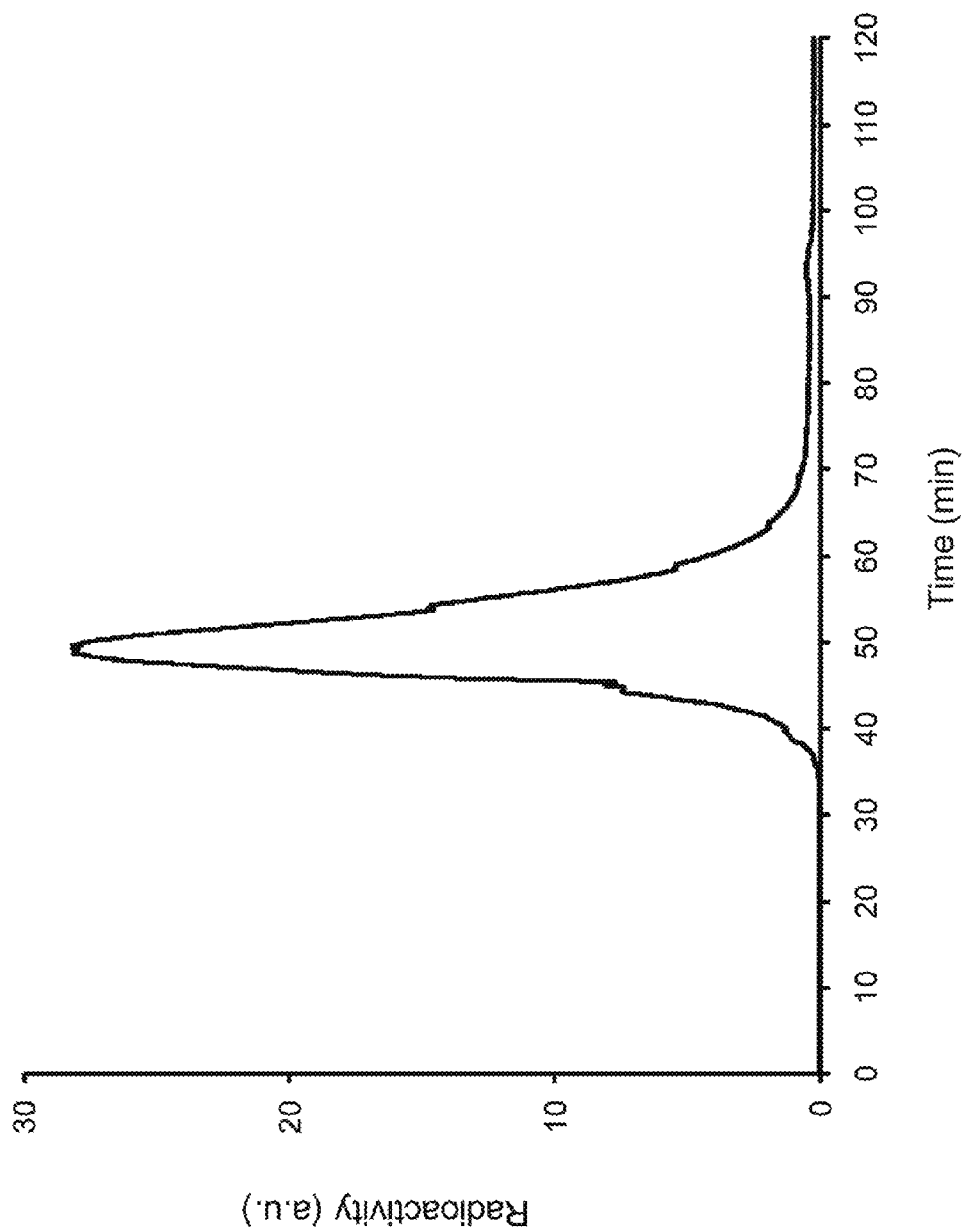
FIG. 2: Separation of $^{177}$Lu-Liposomes and free un-entrapped $^{177}$Lu with size exclusion chromatography (SEC) using a Sephadex G-25 column. Preformed liposomes consisting of DSPC/CHOL/DSPE-PEG$_{2000}$ with DOTA pre-encapsulated were loaded with $^{177}$Lu using an incubation time of 60 min and an incubation temperature of 50-55° C. achieving encapsulation efficiency of 81.0%.

Loading Liposomes with Radionuclide:

The suspension of liposomes prepared as described in the section above, was added to a dried vial containing a radionuclide such a $^{64}$Cu and/or $^{177}$Lu. The suspension was incubated for 60 min at 50-55° C. Radionuclide loading efficiency was greater than 90% for $^{64}$Cu and greater then 80% for $^{177}$Lu. The separation of $^{64}$Cu-Liposomes and free un-entrapped $^{64}$Cu with size exclusion chromatography (SEC) using Sephadex G-25 column is shown in FIG. 1. The separation of $^{177}$Lu-Liposomes and free un-entrapped $^{177}$Lu with size exclusion chromatography (SEC) using Sephadex G-25 column is shown in FIG. 2.

Figure 3:
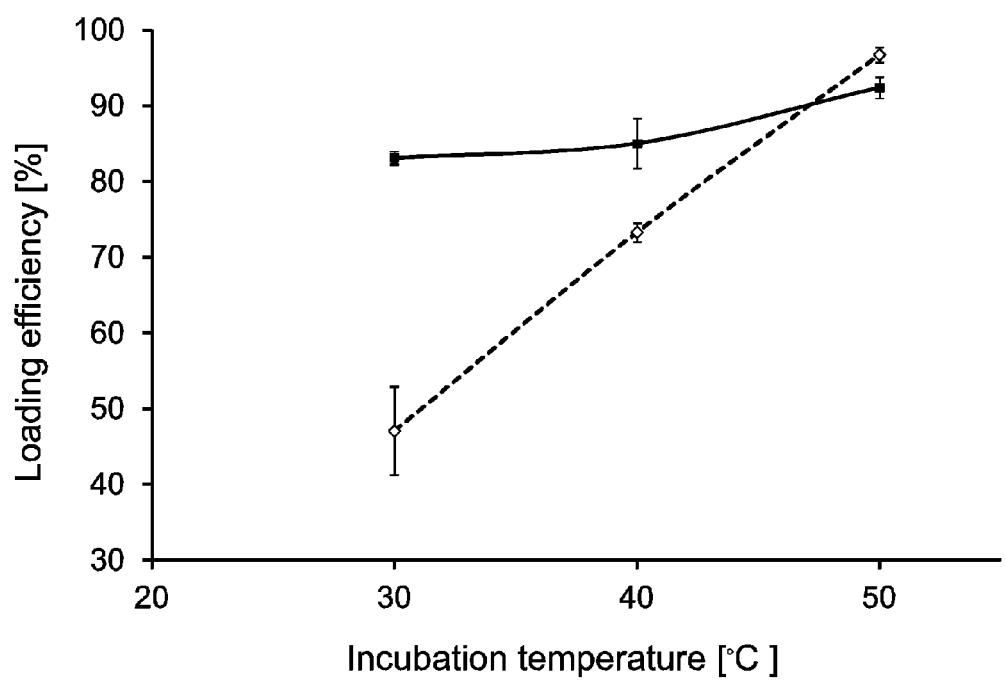
FIG. 3: Loading efficiency of $^{64}$Cu into liposomes as function of incubation temperature without ionophore (dashed line) and with ionophore (2HQ) (solid line). The loading efficiency of $^{64}$Cu loaded into liposomes without ionophore at 50-55° C. was 96.7%.

The loading efficiency of $^{64}$Cu as function of temperature is shown in FIG. 3, and compared to ionophoric loading using 2-hydroxyquinoline (2HQ). The loading efficiency of $^{64}$Cu into liposome compositions when using the ionophore 2HQ was slightly increasing as function of temperature with a maximum loading efficiency (92.4%±1.4%) at 50-55° C. In contrast the loading efficiency of $^{64}$Cu into liposome compositions without using an ionophore was increasing with increasing temperature reaching a higher loading efficiency (96.7%±1.0%) at 50-55° C. compared to the method with ionophore (2HQ).

Storage Stability at 37° C. For 24 h of $^{64}$Cu-Liposome with a Liposomal Interior pH 4.0:

A purified 500 uL $^{64}$Cu-Liposome solution was incubated at 37° C. for 24 h, and the stability of the $^{64}$Cu-Liposome were assayed by separating free $^{64}$Cu from $^{64}$Cu-Liposome by size exclusion chromatography (SEC) on a Sephadex G-25 column. The elution profile was monitored on an in line radioactivity detector. The $^{64}$Cu-Liposomes containing 10 mM DOTA (pH 4.0) retained more than 95% of the total radioactivity. The radionuclide binds preferably to DOTA encapsulated in the interior of the liposome, due to its strong affinity thereto, allowing the entrapment of the radionuclide.

Storage Stability at 37° C. For 24 h of $^{64}$Cu-Liposome with a Liposomal Interior pH 7.4:

A purified 500 uL $^{64}$Cu-Liposome solution was incubated at 37° C. for 24 h, and the stability of the $^{64}$Cu-liposome were assayed by separating free $^{64}$Cu from $^{64}$Cu-Liposome by size exclusion chromatography (SEC) on a Sephadex G-25 column. The elution profile was monitored on an in line radioactivity detector. The $^{64}$Cu-Liposomes containing 10 mM DOTA (pH 7.4) retained more than 95% of the total radioactivity. The radionuclide binds preferably to DOTA encapsulated in the interior of the liposome, due to its strong affinity thereto, allowing the entrapment of the radionuclide.

The disclosed method of producing nanoparticle compositions loaded with radionuclides is a fast and easy preparation of a novel PET imaging agents. The fast preparation is important due to the short half-life of the positron-emitter, $^{64}$Cu, and ideal in manufacturing the product. The method is very robust and consistently gives high loading efficiencies (>95%) using liposome composition containing a chelating-agent, a controlled osmotic pressure on the inside of the liposomes, and with a pH ranging from 4 to 8. It is an advantage of the disclosed method that there are no carriers such as lipophilic ionophores used to load the radionuclides into the liposomes. The disclosed method of preparing nanoparticles containing radionuclides produces nanoparticles retaining >95% of the entrapped radionuclides, which is a necessity for the utilization of these nanoparticle compositions as imaging and therapeutic agents.

Example II

Preparation of Liposome Composition Containing Chelating-Agent for Cu(II)-Loading The loading of non-radioactive $Cu^{2+}$ into chelator-containing liposomes was tested, and evaluated by using an ion Cu(II)-selective electrode. The electrode converts the activity of $Cu^{2+}$ dissolved in a solution into an electrical potential, which is measured by a voltmeter or pH meter. Thus the Cu(II)-selective electrode responds to un-complexed $Cu^{2+}$ ion activity. The sensing part of the electrode is made as an ion-specific membrane, along with a reference electrode.

Chelating-agent (DOTA) was trapped within the liposomes consisting of DSPC, cholesterol and DSPE-PEG-2000 in the molar ratio 50:40:10 using standard thin-film hydration and repeated extrusions. Briefly, the lipids were mixed in chloroform and dried to a lipid-film under a gentle stream of nitrogen. Organic solvent residues were removed under reduced pressure overnight. The lipid-film was dispersed by adding an aqueous solution—a HEPES buffer (10 mM, 150 mM NaNO$_3$, pH 6.85) containing the chelating-agent, DOTA, adjusted to pH 4.0. The solution was then hydrated at 65° C. for 60 min. Multi-lamellar vesicles (MLVs) were sized to large unilamellar vesicles (LUVs) by multiple extrusions through 100 nm polycarbonate filters using a mini-extruder. Unentrapped chelating-agent was removed by size exclusion chromatography (SEC) on a Sephadex G-25 packed 1×25 cm column eluted with a HEPES buffer (10 mM, 150 mM NaNO$_3$, pH 6.85, 310 mOsm/L).

Figure 4:
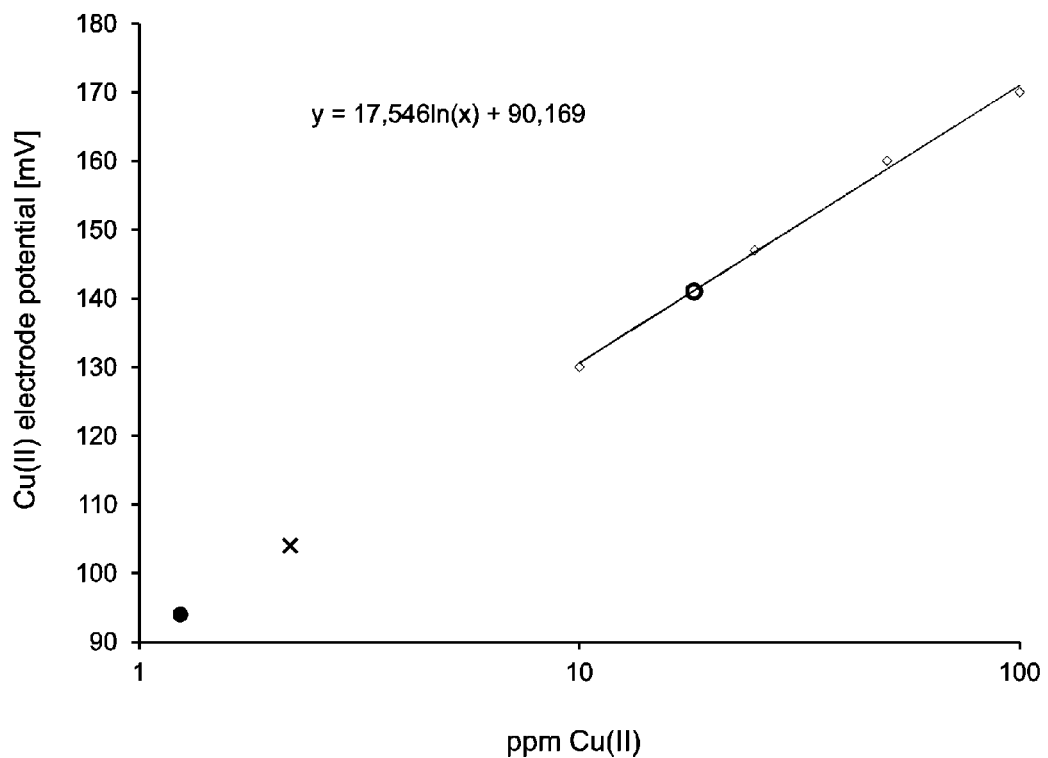
FIG. 4: Plot of standard curve and obtained results from a remote loading experiment of Cu(II) into liposomes consisting of DSPC, CHOL and DSPE-PEG$_{2000}$. The un-complexed Cu$^{2+}$ was measured via an Cu(II)-selective electrode and the achieved loading efficiency was $$\left(1 - \frac{1.2 \text{ ppm}}{25 \text{ ppm}}\right) \cdot 100\% > 95\%.$$

Loading Liposomes with Cu(II):

A sequence of $Cu(NO_3)_2$ standard solutions were prepared and measured using a Cu(II)-selective electrode (FIG. 4). The Cu(II)-selective electrode responds to uncomplexed copper ion activity. $Cu(NO_3)_2$ was added to the liposomes (final concentration of 25 ppm) and the Cu(II)-electrode response was measured to 141 mV (FIG. 4) corresponding to 18.1 ppm uncomplexed Cu(II). The liposome suspension was incubated for 60 min at 50-55° C. for loading Cu(II) into the liposome compositions, giving a Cu(II)-electrode response of 94 mV corresponding to 1.2 ppm Cu(II). The blank (background) measurement (10 mM HEPES buffer, 150 mM $NaNO_3$, pH 6.85) without Cu(II) added gave a Cu(II)-electrode response of 104 mV corresponding to 2.2 ppm Cu(II).

To calculate the loading efficiency the following equation (4) was used:

$$\left(1 - \frac{1.2 \text{ ppm}}{25 \text{ ppm}}\right) \cdot 100\% > 95\% \quad \text{(equation 4)}$$

These results strongly indicates a very high loading efficiency (>95%) of Cu(II) into the liposomes compositions (FIG. 4), when using the disclosed method.

Example III

To test whether the ionophore free loading method was limited to divalent cations, the two radioactive trivalent cations, $^{177}Lu^{3+}$ and $^{111}In^{3+}$, were tested. Loading of the radioactive pertechnetate ($^{99m}Tc$), was also tested. $^{99m}Tc$ is an oxoanion with the chemical formula $TcO_4^-$. Successful loading of both $^{177}Lu^{3+}$ and $^{111}In^{3+}$ in into chelator-containing liposomes without using ionophores was obtained. In contrast no loading was observed of $^{99m}TcO_4^-$ (see Table 1).

The chelator-containing liposomes consisted of DSPC/CHOL/DSPE-$PEG_{2000}$ in the molar ratio 50:40:10. An isotonic HEPES buffer (10 mM HEPES, 150 mM NaCl, pH 7.4, 300 mOsm/L) was used as exterior buffer, and a HEPES buffer containing chelator (10 mM DTPA or DOTA, 10 mM HEPES, 150 mM NaCl, pH 7.4) was used as interior buffer. Approximately 10 μL of radioactive $^{177}LuCl_3$, $^{111}InCl_3$ or $^{99m}Tc$ pertechnetat was added to purified chelator-containing liposomes (500 μL) followed by incubation for 60 min at 50-55° C. The radioactive $^{177}LuCl_3$ and $^{111}InCl_3$ was purchased from Pelkin Elmer, Denmark, and the $^{99m}Tc$ pertechnetat was kindly provided from Køge Hospital, radiology department, Denmark.

TABLE 1

Loading efficiencies of $^{64}Cu^{2+}$, $^{111}In^{3+}$, $^{177}Lu^{3+}$ and $^{99m}TcO_4^-$ into liposomes consisting of DSPC/CHOL/DSPE-$PEG_{2000}$ (50:40:10) with 10 mM chelator entrapped. The loading was carried out for 60 min at 50-55° C. without using ionophore and evaluated by SEC.

| Radionuclide | Entrapped chelator | Loading efficiency [%] |
| --- | --- | --- |
| $^{64}Cu^{2+}$ | DOTA | 98 |
| $^{64}Cu^{2+}$ | DTPA | 95 |
| $^{111}In^{3+}$ | DOTA | 96 |
| $^{177}Lu^{3+}$ | DOTA | 81/88* |
| $^{99m}TcO_4^-$ | DTPA | 0 |

*loading for 4 hours at 65° C.

The results in Table 1 indicate that the loading method leads to cation permeability ($^{64}Cu^{2+}$, $^{177}Lu^{3+}$ and $^{111}In^{3+}$) of liposome compositions with highly favourable loading kinetics.

To characterize and optimize the loading methods of the present invention different experiments were performed and the following parameters were tested; (1) Effect of lipid composition, (2) Effect of lipid concentration and entrapped volume, (3) Effect of free fatty acids, (4) Effect of monovalent ions ($Na^+$, $Cl^-$) and competing divalent ion ($Ca^{2+}$), (5) Effect of chelating components on the exterior, (6) Effect of interior liposomal pH, (7) Phase behavior and effect of loading temperature, (8) Loading kinetics and influence of temperature, (9) Hyper- and hypo-osmotic pressure and (10) $Cu^{2+}$ loading kinetics with and without ionophore.

(1) Effects of Lipid Composition

Liposome compositions within this study are formed from phosphatidylcholines (PC) as 1,2-disteraroyl-sn-glycero-3-phosphocholine (DSPC) and polyethyleneglycol (PEG) derivatized phosphatidyl ethanolamine as 1,2-distearoyl-sn-glycero-3-phosphoethanolamine-N-[methoxy(polyethyleneglycol)-2000] (DSPE-$PEG_{2000}$). Besides DSPC and DSPE-$PEG_{2000}$, cholesterol is incorporated in the membrane. Generally, cholesterol increases bilayer thickness and fluidity while decreasing membrane permeability, and does not add any charge to the membrane. DSPE-$PEG_{2000}$ is negatively charged. The liposomes evaluated here were composed of DSPC, cholesterol and DSPE-$PEG_{2000}$. The overall membrane potential of the liposome composition (evaluated via the zeta-potential) is slightly negative for a liposome with the lipid composition DSPC/CHOL/DSPE-$PEG_{2000}$ 50:40:10; approximately −15 mV when measured in 10 mM HEPES buffer supplemented with 300 mM glucose, pH 7.4, 336 mOsm/L (Table 2). The different liposome compositions in Table 2 were loaded with $^{64}Cu^{2+}$ by incubating liposome compositions with $^{64}Cu^{2+}$ for 60 min at 50-55° C. without using ionophore and evaluated by SEC.

TABLE 2

Loading efficiencies of $^{64}Cu^{2+}$ into different liposome compositions containing 10 mM DOTA encapsulated. Loading was performed without using ionophore and by incubating for 60 min at 50-55° C. and evaluated by SEC.

| Liposome composition (% molar ratio) | Loading efficiency [%] | Zeta potential [mV] |
| --- | --- | --- |
| DSPC/CHOL/DSPE-$PEG_{2000}$ (50:40:10) | 98 | −16.2*/−2.8** |
| DSPC/CHOL/DSPE-$PEG_{2000}$ (55:40:5) | 98 | −15.2*/−6.3** |
| DSPC/CHOL (60:40) | 92 | −11.5*/+2.9** |
| DSPC | 92 | −8.6*/+12.9** |

*Zeta potential was measured in a 10 mM HEPES buffer supplemented with 300 mM glucose, pH 7.4, 336 mOsm/L.
**Zeta potential was measured in a 10 mM HEPES buffer supplemented with 300 mM glucose and 1 mM $CaCl_2$, pH 7.4, 339 mOsm/L.

The negative membrane potential could influence the high loading efficiencies of the cationic metal ions into the liposomes (Table 1). In order to evaluate this, loading experiments were conducted on neutral liposome compositions excluding DSPE-$PEG_{2000}$ only consisting of pure DSPC or a mixture of DSPC and cholesterol in the molar ratio 60:40. All liposome compositions contained high chelator concentrations (DOTA, 10 mM) in the interior. The chelator-containing liposomes were added to a dried vial with radioactive $^{64}CuCl_2$ and incubated for 60 min at 50-55° C. High $^{64}Cu^{2+}$ loading efficiencies were observed with all liposomes compositions (see Table 2).

(2) Effect of Lipid Concentration and Entrapped Volume

Classical means of entrapping drugs (known as loading) into liposomes involves encapsulating the desired drug during the preparation of the liposomes (passive entrapment). Passive entrapment techniques are less efficient in encapsulating drugs or other entities compared to active loading methods (wherein the metal is loaded after preparation of the liposomes). In passive entrapment, the drug or the radionuclide is simply included in the buffer solution from which the liposomes are formed. The liposome size is highly important for passive loading, as passive entrapment strongly depends on the entrapped aqueous volume of the liposomes.

Here, a passive entrapment of $^{64}Cu^{2+}$ was tested. The passive entrapment was carried out as described in the following: A lipid-film was made by mixing the lipids (DSPC, cholesterol and DSPE-PEG$_{2000}$ in the molar ratio of 55:40:5 with a lipid concentration of 50 mM) in chloroform and dried under a gentle stream of nitrogen. Organic solvent residues were removed under reduced pressure overnight. The lipid-film was the dispersed by adding an aqueous solution—a HEPES buffer (10 mM, 150 mM NaCl, pH 7.4) containing the chelating-agent, DOTA, adjusted to either pH 4.0 or pH 7.4 with a concentration of 10 mM together with radioactive $^{64}CuCl_2$. The solution was passively loaded with $^{64}Cu^{2+}$ by hydrating the solution at 65° C. for 60 min. Passively $^{64}Cu$-loaded multi-lamellar vesicles (MLVs) were sized to large unilamellar vesicles (LUVs) $^{64}Cu$-loaded by multiple extrusions through 100 nm polycarbonate filters using a automated dispenser system applicable for radioactive samples and the loading efficiency was evaluated by SEC. An encapsulation efficiency of 6.25% was obtained in a 100 nm sized liposome solution composed of DSPC, cholesterol and DSPE-PEG$_{2000}$ in the molar ratio of 55:40:5 with a lipid concentration of 50 mM. From this the following conclusion was made; ~0.14% $^{64}Cu^{2+}$ is passively encapsulated or associated with the membrane per mM lipid in 100 nm liposomes. This assumption is consistent with estimates of the entrapped volume and encapsulation degree of 100 nm sized unilamellar liposomes:

$$((V_{entrap}/V_{tot})/C_{lip} = Na \cdot a_{lip} \cdot R/6 \sim 0.20\%/mM \qquad \text{Equation 5}$$

$V_{entrap}$ and $V_{tot}$ being the entrapped and total volume, $C_{lip}$ is the lipid concentration, Na is the Avogadro's number, $a_{lip}=40$ Å$^2$ is the approximate average cross-sectional area of the lipid composition used and R is the liposome radius.

To test if the method of loading metal cations into preformed liposomes is proportional to the lipid concentration and the entrapped volume, the uptake of radioactive $^{64}Cu^{2+}$ into neutral membrane compositions consisting of a mixture of DSPC and CHOL in the molar ratio 60:40 without any chelating agent encapsulated was observed. Chelator-free liposomes were prepared as follows: The lipids (DSPC and CHOL) were mixed in chloroform and dried to a lipid-film under a gentle stream of nitrogen. Organic solvent residues were removed under reduced pressure overnight. The lipid-film was dispersed by adding an aqueous solution—a HEPES buffer (10 mM, 150 mM NaCl, pH 7.4) and the osmolarity was measured to be 300 mOsm/L. The solution was then hydrated at 65° C. for 60 min. Multi-lamellar vesicles (MLVs) were sized to large unilamellar vesicles (LUVs) by multiple extrusions through 100 nm polycarbonate filters using a mini-extruder. The buffer used in this experiment was the same used in all other experiments; an isotonic HEPES buffer (10 mM HEPES, 150 mM NaCl, pH 7.4, 300 mOsm/L). The liposomes were incubated with $^{64}Cu^{2+}$ for 60 min at 50-55° C. and evaluated by SEC. The liposomal loaded radioactivity was 0.75% when the lipid concentration was low (5 mM) and 5.3% when the lipid concentration was 10-fold higher (50 mM) (see Table 3).

TABLE 3

Percent radioactivity associated to the liposome compositions without chelator encapsulated. The incubations were carried out for 60 min at 50-55° C. without using ionophore and evaluated by SEC.

| Radionuclide | Liposome composition (% molar ratio) | Lipid concentration [mM] | Loading efficiency [%] |
|---|---|---|---|
| $^{64}Cu^{2+}$ | DSPC/CHOL (60:40) | 50 | 5.3 ± 1.0 |
| $^{64}Cu^{2+}$ | DSPC/CHOL (60:40) | 5 | 0.75 |
| $^{111}In^{3+}$ | DSPC/CHOL/DSPE-PEG$_{2000}$ (50:40:10) | 50 | 4 |

It is clear that the loading efficiency of passive loading using temperatures of 50-55° C. is significantly lower (6.25%) than the loading efficiency obtained by using the loading methods of the present invention (e.g. Table 1 and 2). The results in Table 3 also indicate that loading of $^{64}Cu^{2+}$ into the liposomes without chelator encapsulated using the method of the present invention is proportional to the entrapped volume and/or the lipid concentration of the liposomes, indicating that loading/association of $Cu^{2+}$ into preformed liposomes can occur unassisted by an entrapped chelator. The hypothesis was also tested with the trivalent metal ion, $^{111}In^{3+}$ in showing similar trends as for $^{64}CU^{2+}$ (see Table 3). Either the metal ions are trapped or transported passively in the aqueous phase of preformed liposomes due to simple transmembrane ion equilibrium or the metal ions are associated to the lipids in the membrane of the liposome. The metal ions could bind to or associate to the phosphate moiety in the polar head group of PC. The results in Table 3 clearly demonstrate a correlation between the lipid concentration and/or the entrapped liposomal volume and the $Cu^{2+}$ and $In^{3+}$ ions association to or transport into the liposomes.

(3) Effect of Free Fatty Acids

Free fatty acids (FFA) are known to diffuse (or flip-flop) rapidly across phospholipid bilayers in their protonated form. However, whether flip-flop through the hydrophobic core of the bilayer or desorption from the membrane into the aqueous phase is the rate-limiting step in FFA transport through membranes is still debated. Nevertheless, FFAs are well known to have a destabilizing effect on some liposomal membranes enhancing the permeability of membranes and facilitating the passage of entities over the membrane; however, exceptions are known where FFAs stabilize the gel state of fully saturated lipid membranes. The addition of FFA to lipid bilayer solutions such as liposomes have been shown to dramatically enhance membrane permeability in the presence of e.g. palmitic acid and $Ca^{2+}$ ions [Agafonov et al., BBA, 1609:153-160, 2003]. To evaluate if the high radionuclide loading into the aqueous phase of liposomes without the use of ionophores found for the present invention, could be dependent on the presence of FFA that enhance the trans-bilayer diffusion rate of free metal ions (acyl phospholipids contain small impurities of FFA), the $^{64}CU^{2+}$ loading efficiency was measured for non-FFA containing liposomal membranes. 1,2-Di-O-Hexadecyl-sn-Glycero-3-phosphocholine (1,2-Di-O-DPPC) was used as FFA free lipid component replacing DSPC in the liposome composition (see FIG. 5).

The chelator-containing non-FFA containing liposomes were prepared as described in Example I: Preparation of liposome composition containing chelating-agent, using 1,2-Di-O-Hexadecyl-sn-Glycero-3-phosphocholine (1,2-Di-O-DPPC) and CHOL as vesicle-forming components in the molar ratio 60:40. The chelator-free non-FFA containing liposomes were prepared as described in the above section (2) using 1,2-Di-O-Hexadecyl-sn-Glycero-3-phosphocholine (1,2-Di-O-DPPC) and CHOL as vesicle-forming components in the molar ratio 60:40.

The chelator-containing (10 mM DOTA) non-FFA containing liposomes or chelator-free non-FFA containing liposomes were added to a dried vial with radioactive $^{64}CuCl_2$ and incubated for 60 min at 50-55° C. and evaluated by SEC. A high loading of $^{64}CU^{2+}$ into the interior of the chelator-containing non-FFA containing liposomes was observed (Table 4) with chelator-free non-FFA containing liposomes serve as a control.

TABLE 4

Loading efficiencies of $^{64}Cu^{2+}$ into liposome compositions containing 1,2-Di-O-Hexadecyl-sn-Glycero-3-phosphocholine (1,2-Di-O-DPPC) and CHOL in the molar ratio 60:40 with and without 10 mM DOTA encapsulated. The loading were carried out for 60 min at 50-55° C. without using ionophore and evaluated by SEC.

| Chelator | Liposome composition (% molar ratio) | Lipid concentration [mM] | Loading efficiency [%] |
|---|---|---|---|
| With | 1,2-Di-O-DPPC/CHOL (60:40) | 10 | 93 |
| Without | 1,2-Di-O-DPPC/CHOL (60:40) | 50 | 6 |

1,2-Di-O-DPPC: 1,2-Di-O-Hexadecyl-sn-Glycero-3-phosphocholine

This excludes the possibility that FFAs are inducing the permeability of the free metal ions into the liposomes. Non-FFA containing liposomes without chelator encapsulated served as a control, and gave similar results as for DSPC/CHOL (60:40) without encapsulated chelators (Table 3). The conclusion is that liposomes both with and without FFA in the membrane can be used in the present invention.

(4) Effect of Monovalent Ions ($Na^+$, $Cl^-$) and Competing Divalent Ions ($Ca^{2+}$)

In a study by Hauser and Dawson it was observed that monovalent ions like $Na^+$ and $K^+$ were only effective at displacing $Ca^{2+}$ when they were present at a concentration about $10^4$ times that of $Ca^{2+}$ [Hauser and Dawson, J. Biochem., 1:61-69, 1967], which agrees with the predictions of the double layer theory [Lyklema, ISBN:0-12-460530-3, 5:3.208, 1995]. The double layer is a structure that appears on the surface of an object when it is placed into liquid containing ions. The object might be a solid particle such as a nanoparticle or liposome. In the first layer, the surface charge (either positive or negative) comprises ions adsorbed directly onto the object. The second layer is composed of ions attracted to the surface charge via Coulomb force, thereby electrically screening the first layer. This second layer is loosely associated with the nanoparticle, because it is made of free ions which move in the liquid under the influence of electric attraction and thermal motion rather than being firmly anchored.

As reported above, 5.3% radioactivity was associated/loaded to the liposomes when an isotonic HEPES buffer (10 mM HEPES, 150 mM NaCl, pH 7.4, 300 mOsm/L) was used (Table 3), but if no monovalent ions ($Na^+$ and $Cl^-$) were added (10 mM HEPES, pH 7.4, 5 mOsm/L), 11% radioactivity was associated with the DSPC/CHOL membrane (50 mM) (see Table 5).

TABLE 5

Loading efficiencies of $^{64}Cu^{2+}$ into liposome compositions without chelator encapsulated. The liposome composition consisted of lipid components DSPC and CHOL in the molar ratio 60:40 with a total lipid concentration of 50 mM. The incubations were carried out for 60 min at 50-55° C. without using ionophore and loading was subsequently evaluated by SEC.

| External and internal buffer solution | Loading efficiency [%] |
|---|---|
| 10 mM HEPES (pH 7.4, 5 mOsm/L) | 11 |
| 10 mM HEPES, 150 mM NaCl (pH 7.4, 300 mOsm/L) | 5.3 ± 1.0 |
| 10 mM HEPES, 150 mM NaCl, 10 mM $CaCl_2$ (pH 7.4, 315 mOsm/L) | 3 ± 1 |

This is in agreement with double layer theory predicting a stronger interaction between the negatively charged lipid membrane and $Cu^{2+}$ as the screening is reduced by the removal of NaCl. In order to substantiate this point, we repeated the loading experiment with the DSPC/CHOL membrane (50 mM) at higher ionic strength adding 10 mM of $Ca^{2+}$ (using 10 mM HEPES, 150 mM NaCl, 10 mM $CaCl_2$, pH 7.4, 315 mOsm/L). A significant reduction (3%) of radioactivity was associated to the membrane (see Table 5), indicating that monovalent ions such as $Na^+$ and divalent ions as $Ca^{2+}$ effectively displace $^{64}CU^{2+}$ at the membrane surface thereby reducing the $^{64}Cu^{2+}$ loading rate. This observation is furthermore in agreement with previous investigations on interactions of divalent cations such as $Ca^{2+}$ and $Zn^{2+}$ with phospholipid membranes [Altenbach and Seelig, Biochemistry, 23:3913-3920, 1984; Binder et al., Bio-phys. Chem., 90:57-74, 2001; Huster et al., Biophys. J., 78:3011-3018, 2000]. In addition the study by Binder and Zschörnig [Binder and Zschörnig, Chem. Phys. Lipids, 115:39-61, 2002] showed that $Ca^{2+}$ clearly binds to the lipid headgroup of pure POPC lipid bilayers. From the results reported here it is suggested that the primary binding of the metal cation, $Cu^{2+}$ to the membrane, is reduced by charge screening effects by mono- and divalent ions such as $Ca^{2+}$ and $Na^+$.

Importantly, it can be seen from the results in Table 5 that the loading methods of the present invention of $Cu^{2+}$ (divalent ions, radioactive and non-radioactive, as well as radioactive trivalent cations, $^{177}Lu^{3+}$ and $^{111}In^{3+}$) into chelator-containing liposomes can be conducted both in presence or absence of $Ca^{2+}$, $Na^+$ and $Cl^-$.

(5) Effect of Chelating Components

The distribution between, and binding of free metal ions (radionuclides) to, various components on the outside of the liposomes (such as un-removed chelator, buffer molecules etc.) are important in determining the chemical activity of the free metal ions with respect to trans-membrane diffusion and overall remote loading kinetics. When residual chelators or other metal binding components are present on the outside of the liposomes, the loading kinetics and efficiency is lowered dramatically. This was observed when a chelator-containing liposome solution was spiked with $10^{-6}$ M DOTA prior to incubation. The loading efficiency was lowered to 2% compared to when no chelator components were present on the outside (>95%). To achieve high loading efficiency (for all cations tested ($^{64}Cu^{2+}$, $^{177}Lu^{3+}$ and $^{111}In^{3+}$)) it is important to remove residual chelators (e.g. DOTA) from the outside of the chelator-containing liposomes during preparation. The presence of chelating components on the liposome exterior lowers the cation concentration (e.g. $^{64}Cu^{2+}$, $^{177}Lu^{3+}$ and $^{111}In^{3+}$) in the aqueous phase and thereby the concentration of the membrane associated fraction, which leads to a very low loading efficiency within an appropriate time scale (hours).

Besides chelators, buffer components are able to complex metal ions. It is known that the buffer HEPES (4-(2-hydroxyethyl)-1-piperazineethanesulfonic acid) interacts with $Cu^{2+}$ and forms complexes that undergoes alkaline hydrolysis above pH 6, resulting in $Cu(OH)_2$ precipitation [Sokolowska and Bal, J. Inorg. Biochem., 99:1653-1660, 2005]. It has been proposed that HEPES contain small impurities that have relatively high affinity for $Cu^{2+}$ [Mash and Chin, Anal. Chem., 75:671-677, 2003]. Hypothetically, HEPES could act as carrier molecule of metal ions within the loading methods of the present invention, shedding and transporting the ions over the membrane where they preferentially bind to the pre-encapsulated chelator.

Since similar high loading efficiencies (>95%) of $^{64}Cu^{2+}$ into chelator-containing liposomes (DSPC/CHOL/DSPE-PEG$_{2000}$ in the molar ratio 50:40:10), were obtained when using other buffers such as phosphate buffered saline (PBS) and the "non-coordinating" buffer 2-(N-morpholino)ethanesulfonic acid (MES), HEPES may not act as carrier molecule of Cu(II) (see Table 6). The preparation of the liposomes was carried out as described in Example I: Preparation of chelator-containing liposomes, where HEPES buffer was replace by PBS or MES buffer. The loading was performed for 60 min at 50-55° C. and the loading efficiency was evaluated by SEC.

TABLE 6

Loading efficiencies of $^{64}Cu^{2+}$ into liposome compositions (DSPC/CHOL/DSPE-PEG$_{2000}$ in the molar ratio 50:40:10) containing 10 mM DOTA encapsulated with different external buffer solutions. Loading was performed for 60 min at 50-55° C. without using ionophores and evaluated by SEC.

| External buffer solution | Loading efficiency [%] |
|---|---|
| 10 mM HEPES, 150 mM NaCl (pH 7.4, 300 mOsm/L) | 98 ± 2 |
| 10 mM MES, 150 mM NaCl (pH 5.9, 300 mOsm/L) | 95 |
| 9.5 mM PBS, 150 mM NaCl (pH 7.4, 300 mOsml/L) | 95 ± 3 |

The present results show that a high loading efficiency is obtained using the methods of the present invention with an incubation solution comprising different loading buffers, However, the solubility of dried $^{64}CuCl_2$ was found to be higher and more rapid in HEPES buffer compared to PBS and sterile water at pH 7.4 at 22° C. temperature, which is convenient for the preparation procedure. At higher temperatures the solubility of dried $^{64}CuCl_2$ in HEPES, PBS and sterile water was equal.

(6) Effect of Interior Liposomal pH

An important discovery in liposome loading techniques was that trans-membrane ion gradients can be generated and utilized to actively load and encapsulate ionizable drugs in the aqueous liposome lumen [U.S. Pat. Nos. 5,736,155; 5,077,056; and 5,762,957]. The method involves establishing a pH gradient across a liposome bilayer such that an ionizable drug, to be encapsulated within a liposome, is uncharged in the external buffer and charged within the aqueous interior. This allows the drug to cross the bilayer membrane of the liposome in a neutral form and to be trapped within the aqueous interior of the liposome due to conversion to the charged form. Leakage of drug from actively loaded liposomes has also been found to follow the loss of the proton gradient.

In a previous study on $^{64}Cu^{2+}$ loading into liposomes using the ionophore 2-hydroxyquinoline (2HQ) [Petersen et al., Biomaterials, 32:2334-2341, 2011], >95% and 70% loading efficiency was observed for chelator-containing liposomes with interior pH of 4.0 and 5.9 respectively. The lower degree of loading obtained at pH 5.9 was explained by the less favorable exchange of $^{64}CU^{2+}$ from 2HQ to DOTA. Another ionophore, oxine, was also evaluated, but provided unstable liposomes with respect to $^{64}CU^{2+}$ retention. This instability (release of $^{64}Cu^{2+}$) was explained by the ionophore's ability to dissipate the transmembrane pH gradient, causing the liposomal interior pH to increase, which in the case of oxine, resulted in a reduction of the ligand exchange by several orders of magnitude. Thus ionophores can facilitate the release of entrapped metal ions from liposome compositions.

The influence of interior liposomal pH on the loading efficiency and retention of metal ions was tested with the loading methods of the present invention. Chelating-agent ($C_{DOTA}$=10 mM) was trapped within the liposomes (DSPC/CHOL/DSPE-PEG$_{2000}$ in the molar ratio 50:40:10) adjusted to either pH 4.0 or pH 7.4 as previously described in Example I: Preparation of chelator-containing liposomes. The external buffer was an isotonic HEPES buffer (10 mM HEPES, 150 mM NaCl, pH 7.4, 300 mOsm/L). The incubations of liposomes with $^{64}CU^{2+}$ were carried out for 60 min at 50-55° C. and followingly evaluated by SEC. High loading efficiencies (>95%) of $^{64}CU^{2+}$ were obtained for both interior liposomal pH (4.0 and 7.4) (see Table 7).

TABLE 7

Loading efficiencies of $^{64}Cu^{2+}$ into liposome compositions (DSPC/CHOL/DSPE-PEG$_{2000}$ in the molar ratio 50:40:10) containing 10 mM DOTA encapsulated with different interior pH (pH 4.0 or 7.4). Loading was performed for 60 min at 50-55° C. without using ionophores and followingly evaluated by SEC. External buffer was an isotonic HEPES buffer (10 mM HEPES, 150 mM NaCl, pH 7.4, 300 mOsm/L).

| Internal buffer pH | Loading efficiency [%] | Leakage [%] |
|---|---|---|
| 4.0 | 98 ± 2 | <1% |
| 7.4 | 98 ± 2 | <1% |

In addition, $^{64}CU^{2+}$ loaded liposomes were tested for radionuclide retention by incubating the liposome solutions for 24 h at 37° C. and 20° C. Additionally, stability in human serum of the liposome solutions was tested by mixing human serum and liposome solution (1:1) at 37° C. for 24 h. No release of entrapped radionuclide, $^{64}CU^{2+}$, was observed from any of the liposome solutions (see Table 7).

From the results obtained provided in Table 7 it is clear that the interior pH can easily be raised to pH 7.4 without any influence on loading efficiency or radionuclide retention. Thus the loading method of the present invention is not dependent on any pH gradient across the membrane. An interior pH 7.4 of the liposome is preferable due to possible lipid hydrolysis at lower pH such as pH 4.0. The shelf-life of the chelator-containing liposomes is therefore also significantly prolonged when using interior pH 7.4 compared to pH 4.0.

(7) Phase Behavior and Effect of Loading Temperature

Conventional approaches to liposome formulation dictate inclusion of substantial amounts (e.g. 30-45 mol %) of cholesterol or equivalent membrane rigidifying agents (such as other sterols). Generally, cholesterol increases the bilayer thickness and fluidity while decreasing membrane permeability of the liposome. For example, it has been reported that including increasing amounts of cholesterol in phosphatidylcholine (PC) containing liposomes decreased the leakage of calcein (a fluorescent marker compound) from liposomes in the presence and absence of an osmotic gradient [Allen, et al. Biochim, Biophys. Acta, 597:418-426, 1980]. Another feature of adding cholesterol to lipid bilayers is the formation of a liquid-ordered phase inheriting the stability properties of the liquid-crystalline phase and mobility of the fluid phase. When the DSPC bilayer is supplemented with more than −35 mol % of cholesterol, the main phase transition is completely abolished, and the membrane can be considered to exist in a liquid-ordered phase over a wide temperature range. From differential scanning calorimetry (DSC) experiments it is observed that the liposomal membrane composed of DSPC, CHOL and DSPE-PEG$_{2000}$ in the molar ratio of 50:40:10 does not exhibit any thermal transitions in the range 45-60° C. and thus exists in a single (liquid-ordered like) phase within this temperature range (FIG. 6). Still as shown in FIG. 3, the loading efficiency of $^{64}CU^{2+}$ into liposome compositions without the use of an ionophore was increasing with increasing temperature reaching a high loading efficiency (96.7%±1.0%) at 50-55° C. for 60 min. The efficiencies presented here for loading without use of ionophores are proportional with the increasing temperatures, however, since no phase transition temperature occurs in the liposome composition (FIG. 6), the augmented loading efficiencies are not caused by a phase transition behavior.

(8) Loading Kinetics and Loading Temperature

The kinetics of $^{64}CU^{2+}$ loading into chelator-containing liposomes (DSPC/CHOL/DSPE-PEG$_{2000}$ in the molar ratio 50:40:10), were examined by radio thin layer chromatography (radio-TLC) as the ratio between complexed $^{64}Cu$ (e.g. $^{64}Cu$-DOTA) and the total $^{64}Cu$ amount (sum of complexed ($^{64}Cu$-DOTA) and free $^{64}Cu^{2+}$) as function of time. The loading experiments were carried out in a reaction vial at 30° C., 40° C. and 50° C. and 2 µL samples were spotted on TLC plates at different time points. Thus when $^{64}CU^{2+}$ is loaded into the liposomes, the metal ion binds preferentially to DOTA and $^{64}Cu$-DOTA complex is formed. The TLC plates were run in an organic eluent (10% ammonium acetate: methanol (50:50)) where $^{64}Cu$-DOTA complexes were separated from free $^{64}CuCl_2$. The retention factor (R$_f$) of $^{64}Cu$-DOTA was approximately 0.3 while ionic $^{64}Cu^{2+}$ remained on the origin (R$_f$=0). When the liposome samples were spotted on TLC plates, the liposomes immediately dry out and the interior ($^{64}Cu$-DOTA) runs on the TLC plate. The ratio between the interior $^{64}Cu$-DOTA complex and the total $^{64}Cu$ amount (sum of complexed ($^{64}Cu$-DOTA) and free $^{64}Cu^{2+}$) was calculated as the loading efficiency (defined in equation 1). As a control, free $^{64}CU^{2+}$ was spotted on a TLC plate followed by non-radioactive chelator-containing liposomes on top of $^{64}CU^{2+}$. This control was done to eliminate an erroneous estimation of $^{64}CU^{2+}$ and DOTA complexation occurring on the TLC plate. Since no $^{64}Cu$-DOTA peak was present on the TLC plate, no complexation is occurring on the TLC plate.

The loading of metal ions into liposomes can be divided into several steps including: (i) binding/coordination/adsorption of the ion to the lipid membrane, (ii) trans-bilayer ion diffusion and (iii) binding of ions to the chelator. In the current loading procedure the lipid and chelator are in large excess compared to the $^{64}CU^{2+}$ and the kinetics thus only depends on the $^{64}CU^{2+}$ concentration. The rate of coordination/binding of $Cu^{2+}$ to the membrane is rapid (likely to be diffusion limited) and binding of $Cu^{2+}$ to DOTA occurs on timescale of seconds (verified by radio-TLC) rendering transmembrane ion diffusion as the most probable rate limiting step. In general, the rate of trans-membrane diffusion will depend on the concentration gradient of the transported entity (according to Ficks 1$^{st}$ law), the membrane phase state (gel, fluid or liquid-ordered) and physicochemical (hydrophilicity vs. hydrophobicity) properties of the transported entity. These arguments substantiate the first order equation (Equation 6) presented below. The loading kinetics (example shown in FIG. 7-8) can be characterized by the equation $$\% \text{ load} = \frac{A_{Cu-chelator}}{A_{Cu} + A_{Cu-chelator} + A_{Cu(ionophore)}} = a(1 - be^{-ct}) \quad \text{Equation 6}$$

where $A_{Cu}$, $A_{Cu-chelator}$ and $A_{Cu(ionophore)}$ denote the TLC activity of the $^{64}CU^{2+}$, $^{64}Cu$-DOTA and $^{64}Cu(2HQ)_2$ specie. The fitting parameter a, describes the plateau level (a 100% if loading proceeds according to 1$^{st}$ order kinetics), b describes offset and uncertainty in t (b=1 when offset and uncertainties in t are small) and c describes the loading rate. By fitting of equation 7, each loading profile can be characterized by: (i) the initial velocity:

$$v_{ini} = a \cdot b \cdot c \quad \text{(equation 7)},$$

(ii) the time required to reach 95% loading:

$$t_{(95\%)} = -\ln((1-(95\%)/a)/b)/c \quad \text{(equation 8)},$$

and (iii) the degree of loading reached at 60 min (% load$_{1h}$). The latter is directly comparable to the loading degree achieved using the method based on SEC (presented in FIG. 3 and Tables 1, 2, 6 and 7).

The first order rate constant (c) depends on different parameters such as temperature (see FIG. 7-8) and osmolarity (see next section) at which the loading is conducted. The initial velocity ($v_{ini}$), t$_{(95\%)}$ and % load$_{1h}$ is given in Table 8 for a set of loading conditions.

TABLE 8

Kinetic parameters for loading conducted at 30° C., 40° C. and 50° C., without ionophore for iso-osmotic and hyper-osmotic conditions, and with ionophore (2HQ). The kinetics are characterized by the initial velocity, $v_{ini}$, the time required to achieve 95% loading, t$_{(95\%)}$ and the loading efficiency obtained after 60 min, % load$_{1h}$. All parameters were derived from radio-TLC measurements shown in FIG. 7-8.

|  | $v_{ini}$ [%/min] | t$_{(95\%)}$ [min] | % load$_{1h}$ [%] |
|---|---|---|---|
| Iso-osmotic |  |  |  |
| 30° C. | 0.6 | 220 | 33 |
| 40° C. | 3 | * | 62 |
| 50° C. | 23 | 18 | 99 |
| Hyper-osmotic |  |  |  |
| 30° C. | 0.9 | 240 | 42 |
| 40° C. | 7 | * | 86 |
| 50° C. | 51 | 9 | 99 |
| With ionophore (2HQ) |  |  |  |
| 30° C. | 3 | 80 | 82 |
| 40° C. | 7 | 60 | 94 |
| 50° C. | 100 | 6 | 100 |

* Extrapolation not possible

The loading efficiency of $^{64}Cu^{2+}$ into liposomes at 50° C. at iso-osmotic conditions (FIG. 8) displays a rapid initial rate which gradually declines and saturates as function of time. Upon lowering of the temperature the initial velocity is decreased significantly (Table 8) and the time required for loading 95% is increased from 30 min to several hours (at iso-osmotic loading). Similar temperature effects are observed for loading at hyper-osmotic conditions (discussed in section 9) and for ionophore assisted loading (discussed in section 10).

(9) Hyper- and Hypo-Osmotic Pressure

In order to investigate whether hyper-osmotic conditions increase the loading rate and loading efficiency of metal ions, loading experiments of $^{64}Cu^{2+}$ into chelator-containing liposomes having a hyper-osmotic ($\Delta$(mOsm/L)=+75), a hypo-osmotic ($\Delta$(mOsm/L)=−40) as well as an iso-osmotic gradient ($\Delta$(mOsm/L)=0) (see Table 9) were conducted. The preparation of liposomes and loading experiments were performed as described in Example I, except for changes in the osmolarity of the buffers (see Table 9 below).

TABLE 9

Loading efficiencies of $^{64}Cu^{2+}$ into liposome consisting of DSPC/CHOL/DSPE-PEG$_{2000}$ (50:40:10) using different intra- and extra-liposomal osmolarties. Loading was performed for 60 min at 50-55° C. without using ionophore and evaluated by SEC followingly.

| *$\Delta$(mOsm/L) (Interior buffer #/Exterior buffer#) | Loading efficiency [%] |
|---|---|
| 0 (#1/#3) | 96 |
| +80 (#2/#3) | 98 |
| −40 (#2/#4) | 96 |
| 0 (#2/#5) | 95 |

*$\Delta$(mOsm/L): difference between the internal and external osmolarity liposomal buffer solution. + is higher internal osmolarity and − is lower internal osmolarity.
1: 10 mM DOTA, 10 mM HEPES, 140 mM NaCl, pH 7.4, 295 mOsm/L
2: 10 mM DOTA, 10 mM HEPES, 150 mM NaCl, pH 7.4, 375 mOsm/L
3: 10 mM HEPES, 150 mM NaCl, pH 7.4, 295 mOsm/L
4: 10 mM HEPES, 200 mM NaCl, pH 7.4, 415 mOsm/L
5: 10 mM HEPES, 150 mM NaCl, pH 7.4, 75 mM Sucrose, 375 mOsm/L The liposome compositions consisted of DSPC/CHOL/DSPE-PEG$_{2000}$ in the molar ratio 50:40:10 contained high chelator concentrations (DOTA, 10 mM) in the interior. The osmolarity was controlled by adjusting the NaCl concentration or by adding sucrose (see Table 9). The loading efficiency (evaluated after 60 min) conducted at 50-55° C. (results are compiled in Table 9) showed that high loading efficiency of $Cu^{2+}$ (>94%) is obtained in all cases within the timeframe of the experiment. However, results shown in Table 8 indicate a difference in loading rate between the different osmolarities.

$^{64}Cu^{2+}$ loading kinetics were in addition evaluated as function of time at three different temperatures (30° C., 40° C. and 50° C.) and at two osmotic conditions (iso- and hyper-osmotic) using radio-TLC (FIG. 7-8) with chelator-containing liposomes (DSPC/CHOL/DSPE-PEG$_{2000}$ in the molar ratio 50:40:10). These data (FIG. 7-8) confirm an increased loading rate (initial velocity ($v_{ini}$) in Table 8) and loading efficiency (% load$_{1h}$ in Table 8) with increased temperature for both iso- and hyper-osmotic conditions. The rate and efficiency was further augmented when loading was conducted at hyper-osmotic conditions when compared to iso-osmotic conditions. The largest change in loading rate and loading efficiency upon increased osmolarity were observed at 30° C. and 40° C., whereas little change was found at 50° C.

These results evidence that the loading rate and efficiency can be modulated significantly by tuning parameters as the temperature and the osmolarity. These parameters are important for the effectiveness of the loading method.

(10) $Cu^{2+}$ Loading Kinetics with and without Ionophore

As shown in FIG. 3, the loading efficiency (% load$_{1h}$ evaluated by SEC) of $^{64}Cu^{2+}$ into liposome compositions when using the ionophore 2HQ was weakly increasing as function of temperature with a maximum loading efficiency (92.4%±1.4%) at 50-55° C. for 60 min. In contrast, the loading efficiency of $^{64}Cu^{2+}$ into liposome compositions without the use of an ionophore showed a larger increase with augmented temperature reaching a higher loading efficiency (96.7%±1.0%) at 50-55° C. for 60 min compared to the method with ionophore. These results indicate an increase in loading efficiencies at temperatures below 50° C., when incubating $^{64}Cu^{2+}$, liposomes and ionophore compared to loading without ionophore. The concentration of ionophore used in the loading experiments in FIG. 3 was 100 µM. Ionophores may be toxic to mammals, and therefore the loaded liposomes need to be purified before intravenous injection, which would be a disadvantage in liposome production.

The $^{64}Cu^{2+}$ loading kinetics into the aqueous phase of liposomes consisting of DSPC/CHOL/DSPE-PEG$_{2000}$ in the molar ratio 50:40:10 with and without the use of ionophore ($C_{2HQ}$=100 µM) was compared. To investigate the influence of osmotic pressure on the results of the kinetics, the liposomes were prepared having iso-osmotic conditions. The solutions were incubated at different temperatures (30° C., 40° C. and 50° C.) and evaluated by radio-TLC as function of time (as described above). The radio-TLC results (Table 8) substantiated by results from FIG. 3 show, that the use of an ionophore: (i) increases the loading rate (initial velocity ($v_{ini}$)) and loading efficiency (% load$_{1h}$) (below 50° C.) and (ii) lowers the time required to load 95% ($t_{(95\%)}$). The ionophore assisted loading method furthermore reduces the activation energy for loading, resulting in smaller changes in loading rate and efficiency as a function of temperature variations when compared to non-assisted loading.

Previous studies have shown low ion permeability of phospholipid bilayers such as liposome compositions, which has lead to highly unfavorable loading kinetics for charged ion species [Paula et al., Biophys. J., 74:319-327, 1998; Hauser et al., Nature, 239:342-344, 1972; Ceh et al., J. Phys. Chem. B, 102:3036-3043, 1998; Mills et al., Biochim. Biophys. Acta, 1716:77-96, 2005; Papahadjopoulos et al., Biochim. Biophys. Acta, 266:561-583, 1971; Puskin, J. Membrane Biol, 35:39-55, 1977]. The results from the experiments utilizing the loading methods of the present invention show the opposite, where charged ions as $^{64}Cu^{2+}/^{63}Cu^{2+}$, $^{111}In^{3+}$ and $^{177}Lu^{3+}$ are loaded fast and efficiently into chelator-containing liposomes. The results show that the use of ionophores or other lipophilic complexes to increase trans-bilayer diffusion rates only moderately improves or increases the loading of divalent and trivalent cations, as previously thought.

SUMMARY

The present examples show that divalent and trivalent ions (such as for example 64Cu$^{2+}$, $^{111}In^{3+}$ and $^{177}Lu^{3+}$) are passively transported through liposomal membranes encapsulated in high concentrations in the interior of liposome compositions due to complexation to pre-encapsulated chelators.

REFERENCES

Agafonov et al., BBA, 1609:153-160, 2003
Allen, et al. Biochim, Biophys. Acta, 597:418-426, 1980
Allen, Science, 303: 1818-1822, 2004
Altenbach and Seelig, Biochemistry, 23:3913-3920, 1984
Anderson et al., J Nucl Med., 36: 2315-2325, 1998
Binder et al., Bio-phys. Chem., 90:57-74, 2001
Binder and Zschörnig, Chem. Phys. Lipids, 115:39-61, 2002
Ceh et al., J. Phys. Chem. B, 102:3036-3043, 1998
Dehdashti et al., J Nucl Med. 38: 103P, 1997
Gabizon et al., J Liposome Res., 1: 123-125, 1988
Gabizon et al., Cancer Res., 50: 6371-6378, 1990

Goto et al., Chem harm Bull. (Tokyo), 37: 1351-1354, 1989
Hauser and Dawson, J. Biochem., 1:61-69, 1967
Hauser et al., Nature, 239:342-344, 1972
Henriksen et al., Nucl Med. Bio., 31: 441-449, 2004
Huster et al., Biophys. J., 78:3011-3018, 2000
Hwang et al., Biochim Biophys Acta., 716: 101-109, 1982
Kostarelos et al., J Liposome Res, 9:407-424, 1999
Lyklema, ISBN:0-12-460530-3, 5:3.208, 1995
Mash and Chin, Anal. Chem., 75:671-677, 2003
Mills et al., Biochim. Biophys. Acta, 1716:77-96, 2005
Morgan et al., J Med. Microbiol., 14: 213-217, 1981
Papahadjopoulos et al., Biochim. Biophys. Acta, 266:561-583, 1971
Paula et al., Biophys. J., 74:319-327, 1998
Petersen et al., 2011, Biomaterials, 32:2334-2341, 2011
Phillips, Adv Drug Deliv Rev., 37: 13-32, 1999
Phillips et al., Int J Rad Appl Instrum B, 19: 539-547, 1992
Puskin, J. Membrane Biol, 35:39-55, 1977
Seo et al., Bioconjucate Chem., 19: 2577-2584, 2008
Seo, Curr. Radiopharm., 1: 17-21, 2008
Sokolowska and Bal, J. Inorg. Biochem., 99:1653-1660, 2005

The invention claimed is:

1. A method for preparation of a liposome loaded with metal cations, said method comprising:
   a) forming a liposome comprising a vesicle forming component and a water soluble and non-lipophilic chelator enclosed in said liposome; and
   b) entrapping the metal cations within the interior of the liposome by enabling transfer of metal cations across a membrane formed by the vesicle forming component by incubation of the liposome in a solution comprising the metal cations without using an ionophore as transporting molecule.

2. The method of claim 1, wherein loading efficiency or entrapment of radionuclide is greater than 80%.

3. The method of claim 1, wherein the liposome is incubated at a temperature between 10° C. and 80° C.

4. The method of claim 1, wherein the liposome is incubated for a time period of 1 to 240 minutes.

5. The method of claim 1, wherein said metal cations are divalent or trivalent.

6. The method of claim 1, wherein the metal cations comprise one or more radionuclides selected from the group consisting of Copper ($^{61}$Cu, $^{64}$Cu, and $^{67}$Cu), Indium ($^{111}$In), Technetium ($^{99m}$Tc), Rhenium ($^{186}$Re, $^{188}$Re), Gallium ($^{67}$Ga, $^{68}$Ga), Strontium ($^{89}$Sr), Samarium ($^{153}$Sm), Ytterbium ($^{169}$Yb), Thallium ($^{201}$Tl), Astatine ($^{211}$At), Lutetium ($^{177}$Lu), Actinium ($^{225}$Ac), Yttrium ($^{90}$Y), Antimony ($^{119}$Sb), Tin ($^{117}$Sn, $^{113}$Sn), Dysprosium ($^{159}$Dy), Cobalt ($^{56}$Co), Iron ($^{59}$Fe), Ruthenium ($^{97}$Ru, $^{103}$Ru), Palladium ($^{103}$Pd), Cadmium ($^{115}$Cd), Tellurium ($^{118}$Te, $^{123}$Te), Barium ($^{131}$Ba, $^{140}$Ba), Gadolinium ($^{149}$Gd, $^{151}$Gd), Terbium ($^{160}$Tb), Gold ($^{198}$Au, $^{199}$Au), Lanthanum ($^{140}$La), and Radium ($^{223}$Ra, $^{224}$Ra).

7. The method of claim 1, wherein the metal cations are radionuclides selected from the group consisting of $^{61}$Cu, $^{64}$Cu, $^{67}$Cu, $^{177}$Lu, $^{67}$Ga, $^{68}$Ga, $^{225}$Ac, $^{90}$Y, $^{186}$Re, $^{188}$Re, $^{119}$Sb, and $^{111}$In.

8. The method of claim 1, wherein the metal cations are radionuclides selected from the group consisting of $^{61}$Cu, $^{64}$Cu, $^{67}$Cu, $^{111}$In and $^{177}$Lu.

9. The method of claim 1, wherein one or more metal cations are selected from the group of Gd, Dy, Ti, Cr, Mn, Fe, Co, Ni.

10. The method of claim 1, wherein the metal cations are two or more radionuclides selected from the group consisting of $^{64}$Cu and $^{67}$Cu, $^{61}$Cu and $^{67}$Cu, $^{64}$Cu and $^{90}$Y, $^{64}$Cu, and $^{119}$Sb, $^{64}$Cu and $^{225}$Ac, $^{64}$Cu and $^{188}$Re, $^{64}$Cu and $^{186}$Re, $^{64}$Cu and $^{211}$At, $^{64}$Cu and $^{67}$Ga, $^{61}$Cu and $^{177}$Lu, $^{61}$Cu and $^{90}$Y, $^{61}$Cu and $^{119}$Sb, $^{61}$Cu and $^{225}$Ac, $^{61}$Cu and $^{188}$Re, $^{61}$Cu and $^{186}$Re, $^{61}$Cu and $^{211}$At, $^{61}$Cu and $^{67}$Ga, $^{67}$Cu and $^{177}$Lu, $^{67}$Cu and $^{90}$Y, $^{67}$Cu and $^{119}$Sb, $^{67}$Cu and $^{225}$Ac, $^{67}$Cu and $^{188}$Re, $^{67}$Cu and $^{186}$Re, $^{67}$Cu and $^{211}$At, $^{68}$Ga and $^{177}$Lu, $^{68}$Ga and $^{90}$Y, $^{68}$Ga and $^{119}$Sb, $^{68}$Ga and $^{225}$Ac, $^{68}$Ga and $^{188}$Re, $^{68}$Ga and $^{186}$Re, $^{68}$Ga and $^{211}$At, and $^{68}$Ga and $^{67}$Cu.

11. The method of claim 1, wherein there is a difference in osmotic pressure between the exterior of the liposomes and the interior of the liposomes during incubation.

12. The method of claim 1, wherein said vesicle-forming component comprises one or more of the compounds selected from the group consisting of lipids, ceramides, sphingolipids, phospholipids, and pegylated phospholipids.

13. The method of claim 1, wherein the vesicle forming component comprises one or more amphiphatic compounds selected from the group of HSPC, DSPC, DPPC, POPC, CHOL, DSPE-PEG-2000 and DSPE-PEG-2000-TATE.

14. The method of claim 1, wherein said chelator is selected from the group consisting of 1,4,7,10-tetraazacyclododecane ([12]aneN4); 1,4,7,10-tetraazacyclotridecane ([13]aneN4); 1,4,8,11-tetraazacyclotetradecane ([14]aneN4); 1,4,8,12-tetraazacyclopentadecane ([15]aneN4); 1,5,9,13-tetraazacyclohexadecane ([16]aneN4); ethylene-diamine-tetraacetic-acid (EDTA); diethylene-triamine-penta-acetic acid (DTPA), 1,4-ethano-1,4,8,11-tetraazacyclotetradecane (et-cyclam); 1,4,7,11-tetraazacyclotetradecane (iso-cyclam); 1,4,7,10-tetraazacyclododecane-1,4,7,10-tetraacetic acid (DOTA); 2-(1,4,7,10-tetraazacyclododecan-1-yl)acetate (DO1A); 2,2'-(1,4,7,10-tetraazacyclododecane-1,7-diyl) diacetic acid (DO2A); 2,2',2''-(1,4,7,10-tetraazacyclododecane-1,4,7-triyl) triacetic acid (DO3A); 1,4,7,10-tetraazacyclododecane-1,4,7,10-tetra(methanephosphonic acid) (DOTP); 1,4,7,10-tetraazacyclododecane-1,7-di(methanephosphonic acid) (DO2P); 1,4,7,10-tetraazacyclododecane-1,4,7-tri(methanephosphonic acid) (DO3P); 1,4,8,11-15 tetraazacyclotetradecane-1,4,8,11-tetraacetic acid (TETA); 2-(1,4,8,11-tetraazacyclotetradecane-1-yl) acetic acid (TE1A); 2,2'-(1,4,8,11-tetraazacyclotetradecane-1,8-diyl) diacetic acid (TE2A); ethylene-diamine-tetraacetic-acid (EDTA), and diethylene-triamine-penta-acetic acid (DTPA).

15. The method of claim 1, wherein the interior pH of the liposome is within the range of 4 to 8.5.

16. The method of claim 1, wherein the stability of the radiolabeled liposomes is such that less than 20% leakage of radioactivity is observed.

* * * * *